(12) United States Patent
Lentzen et al.

(10) Patent No.: US 6,271,368 B1
(45) Date of Patent: Aug. 7, 2001

(54) RECOMBINANT MISTLETOE LECTIN (RML)

(75) Inventors: Hans Lentzen, Rösrath; Jürgen Eck, Heppenheim; Axel Baur, Meerbusch-Ossum; Holger Zinke, Bickenbach, all of (DE)

(73) Assignee: Madus Ag Köln, Köln (DE)

( * ) Notice: Subject to any disclaimer, the term of this patent is extended or adjusted under 35 U.S.C. 154(b) by 0 days.

(21) Appl. No.: 08/776,059

(22) PCT Filed: Jun. 25, 1996

(86) PCT No.: PCT/EP96/02773

§ 371 Date: Jun. 19, 1997

§ 102(e) Date: Jun. 19, 1997

(87) PCT Pub. No.: WO97/01636

PCT Pub. Date: Jan. 16, 1997

(30) Foreign Application Priority Data

Jun. 26, 1995 (EP) .................................................. 95109949

(51) Int. Cl.$^7$ .............................. C12N 1/21; C12N 5/10; C12N 15/29; C12N 15/63
(52) U.S. Cl. ....................... 536/23.6; 536/23.1; 536/23.4; 435/320.1; 435/325; 435/410; 435/348; 435/252.3; 435/254.11; 435/69.3; 514/2; 514/12; 424/130.1
(58) Field of Search ................................. 536/23.1, 23.4, 536/23.6; 435/320.1, 325, 410, 348, 252.3, 254.11, 69.3; 530/350, 300, 387.1; 514/2, 12; 424/130.1

(56) References Cited

U.S. PATENT DOCUMENTS 5,407,454 * 4/1995 Cavalieri et al. ......................... 47/58

FOREIGN PATENT DOCUMENTS 42 21 836   1/1994 (DE) .
43 41 476   6/1995 (DE) .

OTHER PUBLICATIONS

Bowie et al. Science 247:1306–1310, 1990.*
Wells, Biochemistry 29:8509–8517, 1990.*
Ngo et al. The Protein Folding Problem and Tertiary Structure Prediction, Merz et al., eds., Birkhauser, Boston, pp. 492–495, 1994.*

Schulz et al. Principles of Protein Structure, Springer–Verlag, New York, pp. 14–16, 1979.*

Anticancer Research 12 (3). 1992. 669–675, Gabius, H.M. et al.

Arch Immunol Ther Exp 40 (3–4). 1992. 223–227, Paprocka M. et al.

Int J Immunopharmacol 13 (7). 1991. 1037–1041, Tonevitsky, A. et al.

Anti–Cancer Drugs 3 (5). 1992. 507–511, Dietrich, J. et al.

Chrispeels, M & Raikhel, N., "Lectins, Lectin Genes, and Their Role in Plant Defense" Plant Cell vol. 3, 1–9, Jan. 1991.

Tonevitsky A.G. et al., Immunology Letters, (1995) 46/1–2 (5–8) XP000611461, "Hybridoma cells producing antibodies against A–chain of mistletoe lectin I are resistant to this toxin."

* cited by examiner

Primary Examiner—Elizabeth Kemmerer
(74) Attorney, Agent, or Firm—Frommer Lawrence & Haug LLP; Thomas J. Kowalski

(57) ABSTRACT

The invention relates to nucleic acid molecules encoding preproproteins having after maturation the biological activity of the mistletoe lectin dimer, to vectors comprising these nucleic acid molecules, to hosts transformed with said vectors and to polypeptides and/or polypeptide dimers which are encoded by these nucleic acid molecules. The polypeptides and/or polypeptide dimers of the invention are widely therapeutically applicable. Thus, the present invention further relates to immunotoxins as well as to pharmaceutical compositions that contain the polypeptides and/or the polypeptide dimers of the invention. Additionally, the invention relates to diagnostic compositions comprising the nucleic acid molecules of the invention, the polypeptides and/or the polypeptide dimers of the invention and/or primers which hybridize specifically to the nucleic acid molecules of the invention. Finally, the invention relates to plant protective agents comprising the polypeptides of the invention and/or the polypeptide dimers of the invention.

56 Claims, 18 Drawing Sheets

Cloning Strategy

FIG. 1b
Construction of N-terminal A- and B- chain oligonucleotides

RML A1 (Pos ricA 14-22): N-terminal ML-A-chain

| | | | | | | | | | | |
|---|---|---|---|---|---|---|---|---|---|---|
| | | H | Q | T | T | G | E | E | Y | F |
| GAA | TTC | CAC | CAA | ACI | ACI | GGI | GAA | GAA | TAC | TT |
| | | T | G | | | | G | G | T | |

RML B1/B2/B3 N-terminal ML-B-chain 1-19

| | | | | | | | | | | | | | | | | | | |
|---|---|---|---|---|---|---|---|---|---|---|---|---|---|---|---|---|---|---|
| D | D | V | T | S | S | A | E | P | T | V | R | I | V | G | R | N | G | M |
| GAC | GAC | GTA | ACA | TCA | TCA | GCA | GAA | CCA | ACA | GTA | CGA | ATA | GTA | GGA | CGA | AAC | CGA | ATG |
| T | T | C | C | C | C | C | G | C | C | C | C | C | C | C | C | T | C | |
| | | G | G | G | G | G | | G | G | G | G | T | G | G | G | | G | |
| | | T | T | T | T | T | | T | T | T | T | | T | T | T | | T | |
| | | | | AGC | AGC | | | | | | AGA | | | | AGA | | | |
| | | | | T | T | | | | | | G | | | | G | | | |

| | | | |
|---|---|---|---|
| RML B1 | (mlB 1-7) | 2304/9216 | combination |
| RML B2 | (mlB 8-13) | 768 | combination |
| RML B3 | (mlB 14-19) | 768 | combination |

Construction of active-site oligonucleotide RMLA2

Sequence comparison of Type-I/II ribosome inactivating proteins (A-chain fragments)

```
             201                                                     250
T.aestivum   ALYGRTKADK TSGPKQQQAR EAVTTLLLMV H...EATRFQ TVSGFVAGVL
H.vulgare    ALHGRTKADK ASGPKQQQAR EAVTTLLLMV N...EATRFQ TVSGFVAGLL
T-santhin    ALDSAITTLF YYNANSA... ..ASALMVLI QSTSEAARYK FIEQQIGKRV
Momordin-a   ALDSAISTLL HYDSTAA... ..AGALLVLI QTTAEAARFK YIEQQIQERA
Luffin-a     ALDSAITTLF HYDSTAA... ..AAAFLVII QTTAEASRFK YIEGQIIERI
Luffin-b     AFDSAITSLF HYDSTAA... ..AGAFLVII QTTAEASRFK YIEGQIIERI
Momordin-b   ALSSAITTLF YYNAQSA... ..PSALLVLI QTTAEAARFK YIERHVAKYV
Ricin        PLEEAISALY YYSTGGTQLP TLARSFIICI QMISEAARFQ YIEGEMRTRI
RCA          PLEDAISALY YYSTCGTQIP TLARSFMVCI QMISEAARFQ YIEGEMRTRI
Abrin        ALTHAIS... FLRSGASNDE EKARTLIVII QMASEAARYR YISNRVGVSI
MAP          RLENSIVNI. .YGKAGDV.K KQAKFFLLAI QMVSEAARFK YISDKIPSEK
Saporin-2    LLLTFMEAV. .NKKARVV.K NEARFLLIAI QMTAEVARFR YIQNLVTKNF
Saporin-6    LLSTSMEAV. .NKKARVV.K DEARFLLIAI QMTAEAARFR YIQNLVIKNF
Saporin-3    LLSTLMDAV. .NKKARVV.K NEARFLLIAI QMTAEAARFR YIQNLVTKNF
Dianthin     LLITMIDGV. .NKKVRVV.K DEARFLLIAI QMTAEAARFR YIQNLVTKNF
PAP-S        ILSSDIGKI. .SGQGSFTEK IEAKFLLVAI QMVSEAARFK YIENQVKTNF
cPAP         ILDSNIGKI. .SGVMSFTEK TEAEFLLVAI QMVSEAARFK YIENQVKTNF
a-PAP        ILNSGIGKI. .YGVDSFTEK TEAEFLLVAI QMVSEAARFK YIENQVKTNF
```

Analysis of active-site region
(region ricA 167-187)
(position according to ricin scheme)

```
167                  187
SFIICIQMISEAARFQYIEGE   Ricin (RiP-II)
TLIVIIQMASEAARYRYISNR   Abrin (RiP-II)
FLLIAIQMVSEAARFKYISDK   MAP (RiP-I)
FLLIAIQMTAEAARFRYIQNL   Saporin-6 (RiP-I)
FLLVAIQMVSEAARFKYIENQ   PAP (RiP-1)
```

Analysis of codon probability
(region ricA 172-181)

```
 I   Q   M   I   S   E   A   A   R   F
ATA CAA ATG ATA TCA GAA GCA GCA CGA TTC
  C   G       C   C   G   C   C   C   T
  T           T   G       G   G   G
                  T       T   T   T
                AGC             AGA
                  T               G
             V
            GTI
             A
            GCI
             T
            ACI
``` low degeneration active-site oligonucleotide chosen for amplification

RML A2 (Pos. ricA 181-172):

```
HOOC-              F   R   A   A   E   S  I/V  M   Q   I   -NH2
5´-AT GGA TCC     AAA III IGC IGC CTC III IAC CAT CTG IAT  -3´
      BamH1       G               T         T       G
```

FIG. 1c

PCR-amplification of ML-gene fragments from Viscum album whole genomic DNA

FIG. 2

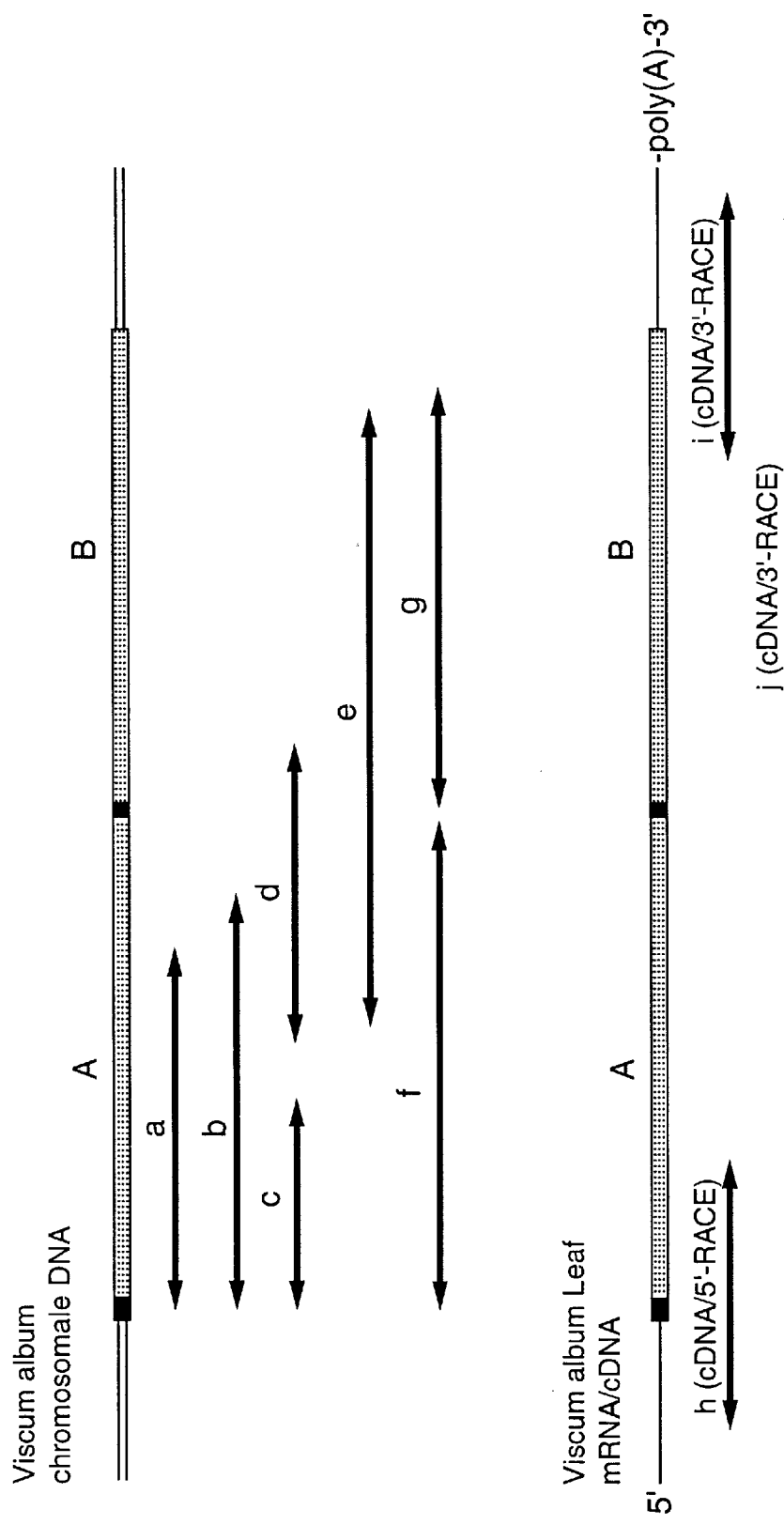

Recombinant insertions of expression vectors pT7MLA and pT7MLB a: MLA

```
1/1                                    31/11
CAT ATG TAC GAA CGT ATC CGT CTG CGT GTT ACC CAC CAG ACC ACC GGT GAA GAA TAT TTC
NdeI Met tyr glu arg ile arg leu arg val thr his gln thr thr gly glu glu tyr phe
61/21                                  91/31
CGG TTC ATC ACG CTT CTC CGA GAT TAT GTC TCA AGC GGA AGC TTT TCC AAT GAG ATA CCA
arg phe ile thr leu leu arg asp tyr val ser ser gly ser phe ser asn glu ile pro
121/41                                 151/51
CTC TTG CGT CAG TCT ACG ATC CCC GTC TCC GAT GCG CAA AGA TTT GTC TTG GTG GAG CTC
leu leu arg gln ser thr ile pro val ser asp ala gln arg phe val leu val glu leu
181/61                                 211/71
ACC AAC CAG GGG GGA GAC TCG ATC ACG GCC GCC ATC GAC GTT ACC AAT CTG TAC GTC GTG
thr asn gln gly gly asp ser ile thr ala ala ile asp val thr asn leu tyr val val
241/81                                 271/91
GCT TAC CAA GCA GGC GAC CAA TCC TAC TTT TTG CGC GAC GCA CCA CGC GGC GCG GAA ACG
ala tyr gln ala gly asp gln ser tyr phe leu arg asp ala pro arg gly ala glu thr
301/101                                331/111
CAT CTC TTC ACC GGC ACC ACC CGA TCC TCT CTC CCA TTC AAC GGA AGC TAC CCT GAT CTG
his leu phe thr gly thr thr arg ser ser leu pro phe asn gly ser tyr pro asp leu
361/121                                391/131
GAG CGA TAC GCC GGA CAT AGG GAC CAG ATC CCT CTC GGT ATA GAC CAA CTC ATT CAA TCC
glu arg tyr ala gly his arg asp gln ile pro leu gly ile asp gln leu ile gln ser
421/141                                451/151
GTC ACG GCG CTT CGT TTT CCG GGC GGC AGC ACG CGT ACC CAA GCT CGT TCG ATT TTA ATC
val thr ala leu arg phe pro gly gly ser thr arg thr gln ala arg ser ile leu ile
481/161                                511/171
CTC ATT CAG ATG ATC TCC GAG GCC GCC AGA TTC AAT CCC ATC TTA TGG AGG GCT CGC CAA
leu ile gln met ile ser glu ala ala arg phe asn pro ile leu trp arg ala arg gln
541/181                                571/191
TAC ATT AAC AGT GGG GCG TCA TTT CTG CCA GAC GTG TAC ATG CTG GAG CTG GAG ACG AGT
tyr ile asn ser gly ala ser phe leu pro asp val tyr met leu glu leu glu thr ser
601/201                                631/211
TGG GGC CAA CAA TCC ACG CAA GTC CAG CAT TCA ACC GAT GGC GTT TTT AAT AAC CCA ATT
trp gly gln gln ser thr gln val gln his ser thr asp gly val phe asn asn pro ile
661/221                                691/231
CGG TTG GCT ATA CCC CCC GGT AAC TTC GTG ACG TTG ACC AAT GTT CGC GAC GTG ATC GCC
arg leu ala ile pro pro gly asn phe val thr leu thr asn val arg asp val ile ala
721/241                                751/251
AGC TTG GCG ATC ATG TTG TTT GTA TGC GGA GAG CGG CCA TCT TAA TAG GGA TCC
ser leu ala ile met leu phe val cys gly glu arg pro ser STP STP BamHI
``` b: MLB

```
1/1                                    31/11
CAT ATG GAT GAT GTT ACC TGC AGT GCT TCG GAA CCT ACG GTG CGG ATT GTG GGT CGA AAT
NdeI Met asp asp val thr cys ser ala ser glu pro thr val arg ile val gly arg asn
61/21                                  91/31
GGC ATG TGC GTG GAC GTC CGA GAT GAC GAT TTC CGC GAT GGA AAT CAG ATA CAG TTG TGG
gly met cys val asp val arg asp asp asp phe arg asp gly asn gln ile gln leu trp
121/41                                 151/51
CCC TCC AAG TCC AAC AAT GAT CCG AAT CAG TTG TGG ACG ATC AAA AGG GAT GGA ACC ATT
pro ser lys ser asn asn asp pro asn gln leu trp thr ile lys arg asp gly thr ile
181/61                                 211/71
CGA TCC AAT GGC AGC TGC TTG ACC ACG TAT GGC TAT ACT GCT GGC GTC TAT GTG ATG ATC
arg ser asn gly ser cys leu thr thr tyr gly tyr thr ala gly val tyr val met ile
241/81                                 271/91
TTC GAC TGT AAT ACT GCT GTG CGG GAG GCC ACT CTT TGG CAG ATA TGG GGC AAT GGG ACC
phe asp cys asn thr ala val arg glu ala thr leu trp gln ile trp gly asn gly thr
301/101                                331/111
ATC ATC AAT CCA AGA TCC AAT CTG GTT TTG GCA GCA TCA TCT GGA ATC AAA GGC ACT ACG
ile ile asn pro arg ser asn leu val leu ala ala ser ser gly ile lys gly thr thr
361/121                                391/131
CTT ACG GTG CAA ACA CTG GAT TAC ACG TTG GGA CAG GGC TGG CTT GCC GGT AAT GAT ACC
leu thr val gln thr leu asp tyr thr leu gly gln gly trp leu ala gly asn asp thr
421/141                                451/151
GCC CCA CGC GAG GTG ACC ATA TAT GGG TTC AGG GAC CTT TGC ATG GAA TCA AAT GGA GGG
ala pro arg glu val thr ile tyr gly phe arg asp leu cys met glu ser asn gly gly
481/161                                511/171
AGT GTG TGG GTG GAG ACG TGC GTG AGT AGC CAA AAG AAC CAA AGA TGG GCT TTG TAC GGG
ser val trp val glu thr cys val ser ser gln lys asn gln arg trp ala leu tyr gly
541/181                                571/191
GAT GGT TCT ATA CGC CCC AAA CAA AAC CAA GAC CAA TGC CTC ACC TGT GGG AGA GAC TCC
asp gly ser ile arg pro lys gln asn gln asp gln cys leu thr cys gly arg asp ser
601/201                                631/211
GTT TCA ACA GTA ATC AAT ATA GTT AGC TGC AGC GCT GGA TCG TCT GGG CAG CGA TGG GTG
val ser thr val ile asn ile val ser cys ser ala gly ser ser gly gln arg trp val
661/221                                691/231
TTT ACC AAT GAA GGG GCC ATT TTG AAT TTA AAG AAT GGG TTG GCC ATG GAT GTG GCG CAA
phe thr asn glu gly ala ile leu asn leu lys asn gly leu ala met asp val ala gln
721/241                                751/251
GCA AAT CCA AAG CTC CGC CGA ATA ATC ATC TAT CCT GCC ACA GGA AAA CCA AAT CAA ATG
ala asn pro lys leu arg arg ile ile ile tyr pro ala thr gly lys pro asn gln met
781/261
TGG CTT CCC GTG CCA TGA TAA GGA TCC
trp leu pro val pro STP STP BamHI
```

FIG. 4a and 4b

Nucleotide sequence and deduced amino acid sequence of prepromistletoe-lectin

```
1/1                                        31/11
CAT ATG TAC GAA CGT ATC CGT CTG CGT GTT ACC CAC CAG ACC ACC GGT GAA GAA TAT TTC
NdeI Met tyr glu arg ile arg leu arg val thr his gln thr thr gly glu glu tyr phe
61/21                                      91/31
CGG TTC ATC ACG CTT CTC CGA GAT TAT GTC TCA AGC GGA AGC TTT TCC AAT GAG ATA CCA
arg phe ile thr leu leu arg asp tyr val ser ser gly ser phe ser asn glu ile pro
121/41                                     151/51
CTC TTG CGT CAG TCT ACG ATC CCC GTC TCC GAT GCG CAA AGA TTT GTC TTG GTG GAG CTC
leu leu arg gln ser thr ile pro val ser asp ala gln arg phe val leu val glu leu
181/61                                     211/71
ACC AAC CAG GGG GGA GAC TCG ATC ACG GCC GCC ATC GAC GTT ACC AAT CTG TAC GTC GTG
thr asn gln gly gly asp ser ile thr ala ala ile asp val thr asn leu tyr val val
241/81                                     271/91
GCT TAC CAA GCA GGC GAC CAA TCC TAC TTT TTG CGC GAC GCA CCA CGC GGC GCG GAA ACG
ala tyr gln ala gly asp gln ser tyr phe leu arg asp ala pro arg gly ala glu thr
301/101                                    331/111
CAT CTC TTC ACC GGC ACC ACC CGA TCC TCT CTC CCA TTC AAC GGA AGC TAC CCT GAT CTG
his leu phe thr gly thr thr arg ser ser leu pro phe asn gly ser tyr pro asp leu
361/121                                    391/131
GAG CGA TAC GCC GGA CAT AGG GAC CAG ATC CCT CTC GGT ATA GAC CAA CTC ATT CAA TCC
glu arg tyr ala gly his arg asp gln ile pro leu gly ile asp gln leu ile gln ser
421/141                                    451/151
GTC ACG GCG CTT CGT TTT CCG GGC GGC AGC ACG CGT ACC CAA GCT CGT TCG ATT TTA ATC
val thr ala leu arg phe pro gly gly ser thr arg thr gln ala arg ser ile leu ile
481/161                                    511/171
CTC ATT CAG ATG ATC TCC GAG GCC GCC AGA TTC AAT CCC ATC TTA TGG AGG GCT CGC CAA
leu ile gln met ile ser glu ala ala arg phe asn pro ile leu trp arg ala arg gln
541/181                                    571/191
TAC ATT AAC AGT GGG GCG TCA TTT CTG CCA GAC GTG TAC ATG CTC GAG CTG GAG ACG AGT
tyr ile asn ser gly ala ser phe leu pro asp val tyr met leu glu leu glu thr ser
601/201                                    631/211
TGG GGC CAA CAA TCC ACG CAA GTC CAG CAT TCA ACC GAT GGC GTT TTT AAT AAC CCA ATT
trp gly gln gln ser thr gln val gln his ser thr asp gly val phe asn asn pro ile
661/221                                    691/231
CGG TTG GCT ATA CCC CCC GGT AAC TTC GTG ACG TTG ACC AAT GTT CGC GAC GTG ATC GCC
arg leu ala ile pro pro gly asn phe val thr leu thr asn val arg asp val ile ala
721/241                                    751/251
AGC TTG GCG ATC ATG TTG TTT GTA TGC GGA GAG CGG CCA TCT TAA TAG GGA TCC
ser leu ala ile met leu phe val cys gly glu arg pro ser STP STP BamHI 1/1                                        31/11
CAT ATG GAT GAT GTT ACC TGC AGT GCT TCG GAA CCT ACG GTG CGG ATT GTG GGT CGA AAT
NdeI Met asp asp val thr cys ser ala ser glu pro thr val arg ile val gly arg asn
61/21                                      91/31
GGC ATG TGC GTG GAC GTC CGA GAT GAC GAT TTC CGC GAT GGA AAT CAG ATA CAG TTG TGG
gly met cys val asp val arg asp asp asp phe arg asp gly asn gln ile gln leu trp
121/41                                     151/51
CCC TCC AAG TCC AAC AAT GAT CCG AAT CAG TTG TGG ACG ATC AAA AGG GAT GGA ACC ATT
pro ser lys ser asn asn asp pro asn gln leu trp thr ile lys arg asp gly thr ile
181/61                                     211/71
CGA TCC AAT GGC AGC TGC TTG ACC ACG TAT GGC TAT ACT GCT GGC GTC TAT GTG ATG ATC
arg ser asn gly ser cys leu thr thr tyr gly tyr thr ala gly val tyr val met ile
241/81                                     271/91
TTC GAC TGT AAT ACT GCT GTG CGG GAG GCC ACT CTT TGG CAG ATA TGG GGC AAT GGG ACC
phe asp cys asn thr ala val arg glu ala thr leu trp gln ile trp gly asn gly thr
301/101                                    331/111
ATC ATC AAT CCA AGA TCC AAT CTG GTT TTG GCA GCA TCA TCT GGA ATC AAA GGC ACT ACG
ile ile asn pro arg ser asn leu val leu ala ala ser ser gly ile lys gly thr thr
361/121                                    391/131
CTT ACG GTG CAA ACA CTG GAT TAC ACG TTG GGA CAG GGC TGG CTT GCC GGT AAT GAT ACC
leu thr val gln thr leu asp tyr thr leu gly gln gly trp leu ala gly asn asp thr
421/141                                    451/151
GCC CCA CGC GAG GTG ACC ATA TAT GGG TTC AGG GAC CTT TGC ATG GAA TCA AAT GGA GGG
ala pro arg glu val thr ile tyr gly phe arg asp leu cys met glu ser asn gly gly
481/161                                    511/171
AGT GTG TGG GTG GAG ACG TGC GTG AGT AGC CAA AAG AAC CAA AGA TGG GCT TTG TAC GGG
ser val trp val glu thr cys val ser ser gln lys asn gln arg trp ala leu tyr gly
541/181                                    571/191
GAT GGT TCT ATA CGC CCC AAA CAA AAC CAA GAC CAA TGC CTC ACC TGT GGG AGA GAC TCC
asp gly ser ile arg pro lys gln asn gln asp gln cys leu thr cys gly arg asp ser
601/201                                    631/211
GTT TCA ACA GTA ATC AAT ATA GTT AGC TGC AGC GCT GGA TCG TCT GGG CAG CGA TGG GTG
val ser thr val ile asn ile val ser cys ser ala gly ser ser gly gln arg trp val
661/221                                    691/231
TTT ACC AAT GAA GGG GCC ATT TTG AAT TTA AAG AAT GGG TTG GCC ATG GAT GTG GCG CAA
phe thr asn glu gly ala ile leu asn leu lys asn gly leu ala met asp val ala gln
721/241                                    751/251
GCA AAT CCA AAG CTC CGC CGA ATA ATC ATC TAT CCT GCC ACA GGA AAA CCA AAT CAA ATG
ala asn pro lys leu arg arg ile ile ile tyr pro ala thr gly lys pro asn gln met
781/261
TGG CTT CCC GTG CCA TGA TAA GGA TCC
trp leu pro val pro STP STP BamHI
```

Sequence as derived from cloned gene fragments "h" (nucleotide 1-204), "f" (nucleotide 205-909), "e" (nucleotide 910-957), "g" (nucleotide 958-1746) and "i" (nucleotide 1747-1923)

FIG. 4c

Expression of rMLA and rMLB
a: Expression of rMLA-chain
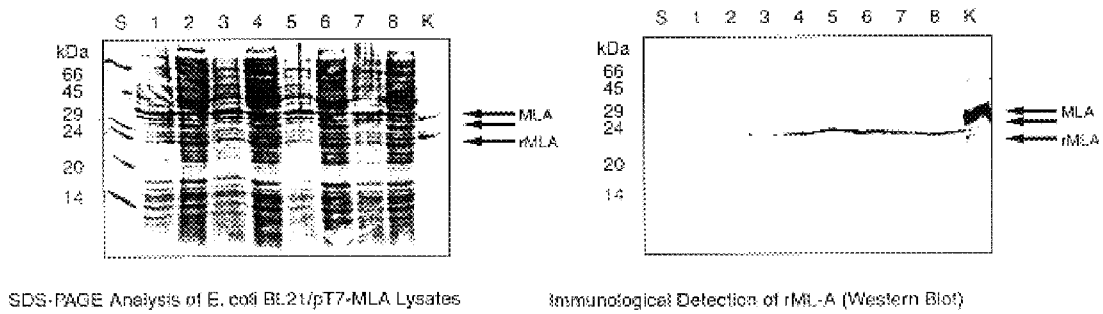
SDS-PAGE Analysis of E. coli BL21/pT7-MLA Lysates     Immunological Detection of rML-A (Western Blot)
b: Expression of rMLB-chain
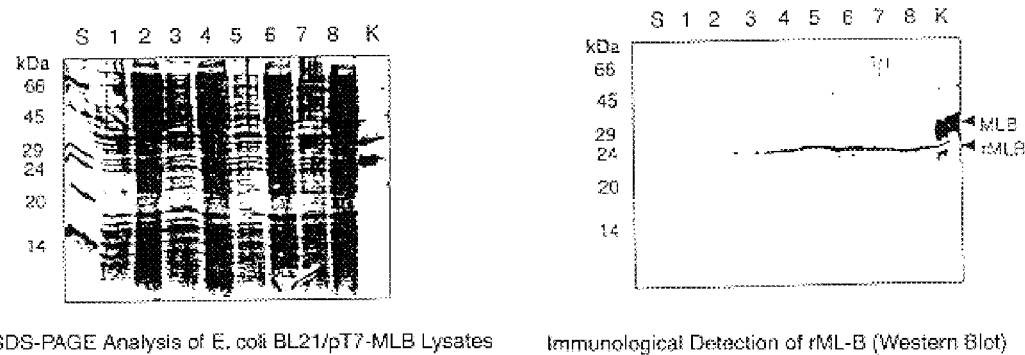
SDS-PAGE Analysis of E. coli BL21/pT7-MLB Lysates     Immunological Detection of rML-B (Western Blot)
FIG. 7

Immunostimulating effect of recombinant mistletoe lectin in the PBMC model
a: Induction of secretion of TNF-α
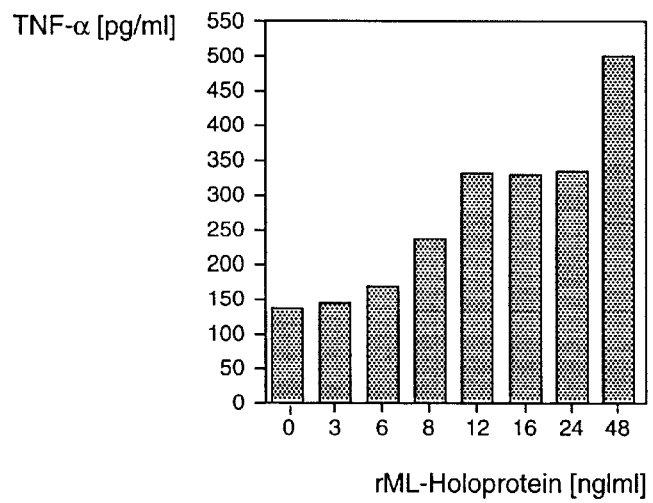
b: Induction of secretion of INF-γ
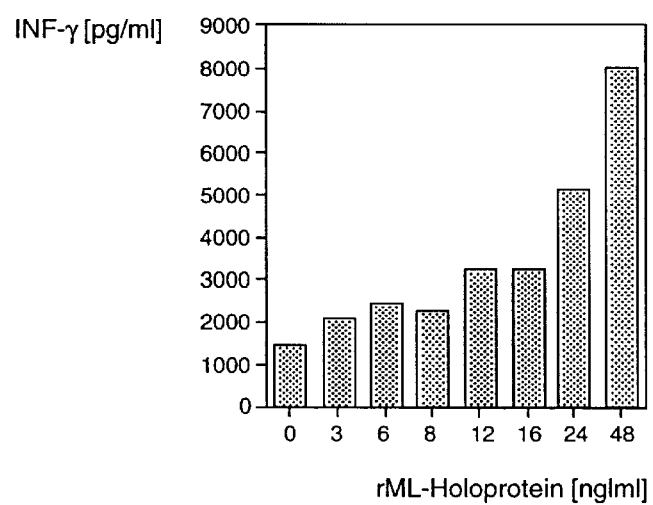
FIG. 13

Immunostimulating effect of recombinant mistletoe lectin in skin²-ZK1200 model a: Induction of secretion of IL-1α b: Induction of secretion of IL-6

FIG. 14

SEQUENCE LISTING

<160> NUMBER OF SEQ ID NOS: 56

<210> SEQ ID NO 1
<211> LENGTH: 32
<212> TYPE: DNA
<213> ORGANISM: Spodoptera frugiperda
<220> FEATURE:
<221> NAME/KEY: variation
<222> LOCATION: (1)..(32)
<223> OTHER INFORMATION: N stands for Inosin

<400> SEQUENCE: 1
gaattccayc aracnacngg ngargartay tt                                         32

<210> SEQ ID NO 2
<211> LENGTH: 21
<212> TYPE: DNA
<213> ORGANISM: Spodoptera frugiperda
<220> FEATURE:
<221> NAME/KEY: variation
<222> LOCATION: (1)..(21)
<223> OTHER INFORMATION: Y stands for C or T
<220> FEATURE:
<221> NAME/KEY: variation
<222> LOCATION: (1)..(21)
<223> OTHER INFORMATION: N stands for A or C or G or T
<220> FEATURE:
<221> NAME/KEY: variation
<222> LOCATION: (1)..(21)
<223> OTHER INFORMATION: W stands for A or T
<220> FEATURE:
<221> NAME/KEY: variation
<222> LOCATION: (1)..(21)
<223> OTHER INFORMATION: S stands for G or C
<220> FEATURE:
<221> NAME/KEY: variation
<222> LOCATION: (1)..(21)

<400> SEQUENCE: 2
gaygaygtna cnwsnwsngc n                                                     21

<210> SEQ ID NO 3
<211> LENGTH: 18
<212> TYPE: DNA
<213> ORGANISM: Spodoptera frugiperda
<220> FEATURE:
<221> NAME/KEY: variation
<222> LOCATION: (1)..(18)
<223> OTHER INFORMATION: R stands for A or G
<220> FEATURE:
<221> NAME/KEY: variation
<222> LOCATION: (1)..(18)
<223> OTHER INFORMATION: N stands for A or C or G or T
<220> FEATURE:
<221> NAME/KEY: variation
<222> LOCATION: (1)..(18)
<223> OTHER INFORMATION: M stands for A or C
<220> FEATURE:
<221> NAME/KEY: variation
<222> LOCATION: (1)..(18)
<223> OTHER INFORMATION: H stands for A or C or T

<400> SEQUENCE: 3
garccnacng tnmgnath                                                         18

<210> SEQ ID NO 4
<211> LENGTH: 18
<212> TYPE: DNA
<213> ORGANISM: Spodoptera frugiperda
<220> FEATURE:

```
<221> NAME/KEY: variation
<222> LOCATION: (1)..(18)
<223> OTHER INFORMATION: Y stands for C or T
<220> FEATURE:
<221> NAME/KEY: variation
<222> LOCATION: (1)..(18)
<223> OTHER INFORMATION: N stands for A or C or G or T
<220> FEATURE:
<221> NAME/KEY: variation
<222> LOCATION: (1)..(18)
<223> OTHER INFORMATION: M stands for A or C

<400> SEQUENCE: 4
gtnggnmgna ayggnatg                                                 18

<210> SEQ ID NO 5
<211> LENGTH: 47
<212> TYPE: PRT
<213> ORGANISM: Triticum aestivum

<400> SEQUENCE: 5

Ala Leu Tyr Gly Arg Thr Lys Ala Asp Lys Thr Ser Gly Pro Lys Gln
 1               5                  10                  15

Gln Gln Ala Arg Glu Ala Val Thr Thr Leu Leu Leu Met Val His Glu
            20                  25                  30

Ala Thr Arg Phe Gln Thr Val Ser Gly Phe Val Ala Gly Val Leu
        35                  40                  45

<210> SEQ ID NO 6
<211> LENGTH: 47
<212> TYPE: PRT
<213> ORGANISM: Hordeum vulgare

<400> SEQUENCE: 6

Ala Leu His Gly Arg Thr Lys Ala Asp Lys Ala Ser Gly Pro Lys Gln
 1               5                  10                  15

Gln Gln Ala Arg Glu Ala Val Thr Thr Leu Leu Leu Met Val Asn Glu
            20                  25                  30

Ala Thr Arg Phe Gln Thr Val Ser Gly Phe Val Ala Gly Leu Leu
        35                  40                  45

<210> SEQ ID NO 7
<211> LENGTH: 45
<212> TYPE: PRT
<213> ORGANISM: Trichosanthes kirilowii

<400> SEQUENCE: 7

Ala Leu Asp Ser Ala Ile Thr Thr Leu Phe Tyr Tyr Asn Ala Asn Ser
 1               5                  10                  15

Ala Ala Ser Ala Leu Met Val Leu Ile Gln Ser Thr Ser Glu Ala Ala
            20                  25                  30

Arg Tyr Lys Phe Ile Glu Gln Gln Ile Gly Lys Arg Val
        35                  40                  45

<210> SEQ ID NO 8
<211> LENGTH: 45
<212> TYPE: PRT
<213> ORGANISM: Momordica charantia

<400> SEQUENCE: 8

Ala Leu Asp Ser Ala Ile Ser Thr Leu Leu His Tyr Asp Ser Thr Ala
 1               5                  10                  15

Ala Ala Gly Ala Leu Leu Val Leu Ile Gln Thr Thr Ala Glu Ala Ala
```

-continued

```
            20                  25                  30

Arg Phe Lys Tyr Ile Glu Gln Gln Ile Gln Glu Arg Ala
        35                  40                  45

<210> SEQ ID NO 9
<211> LENGTH: 45
<212> TYPE: PRT
<213> ORGANISM: Luffa cylindrica

<400> SEQUENCE: 9

Ala Leu Asp Ser Ala Ile Thr Thr Leu Phe His Tyr Asp Ser Thr Ala
  1               5                  10                  15

Ala Ala Ala Ala Phe Leu Val Ile Ile Gln Thr Thr Ala Glu Ala Ser
            20                  25                  30

Arg Phe Lys Tyr Ile Glu Gly Gln Ile Ile Glu Arg Ile
        35                  40                  45

<210> SEQ ID NO 10
<211> LENGTH: 45
<212> TYPE: PRT
<213> ORGANISM: Luffa cylindrica

<400> SEQUENCE: 10

Ala Phe Asp Ser Ala Ile Thr Ser Leu Phe His Tyr Asp Ser Thr Ala
  1               5                  10                  15

Ala Ala Gly Ala Phe Leu Val Ile Ile Gln Thr Thr Ala Glu Ala Ser
            20                  25                  30

Arg Phe Lys Tyr Ile Glu Gly Gln Ile Ile Glu Arg Ile
        35                  40                  45

<210> SEQ ID NO 11
<211> LENGTH: 45
<212> TYPE: PRT
<213> ORGANISM: Momordica balsamina

<400> SEQUENCE: 11

Ala Leu Ser Ser Ala Ile Thr Thr Leu Phe Tyr Tyr Asn Ala Gln Ser
  1               5                  10                  15

Ala Pro Ser Ala Leu Leu Val Leu Ile Gln Thr Thr Ala Glu Ala Ala
            20                  25                  30

Arg Phe Lys Tyr Ile Glu Arg His Val Ala Lys Tyr Val
        35                  40                  45

<210> SEQ ID NO 12
<211> LENGTH: 50
<212> TYPE: PRT
<213> ORGANISM: Ricinus communis

<400> SEQUENCE: 12

Pro Leu Glu Glu Ala Ile Ser Ala Leu Tyr Tyr Tyr Ser Thr Gly Gly
  1               5                  10                  15

Thr Gln Leu Pro Thr Leu Ala Arg Ser Phe Ile Ile Cys Ile Gln Met
            20                  25                  30

Ile Ser Glu Ala Ala Arg Phe Gln Tyr Ile Glu Gly Glu Met Arg Thr
        35                  40                  45

Arg Ile
    50

<210> SEQ ID NO 13
<211> LENGTH: 49
```

```
<212> TYPE: PRT
<213> ORGANISM: Ricinus communis

<400> SEQUENCE: 13

Pro Leu Glu Asp Ala Ile Ser Ala Leu Tyr Tyr Tyr Ser Thr Cys Gly
 1               5                  10                  15

Gln Ile Pro Thr Leu Ala Arg Ser Phe Met Val Cys Ile Gln Met Ile
                20                  25                  30

Ser Glu Ala Ala Arg Phe Gln Tyr Ile Glu Gly Glu Met Arg Thr Arg
            35                  40                  45

Ile

<210> SEQ ID NO 14
<211> LENGTH: 47
<212> TYPE: PRT
<213> ORGANISM: Abrus precatorius

<400> SEQUENCE: 14

Ala Leu Thr His Ala Ile Ser Phe Leu Arg Ser Gly Ala Ser Asn Asp
 1               5                  10                  15

Glu Glu Lys Ala Arg Thr Leu Ile Val Ile Gln Met Ala Ser Glu
                20                  25                  30

Ala Ala Arg Tyr Arg Tyr Ile Ser Asn Arg Val Gly Val Ser Ile
            35                  40                  45

<210> SEQ ID NO 15
<211> LENGTH: 47
<212> TYPE: PRT
<213> ORGANISM: Mirabilis jalapa

<400> SEQUENCE: 15

Arg Leu Glu Asn Ser Ile Val Asn Ile Tyr Gly Lys Ala Gly Asp Val
 1               5                  10                  15

Lys Lys Gln Ala Lys Phe Phe Leu Leu Ala Ile Gln Met Val Ser Glu
                20                  25                  30

Ala Ala Arg Phe Lys Tyr Ile Ser Asp Lys Ile Pro Ser Glu Lys
            35                  40                  45

<210> SEQ ID NO 16
<211> LENGTH: 47
<212> TYPE: PRT
<213> ORGANISM: Saponaria officinalis

<400> SEQUENCE: 16

Leu Leu Leu Thr Phe Met Glu Ala Val Asn Lys Lys Ala Arg Val Val
 1               5                  10                  15

Lys Asn Glu Ala Arg Phe Leu Leu Ile Ala Ile Gln Met Thr Ala Glu
                20                  25                  30

Val Ala Arg Phe Arg Tyr Ile Gln Asn Leu Val Thr Lys Asn Phe
            35                  40                  45

<210> SEQ ID NO 17
<211> LENGTH: 47
<212> TYPE: PRT
<213> ORGANISM: Saponaria officinalis

<400> SEQUENCE: 17

Leu Leu Ser Thr Ser Met Glu Ala Val Asn Lys Lys Ala Arg Val Val
 1               5                  10                  15

Lys Asp Glu Ala Arg Phe Leu Leu Ile Ala Ile Gln Met Thr Ala Glu
```

```
              20                  25                  30

Ala Ala Arg Phe Arg Tyr Ile Gln Asn Leu Val Ile Lys Asn Phe
            35                  40                  45

<210> SEQ ID NO 18
<211> LENGTH: 47
<212> TYPE: PRT
<213> ORGANISM: Saponaria officinalis

<400> SEQUENCE: 18

Leu Leu Ser Thr Leu Met Asp Ala Val Asn Lys Lys Ala Arg Val Val
  1               5                  10                  15

Lys Asn Glu Ala Arg Phe Leu Leu Ile Ala Ile Gln Met Thr Ala Glu
             20                  25                  30

Ala Ala Arg Phe Arg Tyr Ile Gln Asn Leu Val Thr Lys Asn Phe
            35                  40                  45

<210> SEQ ID NO 19
<211> LENGTH: 47
<212> TYPE: PRT
<213> ORGANISM: Dianthus caryophyllus

<400> SEQUENCE: 19

Leu Leu Ile Thr Met Ile Asp Gly Val Asn Lys Val Arg Val Val
  1               5                  10                  15

Lys Asp Glu Ala Arg Phe Leu Leu Ile Ala Ile Gln Met Thr Ala Glu
             20                  25                  30

Ala Ala Arg Phe Arg Tyr Ile Gln Asn Leu Val Thr Lys Asn Phe
            35                  40                  45

<210> SEQ ID NO 20
<211> LENGTH: 48
<212> TYPE: PRT
<213> ORGANISM: Phytolacca americana

<400> SEQUENCE: 20

Ile Leu Ser Ser Asp Ile Gly Lys Ile Ser Cys Gln Gly Ser Phe Thr
  1               5                  10                  15

Glu Lys Ile Glu Ala Lys Phe Leu Leu Val Ala Ile Gln Met Val Ser
             20                  25                  30

Glu Ala Ala Arg Phe Lys Tyr Ile Glu Asn Gln Val Lys Thr Asn Phe
            35                  40                  45

<210> SEQ ID NO 21
<211> LENGTH: 48
<212> TYPE: PRT
<213> ORGANISM: Phytolacca americana

<400> SEQUENCE: 21

Ile Leu Asp Ser Asn Ile Gly Lys Ile Ser Gly Val Met Ser Phe Thr
  1               5                  10                  15

Glu Lys Thr Glu Ala Glu Phe Leu Leu Val Ala Ile Gln Met Val Ser
             20                  25                  30

Glu Ala Ala Arg Phe Lys Tyr Ile Glu Asn Gln Val Lys Thr Asn Phe
            35                  40                  45

<210> SEQ ID NO 22
<211> LENGTH: 48
<212> TYPE: PRT
<213> ORGANISM: Phytolacca americana
```

-continued

```
<400> SEQUENCE: 22

Ile Leu Asn Ser Gly Ile Gly Lys Ile Tyr Gly Val Asp Ser Phe Thr
 1               5                  10                  15

Glu Lys Thr Glu Ala Glu Phe Leu Leu Val Ala Ile Gln Met Val Ser
             20                  25                  30

Glu Ala Ala Arg Phe Lys Tyr Ile Glu Asn Gln Val Lys Thr Asn Phe
         35                  40                  45

<210> SEQ ID NO 23
<211> LENGTH: 21
<212> TYPE: PRT
<213> ORGANISM: Ricinus communis

<400> SEQUENCE: 23

Ser Phe Ile Ile Cys Ile Gln Met Ile Ser Glu Ala Ala Arg Phe Gln
 1               5                  10                  15

Tyr Ile Glu Gly Glu
             20

<210> SEQ ID NO 24
<211> LENGTH: 21
<212> TYPE: PRT
<213> ORGANISM: Abrus precatorius

<400> SEQUENCE: 24

Thr Leu Ile Val Ile Ile Gln Met Ala Ser Glu Ala Ala Arg Tyr Arg
 1               5                  10                  15

Tyr Ile Ser Asn Arg
             20

<210> SEQ ID NO 25
<211> LENGTH: 21
<212> TYPE: PRT
<213> ORGANISM: Mirabilis jalapa

<400> SEQUENCE: 25

Phe Leu Leu Ile Ala Ile Gln Met Val Ser Glu Ala Ala Arg Phe Lys
 1               5                  10                  15

Tyr Ile Ser Asp Lys
             20

<210> SEQ ID NO 26
<211> LENGTH: 21
<212> TYPE: PRT
<213> ORGANISM: Saponaria officinalis

<400> SEQUENCE: 26

Phe Leu Leu Ile Ala Ile Gln Met Thr Ala Glu Ala Ala Arg Phe Arg
 1               5                  10                  15

Tyr Ile Gln Asn Leu
             20

<210> SEQ ID NO 27
<211> LENGTH: 21
<212> TYPE: PRT
<213> ORGANISM: Phytolacca americana

<400> SEQUENCE: 27

Phe Leu Leu Val Ala Ile Gln Met Val Ser Glu Ala Ala Arg Phe Lys
 1               5                  10                  15

Tyr Ile Glu Asn Gln
```

```
<210> SEQ ID NO 28
<211> LENGTH: 30
<212> TYPE: DNA
<213> ORGANISM: Spodoptera frugiperda
<220> FEATURE:
<221> NAME/KEY: variation
<222> LOCATION: (1)..(30)
<223> OTHER INFORMATION: Y stands for C or T
<220> FEATURE:
<221> NAME/KEY: variation
<222> LOCATION: (1)..(30)
<223> OTHER INFORMATION: R stands for A or G
<220> FEATURE:
<221> NAME/KEY: variation
<222> LOCATION: (1)..(30)
<223> OTHER INFORMATION: N stands for A or C or G or T
<220> FEATURE:
<221> NAME/KEY: variation
<222> LOCATION: (1)..(30)
<223> OTHER INFORMATION: W stands for A or T
<220> FEATURE:
<221> NAME/KEY: variation
<222> LOCATION: (1)..(30)
<223> OTHER INFORMATION: S stands for G or C
<220> FEATURE:
<221> NAME/KEY: variation
<222> LOCATION: (1)..(30)
<223> OTHER INFORMATION: M stands for A or C
<220> FEATURE:
<221> NAME/KEY: variation
<222> LOCATION: (1)..(30)
<223> OTHER INFORMATION: H stands for A or C or T

<400> SEQUENCE: 28
athcaratgr ynwsngargc ngcnmgntty                               30

<210> SEQ ID NO 29
<211> LENGTH: 38
<212> TYPE: DNA
<213> ORGANISM: Spodoptera frugiperda
<220> FEATURE:
<221> NAME/KEY: variation
<222> LOCATION: (1)..(38)
<223> OTHER INFORMATION: B stands for Inosine
<220> FEATURE:
<221> NAME/KEY: variation
<222> LOCATION: (1)..(38)
<223> OTHER INFORMATION: Y stands for C or T
<220> FEATURE:
<221> NAME/KEY: variation
<222> LOCATION: (1)..(38)
<223> OTHER INFORMATION: R stands for A or G
<220> FEATURE:
<221> NAME/KEY: variation
<222> LOCATION: (1)..(38)
<223> OTHER INFORMATION: S stands for G or C
<220> FEATURE:
<221> NAME/KEY: variation
<222> LOCATION: (1)..(38)

<400> SEQUENCE: 29
atggatccra abbbbgcbgc ytcbbbbayc atstgbat                      38

<210> SEQ ID NO 30
<211> LENGTH: 774
<212> TYPE: DNA
<213> ORGANISM: Viscum album

<400> SEQUENCE: 30
catatgtacg aacgtatccg tctgcgtgtt acccaccaga ccaccggtga agaatatttc    60
```

-continued

```
cggttcatca cgcttctccg agattatgtc tcaagcggaa gcttttccaa tgagatacca      120
ctcttgcgtc agtctacgat ccccgtctcc gatgcgcaaa gatttgtctt ggtggagctc      180
accaaccagg ggggagactc gatcacggcc gccatcgacg ttaccaatct gtacgtcgtg      240
gcttaccaag caggcgacca atcctacttt tgcgcgacg caccacgcgg cgcggaaacg       300
catctcttca ccggcaccac ccgatcctct ctcccattca acggaagcta ccctgatctg      360
gagcgatacg ccggacatag ggaccagatc cctctcggta tagaccaact cattcaatcc      420
gtcacggcgc ttcgttttcc gggcggcagc acgcgtaccc aagctcgttc gattttaatc      480
ctcattcaga tgatctccga ggccgccaga ttcaatccca tcttatggag ggctcgccaa      540
tacattaaca gtggggcgtc atttctgcca gacgtgtaca tgctggagct ggagacgagt      600
tggggccaac aatccacgca agtccagcat tcaaccgatg gcgtttttaa taacccaatt      660
cggttggcta ccccccgg taacttcgtg acgttgacca atgttcgcga cgtgatcgcc        720
agcttggcga tcatgttgtt tgtatgcgga gagcggccat cttaataggg atcc            774
```

<210> SEQ ID NO 31
<211> LENGTH: 253
<212> TYPE: PRT
<213> ORGANISM: Viscum album
<400> SEQUENCE: 31

```
Met Tyr Glu Arg Ile Arg Leu Arg Val Thr His Gln Thr Thr Gly Glu
  1               5                  10                  15

Glu Tyr Phe Arg Phe Ile Thr Leu Leu Arg Asp Tyr Val Ser Ser Gly
                 20                  25                  30

Ser Phe Ser Asn Glu Ile Pro Leu Leu Arg Gln Ser Thr Ile Pro Val
         35                  40                  45

Ser Asp Ala Gln Arg Phe Val Leu Val Glu Leu Thr Asn Gln Gly Gly
     50                  55                  60

Asp Ser Ile Thr Ala Ala Ile Asp Val Thr Asn Leu Tyr Val Val Ala
 65                  70                  75                  80

Tyr Gln Ala Gly Asp Gln Ser Tyr Phe Leu Arg Asp Ala Pro Arg Gly
                 85                  90                  95

Ala Glu Thr His Leu Phe Thr Gly Thr Thr Arg Ser Ser Leu Pro Phe
            100                 105                 110

Asn Gly Ser Tyr Pro Asp Leu Glu Arg Tyr Ala Gly His Arg Asp Gln
        115                 120                 125

Ile Pro Leu Gly Ile Asp Gln Leu Ile Gln Ser Val Thr Ala Leu Arg
    130                 135                 140

Phe Pro Gly Gly Ser Thr Arg Thr Gln Ala Arg Ser Ile Leu Ile Leu
145                 150                 155                 160

Ile Gln Met Ile Ser Glu Ala Ala Arg Phe Asn Pro Ile Leu Trp Arg
                165                 170                 175

Ala Arg Gln Tyr Ile Asn Ser Gly Ala Ser Phe Leu Pro Asp Val Tyr
            180                 185                 190

Met Leu Glu Leu Glu Thr Ser Trp Gly Gln Ser Thr Gln Val Gln
        195                 200                 205

His Ser Thr Asp Gly Val Phe Asn Asn Pro Ile Arg Leu Ala Ile Pro
    210                 215                 220

Pro Gly Asn Phe Val Thr Leu Thr Asn Val Arg Asp Val Ile Ala Ser
225                 230                 235                 240

Leu Ala Ile Met Leu Phe Val Cys Gly Glu Arg Pro Ser
                245                 250
```

-continued

<210> SEQ ID NO 32
<211> LENGTH: 807
<212> TYPE: DNA
<213> ORGANISM: Viscum album

<400> SEQUENCE: 32

```
catatggatg atgttacctg cagtgcttcg gaacctacgg tgcggattgt gggtcgaaat     60
ggcatgtgcg tggacgtccg agatgacgat ttccgcgatg gaaatcagat acagttgtgg    120
ccctccaagt ccaacaatga tccgaatcag ttgtggacga tcaaaaggga tggaaccatt    180
cgatccaatg gcagctgctt gaccacgtat ggctatactg ctggcgtcta tgtgatgatc    240
ttcgactgta atactgctgt gcgggaggcc actctttggc agatatgggg caatgggacc    300
atcatcaatc caagatccaa tctggttttg gcagcatcat ctggaatcaa aggcactacg    360
cttacggtgc aaacactgga ttacacgttg ggacagggct ggcttgccgg taatgatacc    420
gccccacgcg aggtgaccat atatgggttc agggaccttt gcatggaatc aaatggaggg    480
agtgtgtggg tggagacgtg cgtgagtagc caaaagaacc aaagatgggc tttgtacggg    540
gatggttcta tacgccccaa acaaaaccaa gaccaatgcc tcacctgtgg gagagactcc    600
gtttcaacag taatcaatat agttagctgc agcgctggat cgtctgggca gcgatgggtg    660
tttaccaatg aaggggccat tttgaattta aagaatgggt tggccatgga tgtggcgcaa    720
gcaaatccaa agctccgccg aataatcatc tatcctgcca caggaaaacc aaatcaaatg    780
tggcttcccg tgccatgata aggatcc                                         807
```

<210> SEQ ID NO 33
<211> LENGTH: 264
<212> TYPE: PRT
<213> ORGANISM: Viscum album

<400> SEQUENCE: 33

```
Met Asp Asp Val Thr Cys Ser Ala Ser Glu Pro Thr Val Arg Ile Val
  1               5                  10                  15

Gly Arg Asn Gly Met Cys Val Asp Val Arg Asp Asp Asp Phe Arg Asp
             20                  25                  30

Gly Asn Gln Ile Gln Leu Trp Pro Ser Lys Ser Asn Asn Asp Pro Asn
         35                  40                  45

Gln Leu Trp Thr Ile Lys Arg Asp Gly Thr Ile Arg Ser Asn Gly Ser
     50                  55                  60

Cys Leu Thr Thr Tyr Gly Tyr Thr Ala Gly Val Tyr Val Met Ile Phe
 65                  70                  75                  80

Asp Cys Asn Thr Ala Val Arg Glu Ala Thr Leu Trp Gln Ile Trp Gly
                 85                  90                  95

Asn Gly Thr Ile Ile Asn Pro Arg Ser Asn Leu Val Leu Ala Ala Ser
            100                 105                 110

Ser Gly Ile Lys Gly Thr Thr Leu Thr Val Gln Thr Leu Asp Tyr Thr
        115                 120                 125

Leu Gly Gln Gly Trp Leu Ala Gly Asn Asp Thr Ala Pro Arg Glu Val
    130                 135                 140

Thr Ile Tyr Gly Phe Arg Asp Leu Cys Met Glu Ser Asn Gly Gly Ser
145                 150                 155                 160

Val Trp Val Glu Thr Cys Val Ser Ser Gln Lys Asn Gln Arg Trp Ala
                165                 170                 175

Leu Tyr Gly Asp Gly Ser Ile Arg Pro Lys Gln Asn Gln Asp Gln Cys
```

```
                    180                 185                 190
Leu Thr Cys Gly Arg Asp Ser Val Ser Thr Val Ile Asn Ile Val Ser
            195                 200                 205
Cys Ser Ala Gly Ser Ser Gly Gln Arg Trp Val Phe Thr Asn Glu Gly
        210                 215                 220
Ala Ile Leu Asn Leu Lys Asn Gly Leu Ala Met Asp Val Ala Gln Ala
225                 230                 235                 240
Asn Pro Lys Leu Arg Arg Ile Ile Ile Tyr Pro Ala Thr Gly Lys Pro
                245                 250                 255
Asn Gln Met Trp Leu Pro Val Pro
            260

<210> SEQ ID NO 34
<211> LENGTH: 1923
<212> TYPE: DNA
<213> ORGANISM: Viscum album

<400> SEQUENCE: 34
```

| | | | | | |
|---|---|---|---|---|---|
| ttttatctcc | tgccatcttc | catcggggag | tcgccgtgac | accattcagg | aacaatgaat | 60 |
| gcggttatgg | actcaagaag | ggcatgggct | tcgtgttttt | taatgctggg | cctagttttt | 120 |
| ggtgcgacgg | tcaaagcgga | aaccaaattc | agctacgaga | ggctaagact | cagagttacg | 180 |
| catcaaacca | cgggcgacga | atatttccgg | ttcatcacgc | ttctccgaga | ttatgtctca | 240 |
| agcggaagct | tttccaatga | gataccactc | ttgcgtcagt | ctacgatccc | cgtctccgat | 300 |
| gcgcaaagat | ttgtcttggt | ggagctcacc | aaccaggggg | gagactcgat | cacggccgcc | 360 |
| atcgacgtta | ccaatctgta | cgtcgtggct | taccaagcag | gcgaccaatc | ctactttttg | 420 |
| cgcgacgcac | cacgcggcgc | ggaaacgcat | ctcttcaccg | gcaccacccg | atcctctctc | 480 |
| ccattcaacg | gaagctaccc | tgatctggag | cgatacgccg | gacatagggg | aacagatccct | 540 |
| ctcggtatag | accaactcat | tcaatccgtc | acggcgcttc | gttttccggg | cggcagcacg | 600 |
| cgtacccaag | ctcgttcgat | tttaatcctc | attcagatga | tctccgaggc | cgccagattc | 660 |
| aatcccatct | tatggagggc | tcgccaatac | attaacagtg | gggcgtcatt | tctgccagac | 720 |
| gtgtacatgc | tggagctgga | gacgagttgg | ggccaacaat | ccacgcaagt | ccagcattca | 780 |
| accgatggcg | ttttttaataa | cccaattcgg | ttggctatac | cccccggtaa | cttcgtgacg | 840 |
| ttgaccaatg | ttcgcgacgt | gatcgccagc | ttggcgatca | tgttgtttgt | atgcggagag | 900 |
| cggccatctt | cctctgaggt | gcgctattgg | ccgctggtca | tacgacccgt | gatagccgat | 960 |
| gatgttacct | gcagtgcttc | ggaacctacg | gtgcggattg | tgggtcgaaa | tggcatgtgc | 1020 |
| gtggacgtcc | gagatgacga | tttccgcgat | ggaaatcaga | tacagttgtg | gccctccaag | 1080 |
| tccaacaatg | atccgaatca | gttgtggacg | atcaaaaggg | atggaaccat | tcgatccaat | 1140 |
| ggcagctgct | tgaccacgta | tggctatact | gctggcgtct | atgtgatgat | cttcgactgt | 1200 |
| aatactgctg | tgcgggaggc | cactctttgg | cagatatggg | gcaatgggac | catcatcaat | 1260 |
| ccaagatcca | atctggtttt | ggcagcatca | tctggaatca | aaggcactac | gcttacggtg | 1320 |
| caaacactgg | attacacgtt | gggacagggc | tggcttgccg | gtaatgatac | cgccccacgc | 1380 |
| gaggtgacca | tatatgggtt | cagggaccctt | tgcatggaat | caaatggagg | gagtgtgtgg | 1440 |
| gtggagacgt | gcgtgagtag | ccaaaagaac | caaagatggg | ctttgtacgg | ggatggttct | 1500 |
| atacgccccca | aacaaaacca | agaccaatgc | ctcacctgtg | ggagagactc | cgtttcaaca | 1560 |
| gtaatcaata | tagttagctg | cagcgctgga | tcgtctgggc | agcgatgggt | gtttaccaat | 1620 |

-continued

```
gaaggggcca ttttgaattt aaagaatggg ttggccatgg atgtggcgca agcaaatcca   1680
aagctccgcc gaataatcat ctatcctgcc acaggaaaac caaatcaaat gtggcttccc   1740
gtgccatgat ttaggttcat ggctcgaaga ttgcttgcat gcgaccatcc tttctatttt   1800
ctcttttcta cctttgaaa taatgtctgt gaataatgtg gcacgttgag cccgccgaa   1860 agaagcctta gccaccttgt gtttgagaat aaatgagtta atgcaagcaa tcaacttctc   1920
ctt                                                                  1923
```

<210> SEQ ID NO 35
<211> LENGTH: 564
<212> TYPE: PRT
<213> ORGANISM: Viscum album
<400> SEQUENCE: 35

```
Met Asn Ala Val Met Asp Ser Arg Arg Ala Trp Ala Ser Cys Phe Leu
 1               5                  10                  15

Met Leu Gly Leu Val Phe Gly Ala Thr Val Lys Ala Glu Thr Lys Phe
            20                  25                  30

Ser Tyr Glu Arg Leu Arg Leu Arg Val Thr His Gln Thr Thr Gly Asp
        35                  40                  45

Glu Tyr Phe Arg Phe Ile Thr Leu Leu Arg Asp Tyr Val Ser Ser Gly
    50                  55                  60

Ser Phe Ser Asn Glu Ile Pro Leu Leu Arg Gln Ser Thr Ile Pro Val
65                  70                  75                  80

Ser Asp Ala Gln Arg Phe Val Leu Val Glu Leu Thr Asn Gln Gly Gly
                85                  90                  95

Asp Ser Ile Thr Ala Ala Ile Asp Val Thr Asn Leu Tyr Val Val Ala
            100                 105                 110

Tyr Gln Ala Gly Asp Gln Ser Tyr Phe Leu Arg Asp Ala Pro Arg Gly
        115                 120                 125

Ala Glu Thr His Leu Phe Thr Gly Thr Thr Arg Ser Ser Leu Pro Phe
    130                 135                 140

Asn Gly Ser Tyr Pro Asp Leu Glu Arg Tyr Ala Gly His Arg Asp Gln
145                 150                 155                 160

Ile Pro Leu Gly Ile Asp Gln Leu Ile Gln Ser Val Thr Ala Leu Arg
                165                 170                 175

Phe Pro Gly Gly Ser Thr Arg Thr Gln Ala Arg Ser Ile Leu Ile Leu
            180                 185                 190

Ile Gln Met Ile Ser Glu Ala Ala Arg Phe Asn Pro Ile Leu Trp Arg
        195                 200                 205

Ala Arg Gln Tyr Ile Asn Ser Gly Ala Ser Phe Leu Pro Asp Val Tyr
    210                 215                 220

Met Leu Glu Leu Glu Thr Ser Trp Gly Gln Gln Ser Thr Gln Val Gln
225                 230                 235                 240

His Ser Thr Asp Gly Val Phe Asn Asn Pro Ile Arg Leu Ala Ile Pro
                245                 250                 255

Pro Gly Asn Phe Val Thr Leu Thr Asn Val Arg Asp Val Ile Ala Ser
            260                 265                 270

Leu Ala Ile Met Leu Phe Val Cys Gly Glu Arg Pro Ser Ser Ser Glu
        275                 280                 285

Val Arg Tyr Trp Pro Leu Val Ile Arg Pro Val Ile Ala Asp Asp Val
    290                 295                 300

Thr Cys Ser Ala Ser Glu Pro Thr Val Arg Ile Val Gly Arg Asn Gly
305                 310                 315                 320
```

Met Cys Val Asp Val Arg Asp Asp Phe Arg Asp Gly Asn Gln Ile
             325                 330                 335

Gln Leu Trp Pro Ser Lys Ser Asn Asn Asp Pro Asn Gln Leu Trp Thr
             340                 345                 350

Ile Lys Arg Asp Gly Thr Ile Arg Ser Asn Gly Ser Cys Leu Thr Thr
             355                 360                 365

Tyr Gly Tyr Thr Ala Gly Val Tyr Val Met Ile Phe Asp Cys Asn Thr
             370                 375                 380

Ala Val Arg Glu Ala Thr Leu Trp Gln Ile Trp Gly Asn Gly Thr Ile
385                  390                 395                 400

Ile Asn Pro Arg Ser Asn Leu Val Leu Ala Ala Ser Ser Gly Ile Lys
             405                 410                 415

Gly Thr Thr Leu Thr Val Gln Thr Leu Asp Tyr Thr Leu Gly Gln Gly
             420                 425                 430

Trp Leu Ala Gly Asn Asp Thr Ala Pro Arg Glu Val Thr Ile Tyr Gly
             435                 440                 445

Phe Arg Asp Leu Cys Met Glu Ser Asn Gly Gly Ser Val Trp Val Glu
             450                 455                 460

Thr Cys Val Ser Ser Gln Lys Asn Gln Arg Trp Ala Leu Tyr Gly Asp
465                  470                 475                 480

Gly Ser Ile Arg Pro Lys Gln Asn Gln Asp Gln Cys Leu Thr Cys Gly
             485                 490                 495

Arg Asp Ser Val Ser Thr Val Ile Asn Ile Val Ser Cys Ser Ala Gly
             500                 505                 510

Ser Ser Gly Gln Arg Trp Val Phe Thr Asn Glu Gly Ala Ile Leu Asn
             515                 520                 525

Leu Lys Asn Gly Leu Ala Met Asp Val Ala Gln Ala Asn Pro Lys Leu
             530                 535                 540

Arg Arg Ile Ile Ile Tyr Pro Ala Thr Gly Lys Pro Asn Gln Met Trp
545                  550                 555                 560

Leu Pro Val Pro

<210> SEQ ID NO 36
<211> LENGTH: 204
<212> TYPE: DNA
<213> ORGANISM: Viscum album

<400> SEQUENCE: 36
ttttatctcc tgccatcttc catcggggag tcgccgtgac accattcagg aacaatgaat     60
gcggttatgg actcaagaag gcatgggct tcgtgttttt taatgctggg cctagttttt    120
ggtgcgacgg tcaaagcgga aaccaaattc agctacgaga ggctaagact cagagttacg    180
catcaaacca cgggcgacga atat                                           204

<210> SEQ ID NO 37
<211> LENGTH: 50
<212> TYPE: PRT
<213> ORGANISM: Viscum album

<400> SEQUENCE: 37

Met Asn Ala Val Met Asp Ser Arg Arg Ala Trp Ala Ser Cys Phe Leu
 1               5                  10                  15

Met Leu Gly Leu Val Phe Gly Ala Thr Val Lys Ala Glu Thr Lys Phe
             20                  25                  30

Ser Tyr Glu Arg Leu Arg Leu Arg Val Thr His Gln Thr Thr Gly Asp

```
                35                  40                  45

Glu Tyr
     50

<210> SEQ ID NO 38
<211> LENGTH: 705
<212> TYPE: DNA
<213> ORGANISM: Viscum album

<400> SEQUENCE: 38
ttccggttca tcacgcttct ccgagattat gtctcaagcg gaagcttttc caatgagata      60
ccactcttgc gtcagtctac gatccccgtc tccgatgcgc aaagatttgt cttggtggag    120
ctcaccaacc aggggggaga ctcgatcacg gccgccatcg acgttaccaa tctgtacgtc    180
gtggcttacc aagcaggcga ccaatcctac tttttgcgcg acgcaccacg cggcgcggaa    240
acgcatctct tcaccggcac cacccgatcc tctctcccat caacggaag ctaccctgat    300 ctggagcgat acgccggaca tagggaccag atccctctcg gtatagacca actcattcaa    360
tccgtcacgg cgcttcgttt ccgggcggc agcacgcgta cccaagctcg ttcgatttta    420
atcctcattc agatgatctc cgaggccgcc agattcaatc ccatcttatg gagggctcgc    480
caatacatta acgtggggc gtcatttctg ccagacgtgt acatgctgga gctgagacg    540 agttggggcc aacaatccac gcaagtccag cattcaaccg atggcgtttt taataaccca    600
attcggttgg ctatacccccc cggtaacttc gtgacgttga ccaatgttcg cgacgtgatc    660
gccagcttgg cgatcatgtt gtttgtatgc ggagagcggc catct                    705

<210> SEQ ID NO 39
<211> LENGTH: 235
<212> TYPE: PRT
<213> ORGANISM: Viscum album

<400> SEQUENCE: 39

Phe Arg Phe Ile Thr Leu Leu Arg Asp Tyr Val Ser Ser Gly Ser Phe
  1               5                  10                  15

Ser Asn Glu Ile Pro Leu Leu Arg Gln Ser Thr Ile Pro Val Ser Asp
             20                  25                  30

Ala Gln Arg Phe Val Leu Val Glu Leu Thr Asn Gln Gly Gly Asp Ser
         35                  40                  45

Ile Thr Ala Ala Ile Asp Val Thr Asn Leu Tyr Val Val Ala Tyr Gln
     50                  55                  60

Ala Gly Asp Gln Ser Tyr Phe Leu Arg Asp Ala Pro Arg Gly Ala Glu
 65                  70                  75                  80

Thr His Leu Phe Thr Gly Thr Thr Arg Ser Ser Leu Pro Phe Asn Gly
                 85                  90                  95

Ser Tyr Pro Asp Leu Glu Arg Tyr Ala Gly His Arg Asp Gln Ile Pro
            100                 105                 110

Leu Gly Ile Asp Gln Leu Ile Gln Ser Val Thr Ala Leu Arg Phe Pro
        115                 120                 125

Gly Gly Ser Thr Arg Thr Gln Ala Arg Ser Ile Leu Ile Leu Ile Gln
    130                 135                 140

Met Ile Ser Glu Ala Ala Arg Phe Asn Pro Ile Leu Trp Arg Ala Arg
145                 150                 155                 160

Gln Tyr Ile Asn Ser Gly Ala Ser Phe Leu Pro Asp Val Tyr Met Leu
                165                 170                 175

Glu Leu Glu Thr Ser Trp Gly Gln Gln Ser Thr Gln Val Gln His Ser
```

```
                    180              185              190
Thr Asp Gly Val Phe Asn Asn Pro Ile Arg Leu Ala Ile Pro Pro Gly
            195              200              205

Asn Phe Val Thr Leu Thr Asn Val Arg Asp Val Ile Ala Ser Leu Ala
        210              215              220

Ile Met Leu Phe Val Cys Gly Glu Arg Pro Ser
225              230              235

<210> SEQ ID NO 40
<211> LENGTH: 48
<212> TYPE: DNA
<213> ORGANISM: Viscum album

<400> SEQUENCE: 40
tcctctgagg tgcgctattg gccgctggtc atacgacccg tgatagcc                    48

<210> SEQ ID NO 41
<211> LENGTH: 16
<212> TYPE: PRT
<213> ORGANISM: Viscum album

<400> SEQUENCE: 41

Ser Ser Glu Val Arg Tyr Trp Pro Leu Val Ile Arg Pro Val Ile Ala
1               5                   10                  15

<210> SEQ ID NO 42
<211> LENGTH: 789
<212> TYPE: DNA
<213> ORGANISM: Viscum album

<400> SEQUENCE: 42
gatgatgtta cctgcagtgc ttcggaacct acggtgcgga ttgtgggtcg aaatggcatg     60
tgcgtggacg tccgagatga cgatttccgc gatggaaatc agatacagtt gtggccctcc    120
aagtccaaca atgatccgaa tcagttgtgg acgatcaaaa gggatggaac cattcgatcc    180
aatggcagct gcttgaccac gtatggctat actgctggcg tctatgtgat gatcttcgac    240
tgtaatactg ctgtgcggga ggccactctt tggcagatat ggggcaatgg gaccatcatc    300
aatccaagat ccaatctggt tttggcagca tcatctggaa tcaaaggcac tacgcttacg    360
gtgcaaacac tggattacac gttgggacag gctggcttg ccggtaatga taccgcccca    420
cgcgaggtga ccatatatgg gttcagggac ctttgcatgg aatcaaatgg agggagtgtg    480
tgggtggaga cgtgcgtgag tagccaaaag aaccaaagat gggctttgta cggggatggt    540
tctatacgcc ccaaacaaaa ccaagaccaa tgcctcacct gtgggagaga ctccgtttca    600
acagtaatca atatagttag ctgcagcgct ggatcgtctg ggcagcgatg ggtgtttacc    660
aatgaagggg ccattttgaa tttaaagaat gggttggcca tggatgtggc gcaagcaaat    720
ccaaagctcc gccgaataat catctatcct gccacaggaa aaccaaatca aatgtggctt    780
cccgtgcca                                                            789

<210> SEQ ID NO 43
<211> LENGTH: 263
<212> TYPE: PRT
<213> ORGANISM: Viscum album

<400> SEQUENCE: 43

Asp Asp Val Thr Cys Ser Ala Ser Glu Pro Thr Val Arg Ile Val Gly
1               5                   10                  15
```

```
Arg Asn Gly Met Cys Val Asp Val Arg Asp Asp Asp Phe Arg Asp Gly
         20                  25                  30

Asn Gln Ile Gln Leu Trp Pro Ser Lys Ser Asn Asn Asp Pro Asn Gln
         35                  40                  45

Leu Trp Thr Ile Lys Arg Asp Gly Thr Ile Arg Ser Asn Gly Ser Cys
 50                  55                  60

Leu Thr Tyr Gly Tyr Thr Ala Gly Val Tyr Val Met Ile Phe Asp
 65                  70                  75                  80

Cys Asn Thr Ala Val Arg Glu Ala Thr Leu Trp Gln Ile Trp Gly Asn
                 85                  90                  95

Gly Thr Ile Ile Asn Pro Arg Ser Asn Leu Val Leu Ala Ala Ser Ser
                100                 105                 110

Gly Ile Lys Gly Thr Thr Leu Thr Val Gln Thr Leu Asp Tyr Thr Leu
        115                 120                 125

Gly Gln Gly Trp Leu Ala Gly Asn Asp Thr Ala Pro Arg Glu Val Thr
    130                 135                 140

Ile Tyr Gly Phe Arg Asp Leu Cys Met Glu Ser Asn Gly Gly Ser Val
145                 150                 155                 160

Trp Val Glu Thr Cys Val Ser Ser Gln Lys Asn Gln Arg Trp Ala Leu
                165                 170                 175

Tyr Gly Asp Gly Ser Ile Arg Pro Lys Gln Asn Gln Asp Gln Cys Leu
                180                 185                 190

Thr Cys Gly Arg Asp Ser Val Ser Thr Val Ile Asn Ile Val Ser Cys
            195                 200                 205

Ser Ala Gly Ser Ser Gly Gln Arg Trp Val Phe Thr Asn Glu Gly Ala
        210                 215                 220

Ile Leu Asn Leu Lys Asn Gly Leu Ala Met Asp Val Ala Gln Ala Asn
225                 230                 235                 240

Pro Lys Leu Arg Arg Ile Ile Ile Tyr Pro Ala Thr Gly Lys Pro Asn
                245                 250                 255

Gln Met Trp Leu Pro Val Pro
                260

<210> SEQ ID NO 44
<211> LENGTH: 177
<212> TYPE: DNA
<213> ORGANISM: Viscum album

<400> SEQUENCE: 44
tgatttaggt tcatggctcg aagattgctt gcatgcgacc atcctttcta ttttctcttt      60
tctacctttt gaaataatgt ctgtgaataa tgtggcacgt tgaggcccgc cgaaagaagc     120
cttagccacc ttgtgtttga gaataaatga gttaatgcaa gcaatcaact tctcctt       177

<210> SEQ ID NO 45
<211> LENGTH: 29
<212> TYPE: DNA
<213> ORGANISM: Spodoptera frugiperda

<400> SEQUENCE: 45
aatatttccg gttcatcacg cttctccga                                        29

<210> SEQ ID NO 46
<211> LENGTH: 9
<212> TYPE: PRT
<213> ORGANISM: Spodoptera frugiperda

<400> SEQUENCE: 46
```

```
Tyr Phe Arg Phe Ile Thr Leu Leu Arg
  1               5
```

<210> SEQ ID NO 47
<211> LENGTH: 33
<212> TYPE: DNA
<213> ORGANISM: Spodoptera frugiperda

<400> SEQUENCE: 47
ggatccctat taagatggcc gctctccgca tac                          33

<210> SEQ ID NO 48
<211> LENGTH: 7
<212> TYPE: PRT
<213> ORGANISM: Spodoptera frugiperda

<400> SEQUENCE: 48

```
Val Cys Gly Glu Arg Pro Ser
  1               5
```

<210> SEQ ID NO 49
<211> LENGTH: 64
<212> TYPE: DNA
<213> ORGANISM: Spodoptera frugiperda

<400> SEQUENCE: 49
ctagacatat gtacgaacgt atccgtctgc gtgttaccca ccagaccacc ggtgaagaat    60
attg                                                                64

<210> SEQ ID NO 50
<211> LENGTH: 64
<212> TYPE: DNA
<213> ORGANISM: Spodoptera frugiperda

<400> SEQUENCE: 50
aattcaatat tcttcaccgg tggtctggtg ggtaacacgg atacgcagac gttcgtacat    60
atgt                                                                64

<210> SEQ ID NO 51
<211> LENGTH: 70
<212> TYPE: DNA
<213> ORGANISM: Spodoptera frugiperda

<400> SEQUENCE: 51
tctagacata tgtacgaacg tatccgtctg cgtgttaccc accagaccac cggtgaagaa    60
tattgaattc                                                          70

<210> SEQ ID NO 52
<211> LENGTH: 18
<212> TYPE: PRT
<213> ORGANISM: Spodoptera frugiperda

<400> SEQUENCE: 52

```
Met Tyr Glu Arg Ile Arg Leu Arg Val Thr His Gln Thr Thr Gly Glu
  1               5                  10                  15

Glu Tyr
```

<210> SEQ ID NO 53
<211> LENGTH: 26
<212> TYPE: DNA
<213> ORGANISM: Spodoptera frugiperda

```
<400> SEQUENCE: 53
catatggatg atgttacctg cagtgc                                              26

<210> SEQ ID NO 54
<211> LENGTH: 8
<212> TYPE: PRT
<213> ORGANISM: Spodoptera frugiperda

<400> SEQUENCE: 54

Met Asp Asp Val Thr Cys Ser Ala
  1               5

<210> SEQ ID NO 55
<211> LENGTH: 28
<212> TYPE: DNA
<213> ORGANISM: Spodoptera frugiperda

<400> SEQUENCE: 55
ggatccttat catggcacgg gaagccac                                            28

<210> SEQ ID NO 56
<211> LENGTH: 6
<212> TYPE: PRT
<213> ORGANISM: Spodoptera frugiperda

<400> SEQUENCE: 56

Met Trp Leu Pro Val Pro
  1               5
```

RECOMBINANT MISTLETOE LECTIN (RML)

RELATED APPLICATIONS

This application is the National Phase under 35 U.S.C. §371 of PCT/EP9602273, filed Jun. 25, 1996, designating the U.S. and claiming priority from EP A 95109949.8, filed Jun. 26, 1995.

FIELD OF THE INVENTION

The invention relates to nucleic acid molecules encoding preproproteins having after maturation the biological activity of the mistletoe lectin dimer, to vectors comprising these nucleic acid molecules, to hosts transformed with said vectors and to polypeptides and/or polypeptide dimers which are encoded by these nucleic acid molecules. The polypeptides and/or polypeptide dimers of the invention are widely therapeutically applicable. Thus, the present invention further relates to immunotoxins as well as to pharmaceutical compositions that contain the polypeptides and/or the polypeptide dimers of the invention. Additionally, the invention relates to diagnostic compositions comprising the nucleic acid molecules of the invention, the polypeptides and/or the polypeptide dimers of the invention and/or primers which hybridize specifically to the nucleic acid molecules of the invention. Finally, the invention relates to plant protective agents comprising the polypeptides of the invention and/or the polypeptide dimers of the invention.

BACKGROUND OF THE INVENTION

Mistletoe extracts have been therapeutically used for centuries. Since the beginning of this century, mistletoe preparations have been used in cancer therapy with varying success [Bocci, 1993; Gabius et al., 1993; Gabius & Gabius, 1994; Ganguly & Das, 1994]. Hajto et al. [1989, 1990] could show that the therapeutic effects are mediated in particular by socalled mistletoe lectins (viscumins, *Viscum album* agglutinins, VAA). Besides a cytotoxic effect today the art in particular discusses (unspecific) immunostimulation, the positive effects of which are used for the accompanying therapy and after-care of tumor patients. An increase in quality of life is possibly mediated in such patients by the secretion of endogeneous endorphins [Heiny and Beuth, 1994]. Numerous in vitro [Hajto et al., 1990; Männel et al., 1991; Beuth et al., 1993] and in vivo [Hajto, 1986; Hajto et al., 1989; Beuth et al., 1991; Beuth et al., 1992] studies as well as clinical studies [Beuth et al., 1992] report an increased release of inflammatory cytokines (TNF-α, IL-1, IL-6) as well as an activation of cellular components of the immunological system ($T_H$ cells, NK cells).

Today a 60 kDa mistletoe lectin protein is considered the active principle of the mistletoe extracts which can be biochemically obtained from extracts [Franz et al., 1977; Gabius et al., 1992]. The ML protein consists of two covalently S—S linked subunits, the A chain of which being responsible for the enzymatic inactivation of ribosomes [Endo et al., 1988] and its B chain being responsible for carbohydrate binding. Biological activity today is mainly attributed to the lectin activity of the B chain [Hajto et al., 1990].

However, little is known about the structure/function relationships of the mistletoe lectin (ML). The contribution which the single-chains and their different biochemical and enzymatic activities make to the mode of action and/or the therapeutic effects observed is not yet clear. The analysis of the structure/function relationships is rendered difficult by contamination of the preparations with other plant ingredients of the mistletoe [Stein & Berg, 1994]. It is discussed that the activity of extract preparations may depend on the different compositions of the preparations, which in turn may depend on the kind of the host tree (e.g., apple, pine, poplar) [Hülsen et al., 1986]. Both viscotoxins [Garcia-Olmedo et al., 1983; Mendez et al., 1990] and other viscumins (such as ML-2, ML-3) are said to have similar effects [Eifler et al., 1994]. Even ML preparations which have been highly purified biochemically (affinity chromatography) are substantially heterogeneous (FIG. 8).

This heterogeneity relates to the biochemically assessable activities of the chains, to the evoked in vitro and in vivo effects and to the protein structures as such. Structural variants are discussed for the glycosylations of the ML A and B chains as well as for sequence variations. Gabius et al. [1992] and Dietrich et al. [1992] show a sequence variability of the A1 and A2 chains of ML-1.

For a more detailed analysis of the therapeutic effects of the mistletoe lectin it is desirable that it is available as structurally homogeneous substance in pure form. Furthermore, it is important for the scientists to be able to prepare mistletoe lectin or its components in large amounts in pure form so that it/they can be employed on a large scale as active ingredient of pharmaceutical compositions. These aims could not be nearly attained by the processes so far known in the art. Isolation from plant material according to the present state of the art will always yield a heterogeneous mixture of substances. The heterogeneity of plant mistletoe lectin preparations inter alia results from the posttranslational processing of the ML-1 to the isoforms ML-2 and ML-3 so that mistletoe lectin preparations have a varying content of ML-1, ML-2 and ML-3 depending on the method of isolation or the duration of fermentation [Jäggy et al., 1995]. Any of the above-mentioned isoforms additionally is largely microheterogeneous which is illustrated in FIG. 8 for ML-1 by isoelectric chromatofocusing.

OBJECTS AND SUMMARY OF THE INVENTION

The problem underlying the present invention is therefore to provide mistletoe lectin in pure form and in amounts allowing its use on a large scale. The problem is solved by the embodiments characterized in the claims.

The invention thus relates to a nucleic acid molecule encoding (a) a preproprotein having after maturation the biological function of the mistletoe lectin dimer and having the nucleotide sequence depicted in FIG. 4*c*; (b) a fragment of the preproprotein according to (a), with the fragment being a biologically active component of the mistletoe lectin dimer; which (c) distinguishes itself from the nucleic acid molecule according to (a) or (b) by degeneration of the genetic code; or (d) hybridizes to the nucleic acid molecule according to (a), (b) or (c) under stringent conditions and encodes a polypeptide having the biological function and/or activity indicated in (a) or (b).

By providing the gene sequences of mistletoe lectin for the first time, recombinant, highly purified individual chains (rMLA, rMLB) that can be reassociated in vitro and thus give a rML holoprotein that is homogeneous in terms of its protein chemistry, its enzymatic activity and its structure could be obtained starting from said sequence. The reassociated recombinant protein is not variable nor microheterogeneous, particularly with respect to its primary structure and the posttranslational modifications (glycosylation, phosphorylation) and hence is particularly useful for therapy both as holoprotein, as partial chain and in form of subfragments.

According to the present invention a "fragment" of a mistletoe lectin preproprotein is understood to be any fragment, not only a naturally occurring fragment, being a biologically active component of the mistletoe lectin dimer. For reasons of clarity it is pointed out that the person skilled in the art obviously understands such a biologically active component of the mistletoe lectin dimer also to be those components that are components of the singlechains of the dimer. Therefore, also the single-chains or fragments thereof that form part of the sequence depicted in FIG. 4c are covered by the present invention. In the present invention, the term "naturally" in conjunction with "component of the mistletoe lectin" is understood such that the so characterized fragment is either a chain of the mistletoe lectin dimer or a subfragment of the chain that naturally occurs in said chain. These fragments are preferably biologically active.

In the present invention, the term "biologically active" is understood such that these fragments have at least one biological function of the chains or of the dimer as described in the present application or any other biological function of the single-chains or of the dimer. Furthermore, the term "biologically active" is meant to also relate to a pharmacological and/or an immunological activity.

The use of recombinant ML proteins furthermore for the first time allows to examine the contributions of the individual domains and subdomains by way of experimentation. Recombinant ML proteins and recombinant subunits/partial chains are the basis of correspondingly defined monosubstance preparations which can be used instead of extract preparations and standardized extracts.

Cloning of the gene encoding mistletoe lectin could surprisingly be brought about on the basis of a new cloning strategy, after conventional cloning strategies had failed:

A number of protein-chemical data are known for mistletoe lectin ML-1. In addition to its molecular weight and subunit structure particularly short N-terminal peptides are known the amino acid sequences of which have been described independently by Dietrich et al. [1992] and Gabius et al. [1992] [see also DE4221836]. Due to the amino acid composition and the pertaining high degree of degeneracy of the N-terminal peptides of the A and/or B chain starting from these peptides, it is virtually impossible to prepare synthetic oligonucleotides whose degree of degeneracy is sufficiently low to allow identification of ML gene fragments when screening genomic gene libraries. This is also true for cDNA gene libraries that were prepared on the basis of Viscumi album poly-(A+) RNA.

The polymerase chain reaction allows to amplify DNA stretches that are located between known stretches [Erlich et al., 1988]. Using a "sense" oligonucleotide starting from the N-terminus of MLA and an "antisense" oligonucleotide of the N-terminus of MLB, an amplification of the intervening genetic region is conceivable provided that the ML gene is free of introns (FIG. 1a). In practice, however, an analysis of the N-terminal sequence of the B chain shows that the degree of degeneracy of the conceivable combinations of oligonucleotides is much too high for a successful realization of this approach. The reason may particularly be the sequence of the B chain N-terminus which is unfavorable for an oligonucleotide construction and which renders an amplification of ML gene sequences starting from the known amino acid sequence regions impracticable (FIG. 1b).

When trying to clone the ML gene using a modified PCR strategy, scientists therefore tried to incorporate further protein data, particularly on the basis of the kinship of the mistletoe lectin to the class I and II ribosome-inactivating proteins (RIPs), to construct amplification oligonucleotides [Stirpe et al., 1992]. Based on multiple alignments of (a) type I RIP proteins and ricin A chains as well as (b) the B chains of abrin and ricin conserved regions were identified in a total of 8 sequence stretches. Starting from these sequence regions and while considering codon usage tables of related species, a total of 21 oligonucleotides was constructed and used in various combinations in more than 200 amplification tests. In none of the cases, however, specific amplification products could be obtained, although the PCR conditions were widely varied as regards annealing temperature, $Mg^{2+}$ content as well as cycle parameters.

Both the screening of genomic and cDNA libraries and the use of PCR techniques did not allow to arrive at specific ML DNA sequences when following the above-mentioned deliberations.

Therefore, there had been attempts at finding new ways of including further structural properties of the ricin and abrin structure in the construction of the amplification oligonucleotides.

Since the enzymatic mechanism of ribosome-inactivating proteins (RIPs), here particularly the type II RIP ricin, is similar to that of ML [Endo et al., 1988a+1988b], it could not be excluded that they are also structurally similar on the level of the functional primary and tertiary structures. Starting from the crystalline structure of ricin [Katzin et al., 1991; Rutenber & Robertus, 1991; Weston et al., 1994] an analysis of the chain flexibilities in the ricin A chain pointed to a low mobility of Arg180 which is located within a conserved sequence region. Additionally, an analysis was made of the possible amino acid substitutions in this region of the active center which may occur due to the steric arrangement of the chain's "backbone" while duly considering the substrate interactions. The results of these deliberations were correlated with an evaluation of the extensive sequence alignments of the ricin A chain and further type I RIPs.

The supplementation of the results of the sequence comparisons through the inclusion of structural data thus yielded probabilistic data for the occurrence of certain amino acid residues at certain positions. These data could be used to postulate a number of theoretical ML amino acid sequences for this region and, on the basis of the latter, to construct a corresponding oligonucleotide (RMLA2) (SEQ ID NO:2) of surprisingly low degeneracy (FIG. 1c). By combining RMLA1 (SEQ ID NO:1) (a degenerate oligonucleotide derived from the N-terminal amino acid sequence of the MLA chain; cf. FIG. 1b) and the "active site" oligonucleotide RMLA1 (SEQ ID NO:2) constructed on the basis of the above deliberations, fragments could be obtained at defined PCR parameters starting from complex genomic ML-DNA after all the alternative approaches described above had failed.

The sequence information of the gene was then completed via specific non-degenerate oligonucleotide primers, derived from the partial gene sequence of MLA obtained by cloning and sequencing of fragment a (FIG. 3) and degenerate oligonucleotides, derived from RIP I and ricin/abrin sequence alignments, using additional PCR amplifications. In order to construct the degenerate B chain oligonucleotides, sequence alignments of the B chains of the ricins and abrins were used where some highly conserved regions were found.

For the determination of the 5' and 3' ends of the holo protein, B chain partial fragments and the 5' and 3' non-translated regions, analogous cDNA was synthesized by reverse transcription starting from isolated mistletoe RNA and the respective gene sections were obtained using the RACE technique [Frohman et al., 1988]. Once a multitude of overlapping gene fragments was available (FIG. 3) complete A chain and B chain gene sections, each starting from complex genomic mistletoe DNA, were obtained by specific PCR. The gene sequences of rMLA and rMLB, both provided with terminal, modifications, are depicted in FIG. 4a and FIG. 4b (SEQ ID NOS:32 and 33). The complete ML gene sequence which comprises also 5' and 3' non-translated regions as well as endopeptide and signal peptide encoding gene sections is depicted in FIG. 4c (SEQ ID NOS:34 and 35).

In a preferred embodiment of the nucleic acid molecule of the invention, the fragment is the A chain of mistletoe lectin which is encoded by the nucleotide sequence depicted in FIG. 4a (SEQ ID NOS:30 and 31) (MLA).

In a further preferred embodiment of the nucleic acid molecule of the invention, the fragment is the B chain of mistletoe lectin which is encoded by the nucleotide sequence depicted in FIG. 4b (SEQ ID NOS:32 and 33) (MLB).

A further preferred embodiment of the invention relates to a nucleic acid molecule which is a DNA molecule.

In the present invention, the term "DNA molecule" is understood to relate to both a genomic and a cDNA molecule or a (semi)synthetic DNA molecule. In knowledge of the teaching of the present invention, processes for the preparation of these various DNA molecules are well-known to the person skilled in the art.

In a further preferred embodiment of the invention the nucleic acid molecule is an RNA molecule.

The invention furthermore relates to a nucleic acid molecule that is an antisense strand to any of the above-described nucleic acid molecules of the invention. Such an antisense strand can exemplarily be used for transcription inhibition and thus for expression and regulation studies in plants.

The invention also relates to a vector that contains at least one nucleic acid molecule according to the invention.

The vector according to the invention can, for example, contain a single nucleic acid molecule according to the invention that encodes the entire mistletoe lectini preproprotein. Provided that said vector is an expression vector, the preproprotein can be processed in a suitable transformed host and the monomeric units can be joined in vivo or in vitro to give a mistletoe lectin dimer. In another embodiment, the vector according to the invention is a vector that is only used for propagation of the nucleic acid according to the invention.

In a preferred embodiment, the vector according to the invention contains both a nucleic acid molecule encoding the A chain of the mistletoe lectin or a fragment thereof and a nucleic acid molecule encoding the B chain or a fragment thereof. Preferably, the fragments of the monomers are biologically active.

In a further preferred embodiment, the vector according to the invention is an expression vector. It is clear to the person skilled in the art how to provide suitable expression vectors for various host organisms.

According to the invention, a sequence encoding the mistletoe lectin A chain was produced for heterologous expression by specific PCR starting from complex genomic mistletoe DNA. Via non-complementary regions of the primer oligonucleotides used translation control elements as well as recognition sequences of restriction endonucleases were added, thereby allowing cloning and separate expression of the mistletoe lectin A chain on the basis of the prepro-mistletoe lectin gene which was present in genomic form.

The 5' region of the sequence encoding rMLA corresponding to the amino acid residues tyrosine[1]–tyrosine[17] [Dietrich et al., 1992; Gabius et al., 1992] was prepared as a synthetic gene fragment by hybridization and cloning of two oligonucleotides and by addition of a translation start codon. In this way, the gene sequence was optimized as regards the codon choice such as described for strongly expressed genes in Escherichia coli [Gribskov et al., 1984]. At the 3' end of the synthetic rMLA gene fragment as well as at the 5' end of the rMLA gene fragment obtained by PCR, an Ssp I restriction site was introduced by specific exchange of the tyrosine[17] codon from TAC to TAT, which restriction site allowed fusion of the two rMLA gene fragments while obtaining vector pML14–17 (FIG. 5). The sequence encoding rMLA was confirmed by DNA sequencing (FIG. 4a) (SEQ ID NOS:30 and 31). For expression of rMLA in Escherichia coli, the gene sequence was isolated from vector pML14–17 and was put under the control of the T7-RNA polymerase promoter and a transcription terminator by insertion into expression vector pT7-7 [Studier & Moffart, 1986]. The resulting expression vector pT7-MLA (FIG. 5) was used to transform the E. coli expression strain BL21. Induction of the gene expression is characterized by the occurrence of a protein band corresponding to the non-glycosylated, recombinant mistletoe lectin A chain which possesses a relative molecular weight of 25 kDa. Assay and identification of the recombinant expression product was performed by Western blot analysis using a specific anti-MLA antibody (FIG. 7).

For a heterologous expression of the mistletoe B chain the complete, MLB encoding sequence was amplified by specific PCR from complex genomic Viscum album DNA. Translation control elements and recognition sequences for restriction endonucleases were introduced (FIG. 6) via non-complementary regions of the primer oligonucleotides used. The resulting 0.8 kbp PCR product was put under the control of transcription control elements after cloning in the TA cloning vector pCRII by insertion in the expression vector pT7-7 and the expression strain E. coli BL21 was transformed with the resulting expression vector pT7-MLB.

The integrity of the rMLB encoding sequence was confirmed by DNA sequencing (FIG. 4b)(SEQ ID NOS:32 and 33). The expression was detected in a Western blot assay using a specific anti-MLB antibody (TB33, Tonevitsky et al., 1995), wherein 2 hrs after induction of gene expression an immunoreactive protein having a relative molecular weight of 31 kDA corresponding to the non-glycosylated, recombinant mistletoe lectin B chain occurred (FIG. 7b). Analysis of the cell fractions after complete cell discruption of the E. coli cells showed a division of the synthesized rMLB chain into a soluble fraction in the supernatant as well as an insoluble inclusion body fraction in the sediment of the E. coli cell disruption. 4 hrs after induction the soluble and insoluble fractions accounted for 50% each of the total yield (FIG. 7b).

The invention furthermore relates to a host transformed with at least one vector according to the invention.

Depending on the objective pursued by the person skilled in the art, the host according to the invention can only be used to prepare either one of the monomers or a combination of both monomers, preferably as associated dimer. The host according to the invention can be a eucaryotic or procaryotic cell, a transgenic plant or a transgenic animal.

Preferably, the host according to the invention is a mammalian cell, a plant cell, a bacterium, a fungal cell, a yeast cell, an insect cell or a transgenic plant.

In a particularly preferred embodiment, the host according to the invention is the bacterium E. coli, an Aspergillus cell or a Spodoptera cell, preferably Spodoptera frugiperda.

The invention furthermore relates to a polypeptide which is encoded by the nucleic acid molecule according to the invention or by the vector according to the invention and/or which is produced by the host according to the invention.

The polypeptide according to the invention preferably has the biological activity of the A chain or the B chain of the mistletoe lectin. In other embodiments, however, the polypeptide according to the invention can exhibit only part of the biological activity or no biological activity at all. In the invention, "part of the biological activity" is understood to relate to either a reduced activity and/or a number of activities from the range of biological activities. The polypeptide according to the invention can be a fragment of the A or B chain which exhibits the above-mentioned properties.

DETAILED DESCRIPTION

Examination of the Properties of rMLA, rMLB and rML Holoprotein (I) Relative Molecular Weights and Structure The relative molecular weights were determined by SDS polyacrylamide gel electrophoresis under reducing conditions and subsequent protein staining with silver or Coomassie Brilliant Blue or by immunological staining in a Western blot analysis.

It was surprisingly found that the recombinant, non-glycosylated mistletoe lectin A chain has a relative molecular weight of 25 kDa and thus significantly differs from the naturally occurring mistletoe lectin A chains $A_1$ with 31 kDA and $A_2$ with 29 kDa. This difference in relative molecular weight is particularly surprising since it was assumed in the prior art that the A chain is not glycosylated. The recombinant mistletoe B chain has a relative molecular weight of 31 kDa and is hence substantially lighter than the glycosylated, naturally occurring mistletoe lectin B chain with 36 kDa (FIG. 7).

The heterogeneity of naturally occurring ML proteins due to glycosylation and/or sequence variations, which becomes apparent in the SDS gel as broad band, does not occur in the recombinant species in any of the cases examined.

The relative molecular weights of the reassociated rMLA/rMLB holoproteins (rML) add up to 56 kDa as compared to the heavier nML with 65–67 kDa.

(II) Isoelectric Homogeneity rMLA turns out to be an isoelectrically homogeneous protein having an isoelectric point of 6.8 as compared to highly purified naturally occurring mistletoe lectin A chains which are divided into 4 species with isoelectric points of 5.2; 5.4; 5.7 and 6.2 (FIG. 8).

rMLB proves to be an isoelectrically homogeneous protein having an isoelectric point of 5.1 as compared to the naturally occurring mistletoe lectin B chain which is divided into at least 2 species with isoelectric points of 7.1 and 7.3 (FIG. 8).

Hence, for the naturally occurring ML holoprotein there is a multitude of possible molecule variants and combinations (FIG. 8, bottom) while for recombinant mistletoe lectin proteins there is a uniform mobility in the IEF chromatofocusing, which reveals the homogeneity of rML vis-à-vis the microheterogeneity of the naturally occurring protein species.

(III) Enzymatic Activity of rMLA

When using immunoaffinity purified rMLA preparations in a combined transcription/translation assay, translation inhibiting activity could be detected for rMLA (isolated from the soluble expression production fraction) and rMLA (isolated from insoluble "inclusion body" fraction).

rMLA showed a different inhibitory characteristic vis-à-vis the naturally occurring mistletoe lectin A chain with respect to the dosage dependency of the translation inhibition as well as with respect to the non-inhibitable residual translation activity in the reticulocyte lysate used (see FIG. 9). The enzymatic property that forms the basis for the toxic effect of ML holoproteins is significantly reduced in recombinant species.

(IV) Carbohydrate-binding Activity of rMLB rMLB chains that are produced by renaturation and reoxidation from the primary expression products, like the in vitro reassociated rMLA/rMLB, rMLA/MLB and MLA/rMLB holoproteins have carbohydrate-binding activity that can be detected by enzyme-linked lectin assay (ELLA) by binding to carbohydrate matrices asialofetuin or fetuin. Carbohydrate specificity of the recombinant rMLB chain can be determined and quantified in the ELLA system under competitive conditions for galactose, β-lactose, N-acetylgalactosamine (GalNAc) and sialic acid (N-acetyl neuraminic acid, NANA). The competitive ELLA test surprisingly shows different carbohydrate specificities for nMLB and rMLB. The binding affinity is characterized by the system-specific IC50 values for the half-maximal displacement of the proteins of the immobilized asialofetuin ligand by galactose (IC50 nMLB: 4.5 mM; IC50 rMLB: not determinable due to too low interaction), β-lactose (IC50 nMLB: 4.9 mM; IC50 rMLB:>70 mM), N-acetylgalactosamine (IC50 nMLB: 20.7 mM; IC50 rMLB: 109 mM) or of the immobilized fetuin ligand by sialic acid (IC50 nMLB: 49.8 mM; IC50 rMLB: 47.1 mM).

While the nMLB chain described as galactose-specific lectin can be displaced by galactose and β-lactose as expected, the rMLB chain obtained recombinantly in *E. coli* does not show any detectable interaction with galactose and only poor interaction with β-lactose. Recombinant rMLB in turn possesses clear affinity to N-acetylgalactosamine and sialic acid and surprisingly shows a substantial shift of the carbohydrate specificity towards an N-acetylgalactosamine/sialic acid specific lectin vis-à-vis plant nMLB. With respect to the biological activity of rMLB and rMLB containing holoproteins this results in the possibility of a range of ligands, receptors or target cells that is extended beyond or different from that of plant mistletoe lectin proteins.

In a preferred embodiment, the polypeptide according to the invention has at least one chemical or enzymatic modification.

This modification can change, reduce or increase the biological activity of the polypeptide, if any. Such a modification can be performed, e.g., after translation and isolation of the polypeptide. Such modifications can be also introduced during chemical or semi-synthetical preparation of the polypeptide according to the invention. These modifications can be introduced by the skilled person by methods known per se to alter the pharmacological activity of the mistletoe lectin, preferably to improve it.

In another preferred embodiment, the polypeptide according to the invention is a fusion protein. The fusion protein preferably has the above-defined biological activity.

This embodiment of the polypeptide according to the invention is also preferably designed to alter the pharmacological properties of the mistletoe lectin polypeptides for targets on the cellular level and preferably to improve them.

The invention furthermore relates to a polypeptide dimer having the biological activities of mistletoe lectin, with the two monomers being encoded by the nucleic acid molecules according to the invention.

The term "biological activity of the mistletoe lectin" is understood to comprise any biological activity from the specter of the entire biological activities of mistletoe lectin. Such a function is, e.g., the pharmacological effect of mistletoe lectin.

Plant mistletoe 1 induced cytolysis in numerous tumor cell lines of human and murine origin by apoptotic mechanisms [Janssen, 1993]. Mistletoe lectin 1 or the B chain alone induced the release of cytokines from peripheral mononuclear cells of healthy, human blood donors [Hajto, 1990]. Mistletoe lectin 1 induced the secretion of superoxide anions from neutrophilic granulocytes of cancer patients [Timoshenko, 1993]. Mistletoe lectin 1 induced the expression of the A chain of the interleukin 2 receptor (CD25) and/or the HLA DQ antigen on pheripheral lymphocytes of healthy, human blood donors [Beuth, 1992]. After application of mistletoe lectin 1 in mice, an increase in the number of thymocytes, the number of cytotoxic T-lymphocytes (Lyt-2+) and helper T-cells (L3T4+) in the thymus and the number of peritoneal macrophages, particularly of those carrying the activation marker MAC-3, could be observed [Beuth, 1994]. The relation of L3T4+/Lyt2+ in the thymus of the experimental animals was increased. In the peripheral blood of the mice the density of the leukocytes, lymphocytes, monocytes in general and in particular of the lymphocytes, which express the interleukin 2 receptor as activation marker on the cell surface, and the monocytes, which express the activation marker MAC3, was increased after treatment with mistletoe lectin 1 [Beuth, 1994]. In the blood of cancer patients mistletoe lectin 1 increased the density of T-lymphocytes (CD4+, CD8+), of the natural killer cells and the B-lymphocytes [Beuth, 1992].

Furthermore, an increase of the endogeneous opiate mediator β-endorphin in the blood plasma of mamma carcinoma patients could be detected after application of mistletoe lectin 1 [Heiny, 1994]. It was furthermore ascertained that mistletoe lectin 1 increases the cytotoxic effect of peripheral, natural killer cells vis-à-vis K-562 tumor cells and the density of large, granular lymphocytes (LGL) in the peripheral blood [Hajto, 1989]. An antimetastatic activity of mistletoe lectin 1 on sarcoma cells in mice could also be detected [Beuth, 1991].

In another embodiment, the polypeptide dimer according to the invention has the same range of biological activities as the naturally occurring mistletoe lectin dimer.

(V) Biological Activities of the Recombinant Mistletoe Lectin

The rML holoproteins were produced using the single-chains that had been recombinantly synthesized in a separate step in vitro starting from folded soluble chains or from denatured rMLA and rMLB chains in a co-folding step, wherein rMLB was preferably reassociated with a molar excess of rMLA in the presence of a glutathion redox system and partially in the presence of protein disulfide isomerase. The rML holoprotein corresponding to the heterodimer was isolated and purified from the reassociation reaction by affinity chromatography on N-acetylgalactosamine agarose or lactosyl agarose, thereby separating it from free rMLA and rMLA dimers. In an analogous manner rMLA/rMLB (rML) and rMLA/nMLB heterodimer holoproteins were prepared.

Cytotoxic Activity

The cytotoxic effect as an example of the biological activity of reassociated holoproteins was tested on a human monocyte leukemia cell line (MOLT4). Both B chain (surface binding) and A chain (enzymatic ribosome inactivation) contribute to the cytotoxic effect observed. An in vitro reassociated rMLA/rMLB holoprotein as well as an in vitro reassociated rMLA/nMLB holoprotein were compared with two batches of naturally occurring nML holoprotein. The recombinant rMLA/rMLB and rMLA/nMLB holoproteins show comparably high cytotoxic properties with IC values of about 10–30 pg/ml (FIG. 11), which reveals the functional integrity and biological activity of the rML holoproteins which were reassociated in vitro using recombinant chains. For the cytotoxic activity to take effect it is necessary that the B chain is operably linked with an enzymatically active A chain, since the isolated rMLB chain alone surprisingly does not have cytotoxic activity. The cytotoxic activity of plant mistletoe lectin B chain preparations which has so far been discussed can therefore probably be attributed to a residual content of nML holoprotein. The recombinant production of the single-chains hence for the first time ever makes it possible to separately describe and employ carbohydrate-binding and enzymatic activity of the mistletoe lectin.

Induction of Apoptosis

The capability for induction of apoptosis as an example of a biological activity of mistletoe lectin was demonstrated for the recombinant rML holoprotein using the monocyte cell line U937. 24 hrs after treatment of the cells with 70 pg/ml, induction of apoptosis by rML holoprotein could be detected (FIG. 12). Tests with mistletoe lectin on MOLT-4 cells and peripheral blood mononuclear cells (PBMC) showed that in the low dosage range the induction of apoptotic processes is the basis for the cytotoxic activity of the mistletoe lectin. Since cytokine induction occurs in the concentration range of low cytotoxicity (FIG. 13, FIG. 14), a correlation with the apoptosis-inducing activity is plausible, while in the high dosage range as well as with longer incubation times the apoptosis is superimposed by necrotic effects. A cytotoxicity as a result of apoptosis could not be detected when treating the sensitive MOLT-4 cells with the recombinant B chain so that the biological activity of the apoptosis induction in the low dosage range can only be attributed to the effect of the holoprotein.

Immunostimulating Activity

The immunostimulating effects as examples of biological activities of recombinant mistletoe lectin holoprotein were exemplarily tested for the induction of a tumor necrosis factor α (TNF-α) and interferon γ (IFN-γ) release from human mononuclear cells of healthy blood donors (PBMC model) as well as for the induction of an interleukin-1α (IL-1α) and interleukin-6 (IL-6) release in a coculture of human primary keratinocytes and skin fibroblasts (skin$^2$ ZK1200 model). In the PBMC model, 3–48 ng/ml of recombinant rML holoprotein resulted in a dosage-dependent release of TNF-α and IFN-γ, in the skin$^2$ model, 0.25–8 ng/ml of recombinant rML holoprotein resulted in a dosage-dependent release of IL-1α and IL-6.

All cytokines mentioned are relevant stimulating mediators of the human immunological system, which have central functions in the activation of particularly the cellular immune response.

In contrast to the state of the art up to now, according to which the immunostimulating activity can be mainly attributed to the lectin activity of the B chain [Hajto et al., 1990], none of the above-mentioned cytokine releases could be induced with the recombinant rMLB chain alone. The immunostimulating activity could only be achieved in the low dosage range by operably linked rML holoprotein. This surprising finding suggests that immunostimulating preparations of the plant rMLB chain still contained traces of nML holoproteins and that the immunostimulating effect which had been attributed to the nMLB chain must be attributed to a residual content of nML. While the processes for preparing nMLB which have been described so far do therefore not allow a quantitative separation of holoprotein, the recombinant realization of the individual mistletoe lectin chains for the first time ever makes it possible to examine and provide homogeneous mistletoe lectin B chain preparations. This allows for the first time to separately describe and employ the biological activities of A and B chain and to distinguish the biological activities of single-chains and operably linked holoprotein.

(VI) Biological Activities of the Recombinant Mistletoe Lectin B Chain (rMLB)

As marker for the activation of immunocompetent cells, the induction of the cell surface protein CD69 was tested. CD69 appears as one of the first cell surface antigens after activation of T cells, B cells and particularly of natural killer cells (NK cells). CD69 has the function of an activation marker of the above-mentioned immunocompetent cell populations since the cell surface protein is not expressed on resting lymphocytes. Furthermore, the inducible CD69 surface protein was proven to have a conducive function for the cytolytic activity of the NK cells and TcR$\gamma$/$\delta$ T cells [Moretta et al., 1991].

Flow cytometry (FACS) using an anti-CD69 mAb was employed to detect in the concentration range of 1–100 ng/ml an activation of the mononuclear cells both with respect to the occurrence of CD69 on the cell surface and to the share of CD69-positive cells. The curve for the dosage-dependency was bell-shaped, which points to the necessity for the interlinkage of cellular receptors via both ligand binding sites of the rMLB chain. A cytotoxic effect on the PBMC examined in this test could not be proven, not even at the highest concentration of 100 ng/ml rMLB.

In a preferred embodiment, the polypeptide dimer according to the invention exhibits as at least one of the monomers a chemically or enzymatically modified polypeptide according to the invention or a fusion protein according to the invention.

Modifications can be used to optimize the potency but also to broaden the possible therapeutic uses by eliminating certain qualities (e.g., carbohydrate binding sites of the B chain or glycosidase activity of the A chain) and thus eliminating possible side-effects. Polypeptides having modified properties can also serve as tools for elucidating the mechanisms of action. It can become necessary for certain therapies to reduce the antigenicity and the immunogenicity of the polypeptides and/or to optimize their pharmacokinetic properties, which would be possible by specifically exchanging individual amino acids.

The invention furthermore relates to antibodies or fragments thereof or derivatives which specifically bind the polypeptide and/or polypeptide dimer according to the invention. They therefore do not recognize the naturally occurring mistletoe lectin or single-chains thereof. Preferably, the antibodies according to the invention bind to epitopes which are masked by the glycosylations of the naturally occurring mistletoe lectins. The antibodies can be monoclonal, polyclonal or (semi)synthetic antibodies. The fragments can be, e.g., Fab', F(ab)$_2$ or Fv fragments. Antibody derivatives are also known in the art.

The invention furthermore relates to a method for preparing the polypeptide or polypeptide dimer according to the invention, in which method the host according to the invention is cultured under appropriate conditions and the so obtained polypeptide or polypeptide dimer is isolated.

The person skilled in the art is familiar with the appropriate conditions for culturing and isolating the host. For example, the polypeptide or polypeptide dimer according to the invention can be exported from the host via an appropriate expression system and can be collected in the medium. On the other hand, the polypeptides or polypeptide dimers can remain in the cell and can be isolated from there. In the following, we will discuss another preferred embodiment of the method according to the invention:

In order to isolate rMLA E. coli cells transformed with an appropriate expression vector were broken up and the soluble and insoluble cell fractions were separated by centrifugation. An analysis of the cell fractions showed that the recombinant mistletoe lectin A chain is accumulated by 5–50% in soluble form and by 50–95% in form of insoluble protein aggregates ("inclusion bodies") depending on the expression conditions and the expression duration.

The occurrence of soluble and insoluble proteins indicates that there are at least two methods for the isolation of rMLA, if a refolding or renaturation of the rMLA proteins is possible. The rMLA aggregated to "inclusion bodies" was dissolved after washes of the sediments to remove E. coli proteins [Babbitt et al., 1990] under denaturing conditions and was refolded by 90-fold dilution in folding buffer (50 mM Tris-HCl, 2 mM DTT, 1 mM EDTA, pH 8.0).

This treatment resulted in soluble, folded protein species which, as depicted in FIG. 9, had full enzymatic activity just like the renatured, originally insoluble, denatured rMLA species. The renatured rMLA can be isolated like the soluble rMLA by immunoaffinity chromatography using the specific anti-MLA antibody TA5 [Tonevitsky et al., 1995].

The presence of rMLB in soluble form as well as in form of insoluble "inclusion bodies" indicates that there are two methods for isolating recombinant mistletoe lectin B chain.

In order to isolate the soluble rMLB chain from the strongly reductive environment of the E. coli cytoplasm it is incubated in the presence of a redox system consisting of reduced and oxidized glutathion so as to establish the intrachain disulfide bridges and incubated in the presence of the ligand $\beta$-lactose in order to stabilize active folding products. From the folding reaction active, carbohydrate-binding rMLB chain was selectively isolated and/or purified in a one-step process by affinity chromatography on lactosyl agarose or N-acetylgalactosamine agarose.

In order to isolate rMLB from insoluble expression product fractions which were present as "inclusion bodies" the sediment of the E. coli cell complete cell disruption was washed to remove E. coli proteins [Babbitt et al., 1990] and dissolved under denaturing and reducing conditions. Renaturation was carried out by dilution in the presence of a redox system consisting of reduced and oxidized glutathion as well as in the presence of the ligand $\beta$-lactose. Active carbohydrate-binding rMLB chain was selectively isolated and purified from the renaturation reaction by affinity chromatography on N-acetylgalactosamine agarose or lactosyl agarose.

The invention furthermore relates to a pharmaceutical composition comprising the polypeptide according to the invention or the polypeptide dimer according to the invention and/or the immunotoxin according to the invention which will be described below, optionally in admixture with a pharmaceutically acceptable carrier.

The polypeptides according to the invention, their associates or modifications lend themselves for manifold applications in the therapy of cancer or infections in analogy to the pharmacological properties known for naturally occurring mistletoe lectin. The immunostimulating effects can be used for tumor therapy by directly and/or indirectly stimulating the body's own immunological defense and enabling it to more effectively combat the tumor and possible metastases. The same holds true for infections, in particular viral infections. The polypeptides according to the invention can be administered in combination with other immunostimulating agents such as interferons, cytokines or colony-stimulating factors, in order to achieve synergistic effects or to reduce the necessary dose of the combination preparation and thus to reduce its side-effects.

In combination with cytostatic agents or radiation therapy the side-effect of leucopenia/myelosuppression can be mitigated or reduced so that the weakening of the immunological system that is brought about by the conventional methods of treatment is reduced. The direct cytotoxic effect of the polypeptides having glycosidase activity results in the apoptosis of tumor cells and can also be used for therapeutical purposes. This principle can be made use of more specifically for the application of immunotoxins if the polypeptides according to the invention are coupled to appropriate antibodies. Hence, the invention furthermore relates to immunotoxins that comprise at least one polypeptide or polypeptide dimer according to the invention. For example, active A chain or holoprotein can be coupled to antibodies or fragments thereof by methods of protein chemistry. Such coupling processes are known to the person skilled in the art, the corresponding conjugates are useful for many purposes [Vitetta, 1993]. Alternatively, correspondingly constructed fusion protein constructs can be expressed that contain the antigen-binding domain from, e.g., antibodies and, in addition to that, cytotoxic fragments of the polypeptide according to the invention.

Furthermore, the formation of metastases can be prevented if the binding of the tumor cells to other cells is inhibited. The polypeptides according to the invention can be used to prevent such binding making use of competitive lectin binding.

The invention furthermore relates to a primer and/or a primer pair that specifically hybridizes to the nucleic acid molecule according to the invention or to the complementary strand thereof.

The invention furthermore relates to diagnostic compositions containing at least:

a) the nucleic acid molecule according to the invention;
b) a primer and/or a primer pair that specifically hybridizes to the nucleic acid molecule according to the invention or to the complementary strand thereof; and/or
c) the polypeptide according to the invention and/or the polypeptide dimer according to the invention.

The diagnostic composition according to the invention containing the primer and/or the primer pair can be used to screen organisms for the presence of a lectin gene so as to find, e.g., new lectin genes that might encode pharmacologically interesting lectins. The nucleic acid molecule according to the invention contained in the diagnostic composition according to the invention can be used to screen organisms for the presence of such lectin genes by, e.g., Southern blot or Northern blot methods. By varying the hybridization stringency related lectin genes can be screened for. The polypeptide (dimer) can be used, e.g., to generate antibodies or antisera which can be used to detect by methods known per se respective (mistletoe) lectins in various organisms.

Finally, the invention relates to plant protective agents containing the polypeptide according to the invention and/or the polypeptide dimer according to the invention. The polypeptides according to the invention, their associates or modifications can be used as plant protective agents according to the function discussed for plant mistletoe lectin. The function of the mistletoe lectin as an anti-viral protection is discussed due to its toxic properties as protective measure of the plant against being eaten as well as due to properties that have an effect on the permeability and constitution of membranes.

BRIEF DESCRIPTION OF THE DRAWINGS

The figures show

FIG. 2 shows the results of primary *Viscum album* ML amplification product;

FIG. 3 shows the cloning strategy for obtaining the ML gene (fragments a, b, c, d, e, f, g, h, I, j);

FIG. 4 (FIGS. 4a, 4b, 4c) show sequences of the inserts of the expression vectors for the rMLA and rMLB and complete ML gene sequences, with amino acid sequences (SEQ ID NOS: 1, 2, 3, 4 and 5;

FIG. 7 (FIGS. 7a, 7b) show the results of expression of rMLA, rMLB (SDS-PAGE, immunological detection (Western Blot));

FIG. 13 (FIGS. 13a, 13b) shows the immunostimulating effect of recombinant mistletoe lectin (rML) in the PBMC model (induction of secretion of TNF-α and of IFN-γ by rML);

FIG. 14 (FIGS. 14a, 14b) shows the immunostimulating effect of recombinant mistletoe lectin (rML) in the skin$^2$ model (induction of secretion of IL-1α and of IL-6 by rML)

The examples serve to illustrate the invention.

EXAMPLES

Example 1

Construction of the Primary Amplification Oligonucleotides

Mistletoe lectin (ML) belongs to the class of ribosome-inactivating proteins [Stirpe et al., 1992] which represents a protein family widely common to plants of various taxonomic origin. ML was attributed to the group of the type II ribosome-inactivating proteins due to the activities of its subunits [Endo et al., 1988a].

Figure 1A:
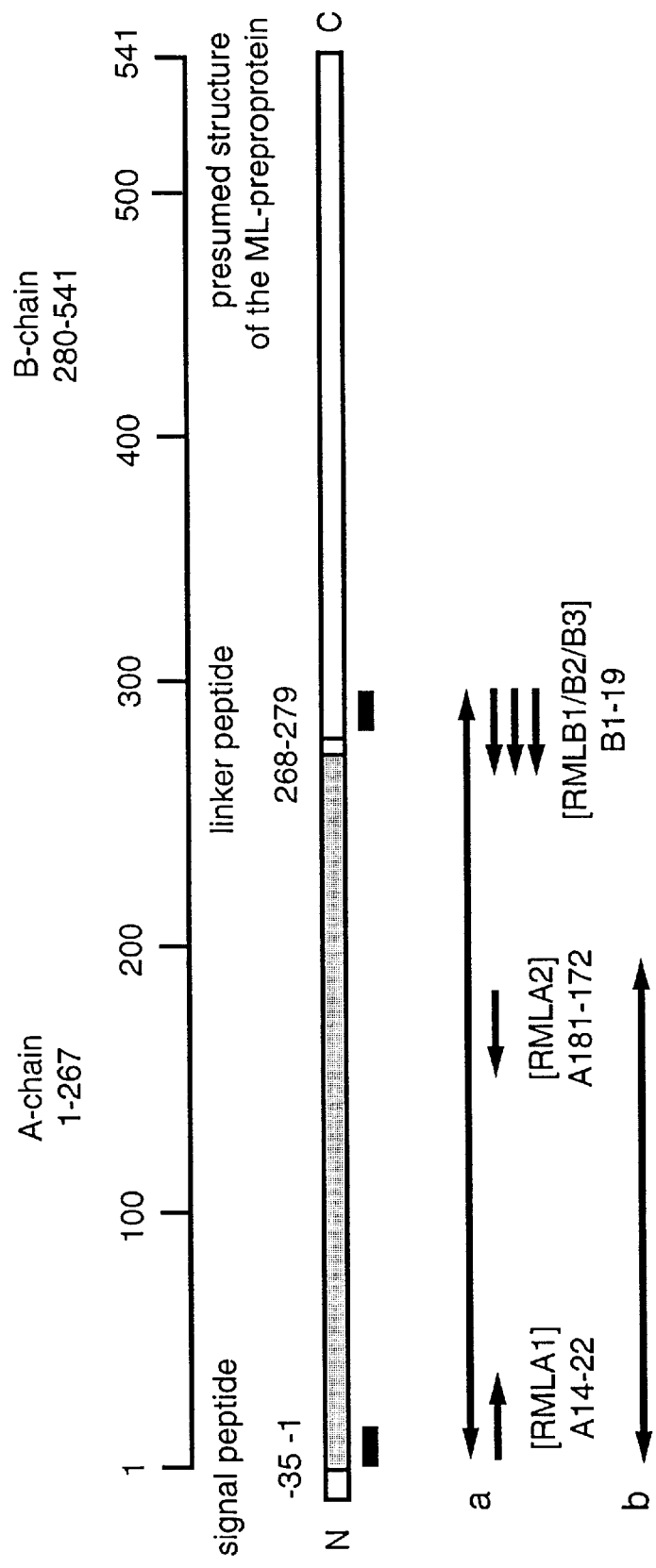
FIG. 1 (FIGS. 1a, 1b, 1c) show the construction of the primary amplification oligonucleotides (RML A1, RML B1, B2, B3, RML A2, active site regions, ribosome inactivating proteins; SEQ ID NOS:1, 2, 3, 4 and 5.

The obvious approach of screening *Viscum album* cDNA and genomic libraries, however, is completely inappropriate for finding the ML gene sequence. Despite using various DNA probes no ML specific clones could be identified in gene libraries from *Viscum album* poly-A+ RNA. Based on the assumption that the ML gene sequence does not contain introns a PCR strategy was followed. Since the N-terminal amino acid sequences were known both for MLA and MLB chain [Dietrich et al., 1992; Gabius et al., 1992], it appeared possible to amplify the MLA coding region using degenerate amplification oligonucleotides which had been derived from known peptides (FIG. 1a). While a useful oligonucleotide of low degree of degeneracy can be derived from the N-terminus of the MLA chain (RMLA1, FIG. 1b)(SEQ ID NO:1) it is not possible to construct corresponding sufficiently specific oligonucleotides from the N-terminus of the MLB chain (RMLB1, RMLB2, RMLB3, FIG. 1b)(SEQ ID NOS:3, 4 and 5).

Therefore, alternative strategies had to be developed that made it possible to derive amplification oligonucleotides from yet unknown ML sequence regions by including protein data of related proteins. An amino acid sequence analysis of type I and type II ribosome inactivating proteins showed a number of conserved regions having high sequence homology. FIG. 1c (SEQ ID NO:28) illustrates the high degree of kinship between type I and type II RIP for the active center of ricin. Within the sequence motif MIS-EAARF it was discussed with respect to E177 and R180 that they play a part in the enzymatic mechanism [Kim et al., 1992; Lord et al., 1994]. It was concluded that at least these two residues could be present in the ML sequence. Further structural deliberations with respect to the presence of individual residues—paying particular attention to those having a low degree of degeneracy of the codon usage—resulted in the construction of the amplification oligonucleotide RMLA2. The sequence of this oligonucleotide is depicted in FIG. 1c (SEQ ID NO:2).

Example 2
Preparation of ML-gene Specific DNA Fragments

High molecular, genomic DNA was isolated according to the method of Baur et al. [1993] from fresh *Viscum album* leaves (host tree *Populus wilsonii*). For the preparation of ML-gene specific DNA fragments by PCR 100 ng genomic DNA were used for each amplification reaction. Amplification was carried out in a total volume of 50 μl, containing PCR buffer (10 mM Tris-HCl, 1.5 mM MgCl$_2$, 50 mM KCl, 0.25 mM DNTP, pH 8.3), 78 pmol primer RMLA1 (SEQ ID NO:1) and 50 pmol (reaction 2) or 100 pmol (reaction 1) RMLA2 (SEQ ID NO:2). PCR was carried out with Taq DNA polymerase (1.5 U/reaction) of Boehringer Mannheim in a Biometra thermocycler. The PCR parameters were: 1 min denaturation at 90° C., 1 min annealing at 50° C., 1 min elongation at 72° C. for a total of 30 cycles. The amplification products were analyzed by 5% polyacrylamide gel electrophoresis and staining with ethidium bromide (FIG. 2). The specific amplification product obtained in reaction 2 having a size of about 500 bp was isolated by gel elution and subjected to cloning in TA vectors.

Example 3
Cloning Strategy

The derivatization of the amplification oligonucleotides used for primary PCR is shown in Example 1 (FIG. 1a), the preparation of the primary gene fragment of the *Viscum album* ML gene, referred to in the following as "a", is shown in Example 2 (FIG. 2). Starting from the sequence of the cloned gene fragment "a" and from the assumption that the ML gene does not have any introns it was possible to derive sequence-specific 5' oligonucleotides which allowed an amplification of the fragments "b", "c", "d" and "e". While the 3' oligonucleotide for "c" was also derived from the DNA sequence of "a", the degenerate 3' primer for the amplification of the gene fragments "b", "d", "e" and "g" had to be constructed by analysis of homologous regions of type I ("b") and type II ("d", "e", "g") RIP proteins. The sequence comparisons within the protein families were again used to infer the presence of individual residues, paying particular attention to those residues having a low degree of degeneracy of the codon usage. Particularly the known ricin and abrin cDNA and derived protein sequences were used to construct the about 50 ML-specific oligonucleotide combinations. FIG. 3 shows only those gene fragments that could be cloned as specific amplification products and could be subjected to further analysis. Starting from other oligonucleotide combinations no ML-specific amplification products could be generated. The preparation of the gene fragments "f" (encoding the MLA chain) and "g" (coding of the MLB chain" is described in detail in Example 5 and Example 6, respectively.

For an analysis of the 5' and 3' regions of the translated and untranslated sequence regions of the ML gene the conditions for 5' and 3' RACE [Frohman et al., 1988] were established which lead to the generation of fragments "h", "i" and "j". The amplification of fragment "j" by RACE-PCR is thus an alternative to the preparation of complete MLB gene fragments. The RACE reactions were carried out using cDNA that was prepared from isolated *Viscum album* total RNA from mistletoe leaves (host tree *Populus wilsonii*) by reverse transcription.

Example 4
DNA Sequence and Translation Products rMLA and rMLB

The inserts of expression vectors pT7-MLA SEQ ID NOS. 1 and 2 and pT7-MLB SEQ ID NOS. 3 and 4 were sequenced by standard procedures employing the "primer walking" strategy (detection of completely overlapping sequence of both strands) using various ML-specific oligonucleotides (FIGS. 4a, b) SEQ ID NOS:30, 31, 32 and 33. The underlined sequence regions refer to restriction sites for the cloning into the pT7 expression vectors. Both gene fragments have been modified according to the construction scheme of the expression vectors as described in Example 5 and Example 6. FIG. 4c (SEQ ID NOS:34 and 35) shows the complete ML gene sequence SEQ ID NOS:5 and 6 derived from the above fragments. It comprises also 5' and 3' untranslated regions as well as endopeptide and signal-peptide encoding regions.

Example 5
Construction of Expression Vector pT7-MLA

For heterologous expression the sequence encoding the mistletoe lectin A chain was prepared by specific PCR starting from complex genomic mistletoe DNA and was terminally modified. Translation control elements as well as recognition sequences of restriction endonucleases were added via the non-complementary regions of the primer oligonucleotides used, thereby allowing cloning and separate expression of the mistletoe lectin A chain on the basis of the genomic prepromistletoe lectin.

FIG. 5b shows the preparation of MLA encoding gene fragments by PCR. For an amplification of the MLA encoding gene sequence 200 ng genomic *Viscum album* DNA, 1.5 mM (reaction 1) or 2.5 mM (reaction 2) magnesium chloride, 40 pmol each of primer oligonucleotide RML16 and RML17 in PCR buffer (10 mM Tris-HCl, 50 mM KCl, 0.25 mM each of dNTP, pH 8.3) were used in a total volume of 50 μl. PCR was carried out using Taq polymerase (1.5 U/reaction, Boehringer Mannheim) by a total of 30 cycles of the temperature profile 1 min denaturation at 94° C., 1 min annealing at 52° C., 1.5 min elongation at 72° C. The amplification products were analysed by 1% agarose gel electrophoresis and staining with ethidium bromide (FIG. 5b) and provided for cloning in TA vectors by gel elution.

Figure 5:
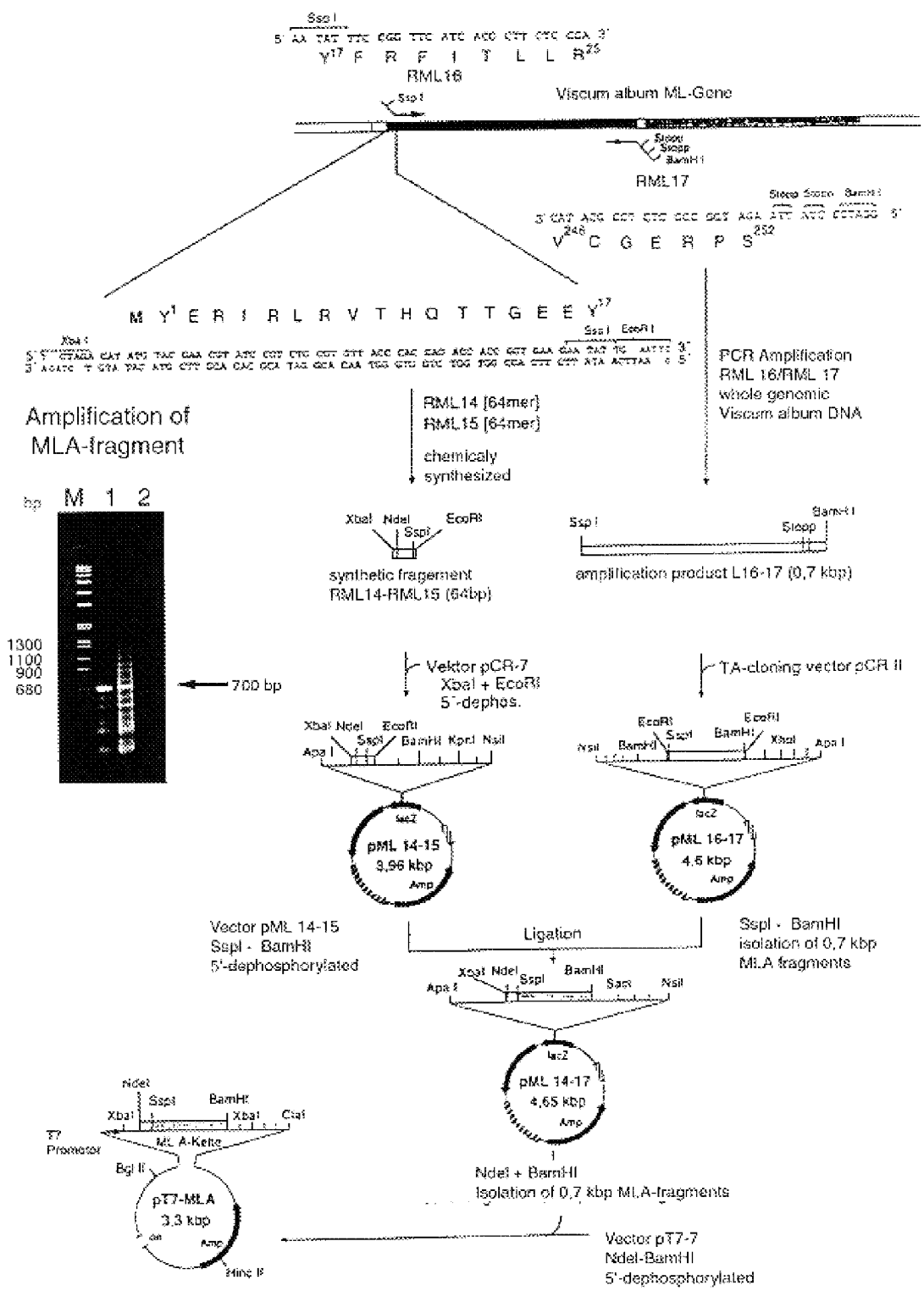
FIG. 5 shows the construction scheme for an MLA-expression vector, pT7-MLA.
Figure 6:
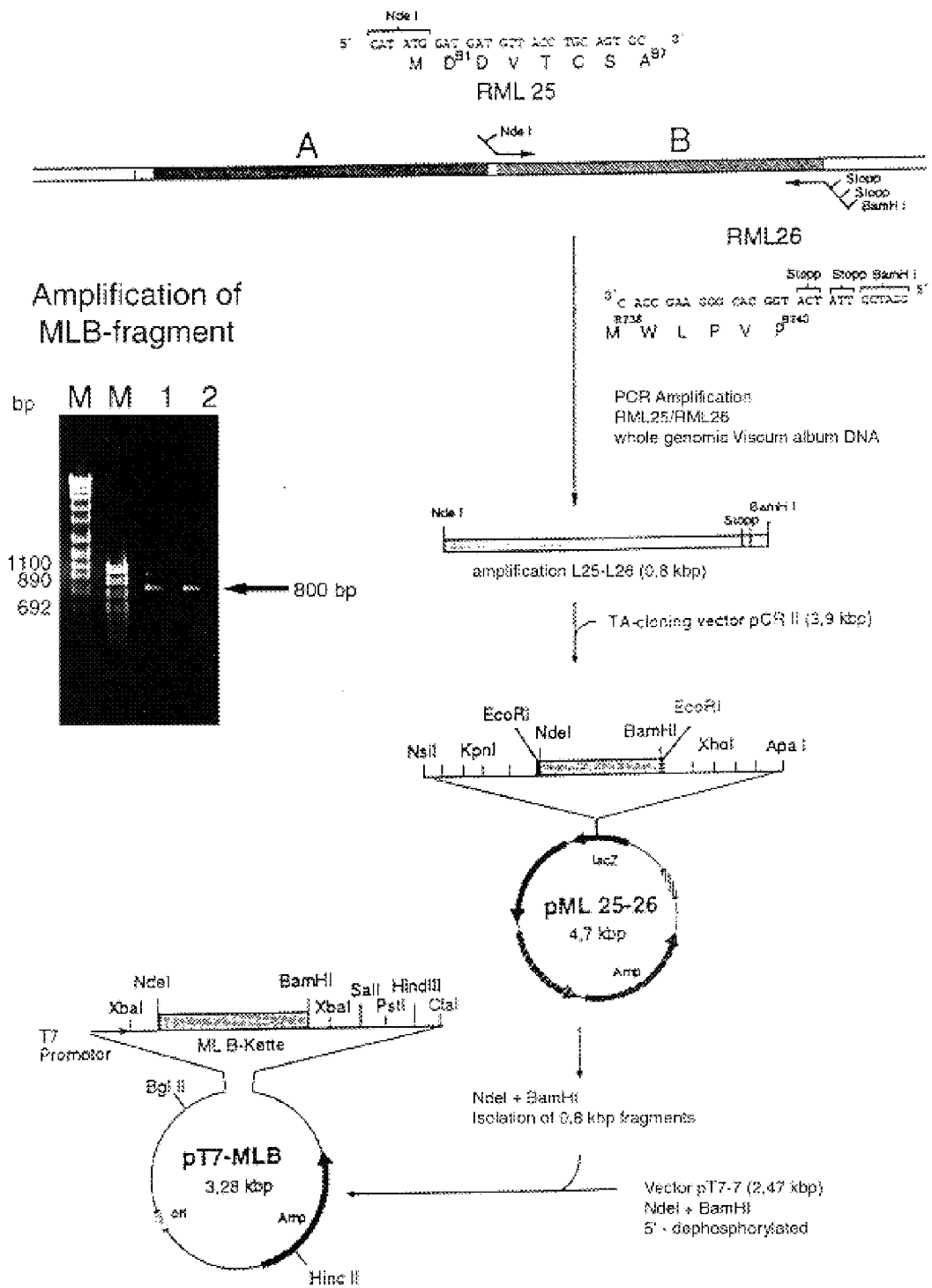
FIG. 6 shows the construction scheme for an MLB-expression vector, pT7-MLB.

The 5' region of the sequence encoding rMLA corresponding to the amino acid residues tyrosine[1]–tyrosine[17] [Dietrich et al., 1992; Gabius et al., 1992] was prepared as a synthetic gene fragment by hybridization and cloning of two oligonucleotides and by addition of a translation start codon. In this way, the gene sequence was optimized as regards the codon choice such as described for strongly expressed genes in *Escherichia coli* [Gribskov et al., 1984]. At the 3' end of the synthetic rMLA gene fragment as well as at the 5' end of the rMLA gene fragment obtained by PCR an Ssp I restriction site was introduced by the specific exchange of the tyrosine[17] codon from TAC to TAT which restriction site allowed fusion of the two rMLA gene fragments while obtaining vector pML14–17 (FIG. 5).

The complete generated sequence encoding rMLA was confirmed by DNA sequencing (FIG. 4a). For expression of rMLA in *Escherichia coli* the gene sequence was isolated from vector pML14–17 and was put under the control of the T7-RNA polymerase promoter and a transcription terminator by insertion into expression vector pT7-7. The resulting expression vector pT7-MLA (FIG. 5) was used to transform the *E. coli* expression strain BL21.

Example 6
Construction of Expression Vector pT7-MLB

For heterologous expression of the mistletoe lectin B chain the complete sequence encoding MLB was amplified from complex genomic *Viscum album* DNA by specific PCR, introducing translation control elements as well as recognition sequences for restriction endonucleases via non-complementary regions of the primer oligonucleotide used.

FIG. 6*b* shows the preparation of the entire gene fragment completely encoding rMLB by PCR. The amplification of the rMLB encoding DNA fragment was carried out in PCR reactions in a total volume of 50 μl PCR buffer (10 mM Tris-HCl, 50 mM KCl, 1.5 mM $MgCl_2$, 0.25 mM each of dNTP, pH 8.3) with 200 ng genomic *Viscum album* DNA and 50 pmol primer oligonucleotide RML25 and 30 pmol (reaction 1) and 10 pmol (reaction 2) of primer oligonucleotide RML26. PCR was carried out using Taq polymerase (1.5 U/reaction, Boehringer Mannheim) by a total of 30 cycles of 1 min denaturation at 94° C., 1 min annealing at 52° C. and 1.5 min elongation at 72° C. The PCR products were analysed by 1% agarose gel electrophoresis and staining with ethidium bromide. The result was a 0.8 kbp PCR product which was isolated by gel elution and provided for cloning in TA vectors. The rMLB encoding gene fragment was put under the control of transcription control elements by insertion into expression vector pT7-7 and the expression strain *E. coli* BL21 was transformed with the resulting expression vector pT7-MLB. Integrity of the PCR-generated, complete sequence encoding rMLB was confirmed by DNA sequencing (FIG. 4*b*).

Example 7

Expression, Immunological Analysis, Refolding and in vitro Reassociation of rMLA and rMLB (I) Expression of rMLA in *E. coli*

For an expression of recombinant mistletoe lectin A chain 1000 ml $LB_{Amp}$ medium were inoculated into 2 l grooved tissue culture flasks with 5 ml of a stationary grown $LB_{Amp}$ preculture of *E. coli* BL21/pT7-MLA and cultivated at 37° C. under shaking. Growth was observed by turbidimetry at 578 nm. Gene expression was induced by adding 0.5 mM IPTG when a cell density of $OD_{578}$≈0.9–1.0 was reached. For harvesting, the cells were sedimented 2 hrs after induction by centrifugation at 5,000 rpm for 20 min and 4° C. in a GS-3 rotor (Sorvall) and the culture medium was decanted. Starting from 1 l culture volume, a cell mass of 3–4 g (wet weight) was isolated.

Cell disruption was carried out using a French-Press (SML Instruments). The cell sediment was resuspended in 20 ml disruption buffer B (50 mM Tris-HCL, 100 mM NaCl, 1 mM EDTA, 5 mM DTT, 1 mM PMSF, pH 8.0) and disrupted by 2 French-Press steps at 1,500 psi. Insoluble cell fractions and possible "inclusion bodies" were sedimented by subsequent centrifugation at 10,000 rpm for 30 min and 4° C. in a SS-34 rotor (Sorvall) and separated from the soluble *E. coli* proteins or soluble expression product remaining in the supernatant.

For an analysis of the expression equal volumina of the cell disruption fractions were examined by 12.5% SDS polyacrylamide gel electrophoresis and staining with Coomassie Brilliant Blue as well as by Western blot using the MLA specific antiserum TA5 (FIG. 7*a*). The monoclonal antibodies TA5 [Tonevitsky et al., 1995] were provided by the author. Like the other antibodies used in the present invention they can be prepared by standard techniques using the respective immunogen (in the case of TA5 it is ML-1 or MLA). For detection of the expression equal volumina of the soluble fractions (lane 2, 4, 6, 8) as well as of the insoluble "inclusion bodies" fraction (lane 1, 3, 5, 7) of the *E. coli* disruption were examined for their rMLA content. In order to illustrate the course of the expression, samples before (lane 1+2), 2 hrs (lane 3+4), 4 hrs (lane 5+6) and 6 hrs (lane 7+8) after induction of gene expression were used. Expression is characterized already 1 hr after induction by the occurrence of an immune-reactive 25 kDa expression product corresponding to rMLA, whose expression maximum is reached already after 2 hrs after induction. The distribution of rMLA over the soluble and insoluble cell discruption fraction 2 hrs after induction is ~50% each, with a longer expression duration resulting in an increase in formation of insoluble "inclusion bodies".

(II) Isolation of rMLA from Insoluble "Inclusion Bodies"

The sediment of the *E. coli* complete cell disruption was washed twice with 20 ml STET-buffer each (50 mM Tris-HCl, 8% (w/v) sucrose, 50 mM EDTA; 1.5% (v/v) triton X-100, pH 7.4) according to Babitt et al. [1990] to remove *E. coli* proteins. The remaining sediment with the "inclusion bodies" contained therein was dissolved in 20 ml denaturation buffer (6 M guanidiniumchloride, 100 mM DTT, 50 mM Tris-HCl, pH 8.0) by incubation for 16 hrs at room temperature under constant agitation.

For renaturation of rMLA the protein solution present in the denaturation buffer was slowly and dropwise added to the 90-fold volume of folding buffer (50 mM Tris-HCl, 2 mM DTT, 1 mM EDTA, pH 8.0) and incubated for 16 hrs at room temperature while stirring it. Precipitated protein was separated by centrifugation at 6,000 rpm for 30 min and 4° C. in a GS-3 rotor (Sorvall). The rMLA containing supernatant was adjusted for storage to 20% (v/v) glycerol and stored at 4° C.

(III) Purification of rMLA by Immunoaffinity Chromatography

For a 1-step purification of rMLA (soluble expression product fraction or refolded protein) by immunoaffinity chromatography 260 μg of the monoclonal antibody anti-nMLA-IgG (TA5, Tonevitsky et al., 1995) directed against the mistletoe lectin A chain were covalently immobilized on protein A sepharose CL4B (Sigma, Deisenhofen) according to the method by Harlow & Spur [1988]. After incubation of the immunoaffinity matrix with the rMLA sample and after washing the matrix with 10 column bed volumes of washing buffer 1 (1 M NaCl, 10 mM phosphate buffer, pH 7.0) and 10 column bed volumes of washing buffer 2 (10 mM phosphate buffer, pH 7.0) to remove unspecifically bound proteins specifically bound rMLA was eluted with elution buffer (0.1 M glycine, pH 2.5). Elution was performed to readjust the pH in a receptacle containing 1 M phosphate buffer, pH 8.0.

(IV) Expression of rMLB in *E. coli*

For an expression of recombinant mistletoe lectin B chain 1000 ml $LB_{Amp}$ medium were inoculated into 2 l grooved tissue culture flasks with 5 ml of a stationary grown $LB_{Amp}$ preculture of *E. coli* BL21/pT7-MLB and cultivated at 37° C. under shaking. Growth was observed by turbidimetry at 578 nm. Gene expression was induced by adding 0.5 mM IPTG when a cell density of $OD_{578}\approx 0.9–1.0$ was reached. For harvesting, the cells were sedimented 4 hrs after induction by centrifugation at 5,000 rpm for 20 min and 4° C. in a GS-3 rotor (Sorvall) and the culture medium was decanted.

The cells were disrupted using a French-Press™ (SLM Instruments). The cell sediment was resuspended in 20 ml disruption buffer B (20 mM phosphate buffer, 50 mM NaCl, 1 mM EDTA, 1 mM PMSF, pH 7.2) and broken up by 2 French-Press steps at 1,500 psi. Insoluble cell fractions and possible "inclusion bodies" were sedimented by subsequent centrifugation at 10,000 rpm for 30 min and 4° C. in a SS-34 rotor (Sorvall) and separated from the soluble *E. coli* proteins or soluble expression product remaining in the supernatant.

For an analysis of the expression equal volumina of the cell disruption fractions were examined by 12.5% SDS polyacrylamide gel electrophoresis and staining with Coomassie Brilliant Blue as well as by Western blot using the MLB-specific antiserum TB33 (FIG. 7*b*). The monoclonal antibodies TB33 [Tonevitsky at al., 1995] were provided by the author. They were prepared using standard techniques. Corresponding antibodies can be prepared by the person skilled in the art by standard techniques employing ML-1 or MLB as immunogen. For an analysis of the expression equal volumina of the soluble fraction (lane 2, 4, 6, 8) as well as of the insoluble "inclusion bodies" fraction (lane 1, 3, 5, 7) of the *E. coli* were examined for their rMLB content. In order to illustrate the course of the expression, samples before (lane 1+2), 2 hrs (lane 3+4), 4 hrs (lane 5+6) and 6 hrs (lane 7+8) after induction of gene expression were used. Expression is characterized already 1 hr after induction by the occurrence of an immune-reactive 31 kDa expression product corresponding to rMLB, whose expression maximum is reached after 4 hrs after induction. The distribution of rMLB over the soluble and insoluble cell disruption fraction 4 hrs after induction is ~50% each, with a longer expression duration resulting in an accumulation of expressed rMLB in the form of insoluble "inclusion bodies".

(V) Isolation of rMLB from Insoluble "Inclusion Bodies"

The sediment of the *E. coli* complete cell disruption was washed twice with 20 ml STET-buffer each (50 mM Tris-HCl, 8% (w/v) sucrose, 50 mM EDTA; 1.5% (v/v) triton X-100, pH 7.4) according to Babitt et al. [1990] to remove *E. coli* proteins. The remaining sediment with the "inclusion bodies" contained therein was dissolved in 20 ml denaturation buffer (6 M guanidiniumchloride, 100 mM DTT, 50 mM Tris-HCl, pH 8.0) by incubation for 16 hrs at room temperature while shaking it.

For renaturation of rMLB the protein solution present in the denaturation buffer was slowly and dropwise added to the 90-fold volume of folding buffer (20 mM phosphate buffer, 50 mM KCl, 1 mM EDTA, 100 mM glucose, 10% (v/v) glycerol, 10 mM β-lactose, pH 5.5) and incubated for 16 hrs at room temperature while stirring it. Precipitated protein was separated from the soluble, folded rMLG fraction by centrifugation at 6,000 rpm for 30 min and 4° C. in a GS-3 rotor (Sorvall).

(VI) Isolation of rMLB by Affinity Chromatography on N-acetyl-D-galatosamine Agarose In order to isolate active, carbohydrate-binding rMLB, an N-acetyl-galactosamine agarose affinity matrix (PIERCE, USA) was equilibrated with 10 column bed volumina chromatography buffer (50 mM phosphate buffer, 300 mM NaCl, 1 mM EDTA, 10% (v/v) glycerol, 0.05% (v/v) Tween®-20, pH 7.0). The application of the samples was carried out by batch incubation of the affinity matrix in an rMLB-containing sample solution for at least 2 hrs at 4° C. After washing the affinity matrix with chromatography buffer to remove unspecifically bound proteins bound rMLB was eluted by competitive displacement with 0.3 M N-acetyl-galactosamine in chromatography buffer, pH 4.0.

(VII) In vitro Reassociation of Mistletoe Lectin Chains to Prepare the Holoprotein Recombinant mistletoe lectin holoprotein (rML) can be prepared starting from isolated, folded mistletoe lectin A and mistletoe lectin B chains or starting from denatured ones which were renatured by co-folding. For reassociation of isolated, folded single-chains, isolated mistletoe lectin B chain (nMLB or rMLB) was incubated with a molar excess of rMLA in 20 mM phosphate buffer, 50 mM NaCl, 1 mM EDTA; pH 7.2 at 4° C. for 16–48 hrs. For the interchain disulfide bridges to form, the reaction was incubated in the presence of a redox system of 6 mM glutathione (ratio of reduced to oxidized 5:1) or 10 mM glutathione (ratio of reduced to oxidized 2:1)+1 μM protein disulfide isomerase (Boehringer Mannheim). For reassociation starting from denatured single-chains by co-folding, rMLA chain was dissolved in 6 M guanidinium chloride, 2 mM DTT, 50 mM Tris-HCl, pH 8.0 to a concentration of 2 mg/ml. To completely reduce the cystein residues the rMLB chain was dissolved in 6 M guanidinium chloride, 100 mM DTT; 50 mM Tris-HCl, pH 8,0 and rebuffered after incubation at room temperature for 20 min on 6 M guanidinium chloride, 50 mM Tris-HCl, pH 8.0 by gel permeation on PD-10 (Pharmacia, Sweden) and adjusted to a concentration of 200 μg/ml. Reassociation was carried out by co-folding of rMBL with a molar excess of rMLA by slowly diluting the guanidinium solution by 1:30 in coupling buffer (50 mM sodium phosphate buffer, 50 mM KCl, 1 mM EDTA; 10% (v/v) glycerol, 100 mM glucose, 20 mM lactose, pH 8.0) and incubation at 4° C. for 16 hrs. For the interchain disulfide bridges to form, the reaction was incubated in the presence of a redox system of 2 mM glutathione (ratio of reduced to oxidized 1:1).

The coupling reactions were dialysed against storage buffer (50 mM sodium phosphate buffer, 300 mM NaCl, 1 mM EDTA, 10% (v/v) glycerol, 0.05% (v/v) Tween®-20, pH 8.0). Assay and identification of the heterodimer formed was carried out by SDS-PAGE under non-reducing conditions and subsequent Western blot analysis using specific, monoclonal antibodies against mistletoe lectin A chain (TA5) or mistletoe lectin B chain (TB33). Isolation of the holoprotein formed or separation of free rMLA or rMLA aggregates was carried out by affinity chromatography on N-acetyl-galactosamine sepharose or lactosyl-agarose as described in (VI).

Example 8
Isoelectric Homogeneity of rMLA and rMLB

1–2 µg rMLA, naturally occurring MLA, rMLB, naturally occurring MLB or ML holoprotein were focused together with IEF protein standards (BioRad, USA) on Servalyt PreNets IEF-gels (pH 3–10, 125×125 mm, 150 µm, Serva Heidelberg). For analysis the proteins were immobilized by semi-dry electroblotting on nitrocellulose membranes (0.2 µm, Schleicher & Schüll, Dassel). Immunological staining was performed using a monoclonal MLA-specific antibody (TA5, Tonevitsky et al., 1995) for rMLA and nMLA or using a monoclonal MLB-specific antibody (TB33, Tonevitsky et al., 1995) for rMLB, nMLB and ML holoproteins. Immune complexes were stained using an anti-mouse IgG-IgG (Sigma, Deisenhofen) conjugated with alkaline phosphatase and reacting the substrates NBT and BCIP (FIG. 8).

Figure 8:
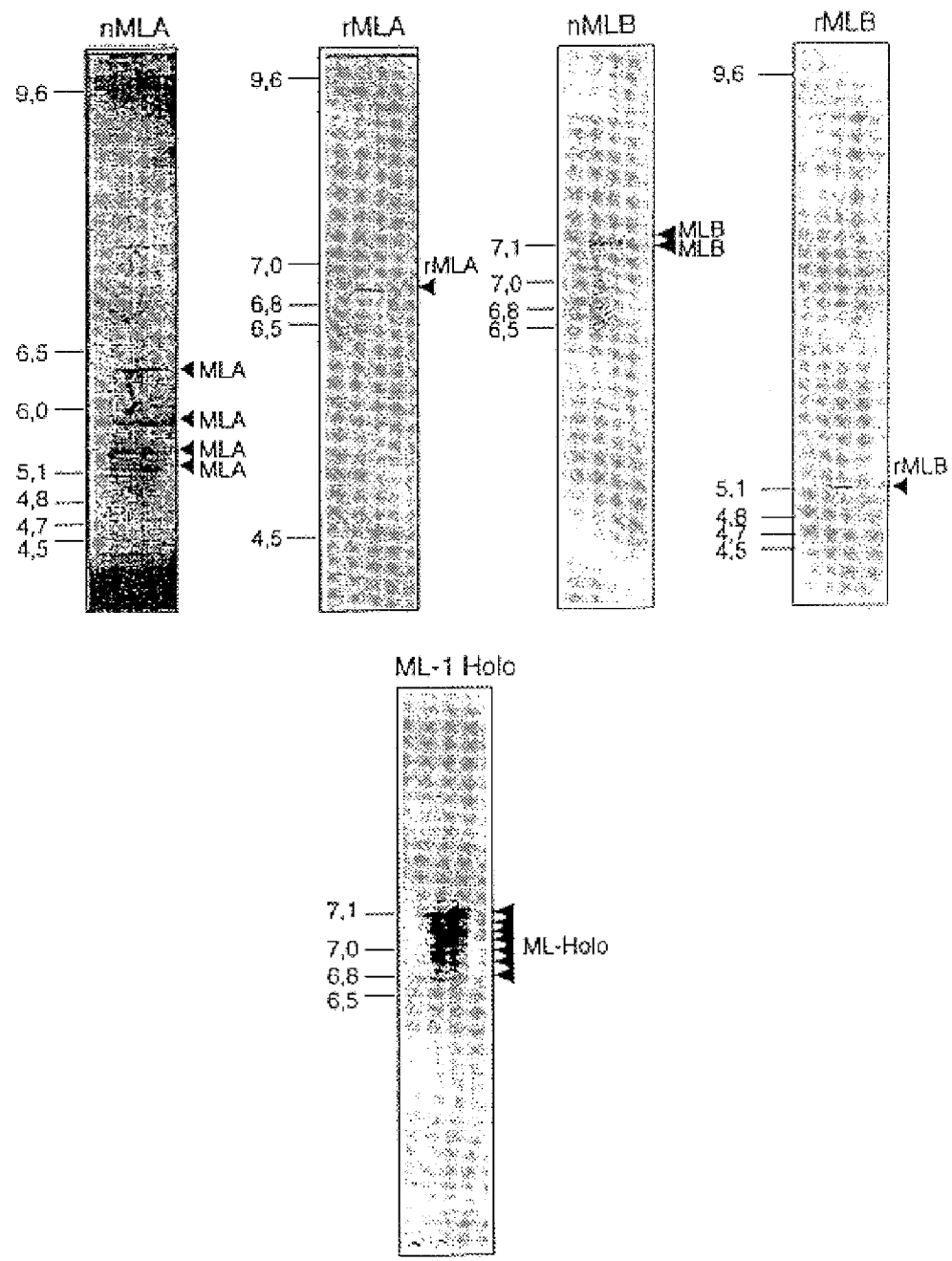
FIG. 8 shows IEF chromatofocusing of rMLA and rMLB vs. natural ML (nML)

While highly purified plant mistletoe lectin A chain as well as highly purified mistletoe lectin B chain are isoelectrically inhomogeneous proteins with isoelectric points of the nMLA of 5.2:5.4:5.5:6.2 and of the nMLB of 7.1:7:3, the recombinant rMLA chain having an isoelectric point of 6.8 and the recombinant rMLB chain having an isoelectric point of 5.1 is a homogeneous protein (FIG. 8). Thus, there is a large heterogeneous number of molecule variants for the naturally occurring ML holoprotein (FIG. 8, bottom) while the uniform mobility of recombinant mistletoe lectin proteins reveals the homogeneity of the rML vis-à-vis the microheterogeneity of the plant mistletoe lectins.

Example 9
Detection of the Enzymatic, Ribosome-inactivating Activity of rMLA The protein concentration of rMLA (refolded) and rMLA (soluble) purified by immunoaffinity chromatography as well as of naturally occurring MLA chain (nMLA) was determined according to Bradford [1976] using a BSA standard.

For the detection and quantification of the enzymatic rRNA-N-glycosidase activity of MLA a non-radioactive test system was established by using the "TNT coupled reticulocyte system" (Promega, USA). Per reaction, equal amounts (20 µl) of the TNT system were preincubated at 30° C. for 15 min. For the quantification of the translation inhibition 2 µl of the corresponding buffer were added to the control reactions and 2 µl of gradient MLA dilutions (concentration range 350–0 pM) to the test reactions. From each reaction 2 samples were taken at intervals of 8 min and frozen in liquid nitrogen to stop the reaction. As a measure of the translation activity the relative luciferase amount (sqrt-cpm) was determined in a bioluminescence test by a scintillation counter. For each reaction the difference of the sqrt-cpms measured of the samples which were taken at different times was determined as measure of the relative translation activity. The activity in the control reaction without RIP was set to 0% inactivation rate (IAR).

By applying the relative translation inactivation rate against the rMLA concentrations used the protein concentration was determined by non-linear regression that results in a 50% inhibition of translation activity as compared to the control reaction. This $IC_{50}$ value is a system-dependent value which allows detection and quantification of the enzymatic activity of rMLA (soluble), rMLB (refolded) vis-à-vis nMLA (FIG. 9).

Figure 9:
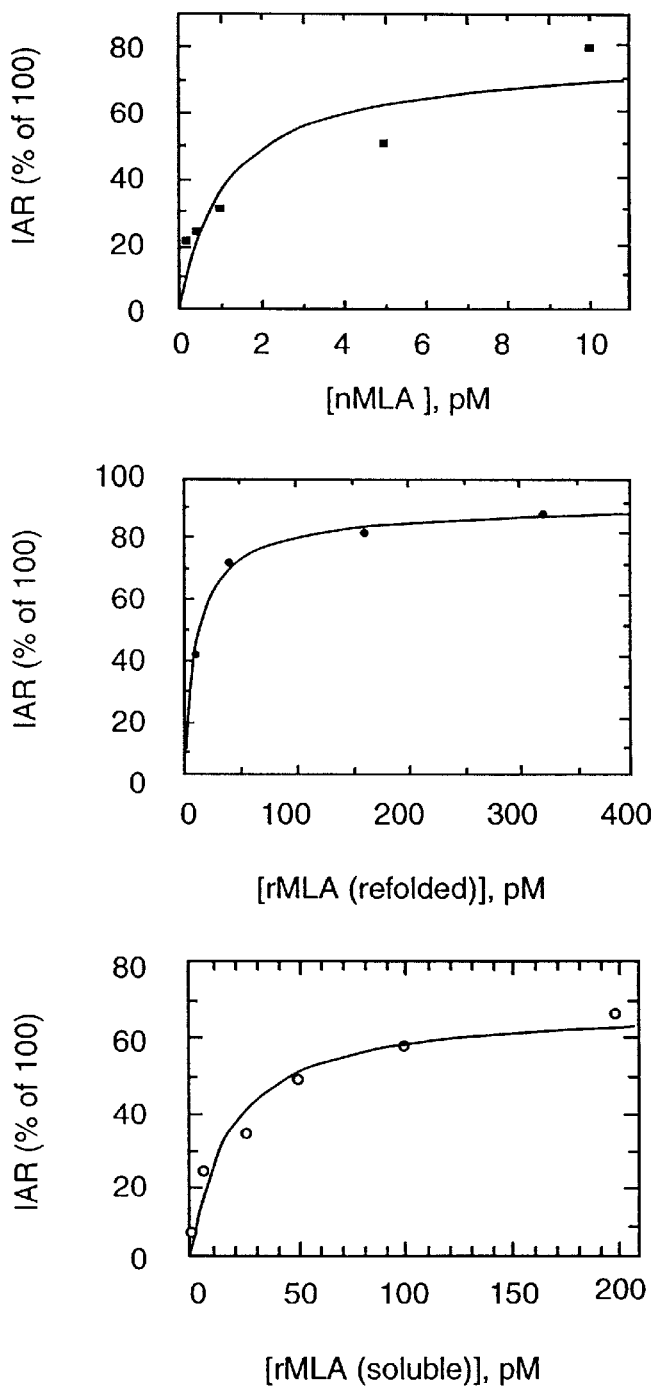
FIG. 9 shows enzymatic acitivity of rMLA (RIP)

FIG. 9 shows the detection of the enzymatic, ribosome-inactivating activity of the recombinant MLA chain. Both by isolation of the soluble expression product content (rMLA soluble) and by refolding of the protein (rMLA refolded) isolated from "inclusion bodies" an enzymatically active expression product can be obtained. rMLA (soluble) and rMLA (refolded) exhibit corresponding activities with $IC_{50}$ values of 10.7±1.3 pM or 15.6±6.6 pM. They thus exhibit a lower toxic activity than the naturally occurring MLA chain ($IC_{50}$ 1.1±0.7 pM).

Example 10
Carbohydrate-binding Activity of the Mistletoe Lectin B Chain

Detection of the carbohydrate-binding activity of the recombinant mistletoe lectin B chain as well as the comparison of the carbohydrate-binding activities and specificities of recombinant and plant mistletoe lectin B chain is carried out by Enzyme Linked Lectin Assay (ELLA) in the presence of competitive carbohydrates. The linkage of the nMLB and rMLB chains was established by using an immobilized asiolofetuin matrix to preponderantly galactose and N-acetyl-galactosamine residues as well as by using an immobilized fetuin matrix to preponderantly sialic acid residues.

For an immobilization of the carbohydrate matrix 100 µl of an 1.1 mg asiolofetuin (Sigma, Deisenhofen) or 1.1 mg fetuin (Sigma, Deisenhofen) solution in 11 ml PBS was transferred to the wells of MaxiSorp C96 mictrotiter plates (Nunc, Wiesbaden) and incubated at room temperature for 16 hrs. After washing the microtiter plates 3 times with 150 µl/well PBS-T (10 mM sodium phosphate buffer, 130 mM NaCl, 0.1 % (v/v) Tween®-20, pH 7.2) the microtiter plates were incubated at 36° C. for 1 hr with 200 µl/well PBS-T-1% BSA (10 mM sodium phosphate buffer, 130 mM NaCl, 0.1% (v/v) Tween®-20, 1% (w/v) BSA, pH 7.2) to block unspecific binding sites and were then washed as described above. For testing 100 µl B-chain containing preparations were used in a concentration of 100–500 ng/ml, preferably of 400 ng/ml. The test concentrations were adjusted by dilutions of the samples in PBS-0,05% BSA (10 mM sodium phosphate buffer, 130 mM NaCl, 0.05% (w/v) BSA, pH 7.2). Per test concentration and control 2–3 replicas were prepared. Determination of the control is carried out with PBS-0.05% BSA or the respective preparation buffer. In order to determine the binding specificities, the samples were incubated in the presence of free, competitive sugars. For a displacement of rMLB, nMLB or ML holoproteins from the binding to the asialofetuin or fetuin matrix, galactose preferably in the concentration range of from 0–280 mM, N-acetyl-galactosamine in the concentration range of from 0–280 mM, lactose in the concentration range of from 0–140 mM or sialic acid in the concentration range of from 0–140 mM was used. The plates were incubated at 36° C. for 2 hrs after loading and were then washed as described above. To the loaded well 100 µl/well goat anti-mistletoe lectin serum (1:19800 dilution of the serum pool in PBS-T-0.1% BSA-Tx (10 mM sodium phosphate buffer, 130 mM NaCl, 0.1% (v/v) Tween®-20, 0.1(w/v) BSA, 1% (v/v) Triton® X100, pH 7.2) were added, incubated at 36° C. for 2 hrs and then washed as described above. For an assay of the immune complexes per loaded well 100 µl anti-goat IgG-IgG, conjugated with horseradish peroxidase (Sigma, Deisenhofen) were added to a 1:3500 dilution in PBS-1% BSA (10 mM sodium phosphate buffer, 130 mM NaCl, 1% (w/v) BSA; pH 7.2) and incubated at 36° C. for 1 hr. The wells were then washed 6 times with 150 µl/well PBS-T. For development, 100 µl/well substrate solution (1 o-phenylene diamine tablet (Sigma, Deisenhofen) in 25 ml 65 mM citric acid, pH 5.0+10 µl 30% hydrogen peroxide) were added and incubated at room temperature for 20 min in the dark. The reaction was stopped by adding 100 µl/1 M sulphuric acid/well. Evaluation was made by absorption photometry at 450 nm with a reference wavelength of 690 nm and calculation of the IC50 value by description of the measured data by a 4-Parameter Fit.

Figure 10:
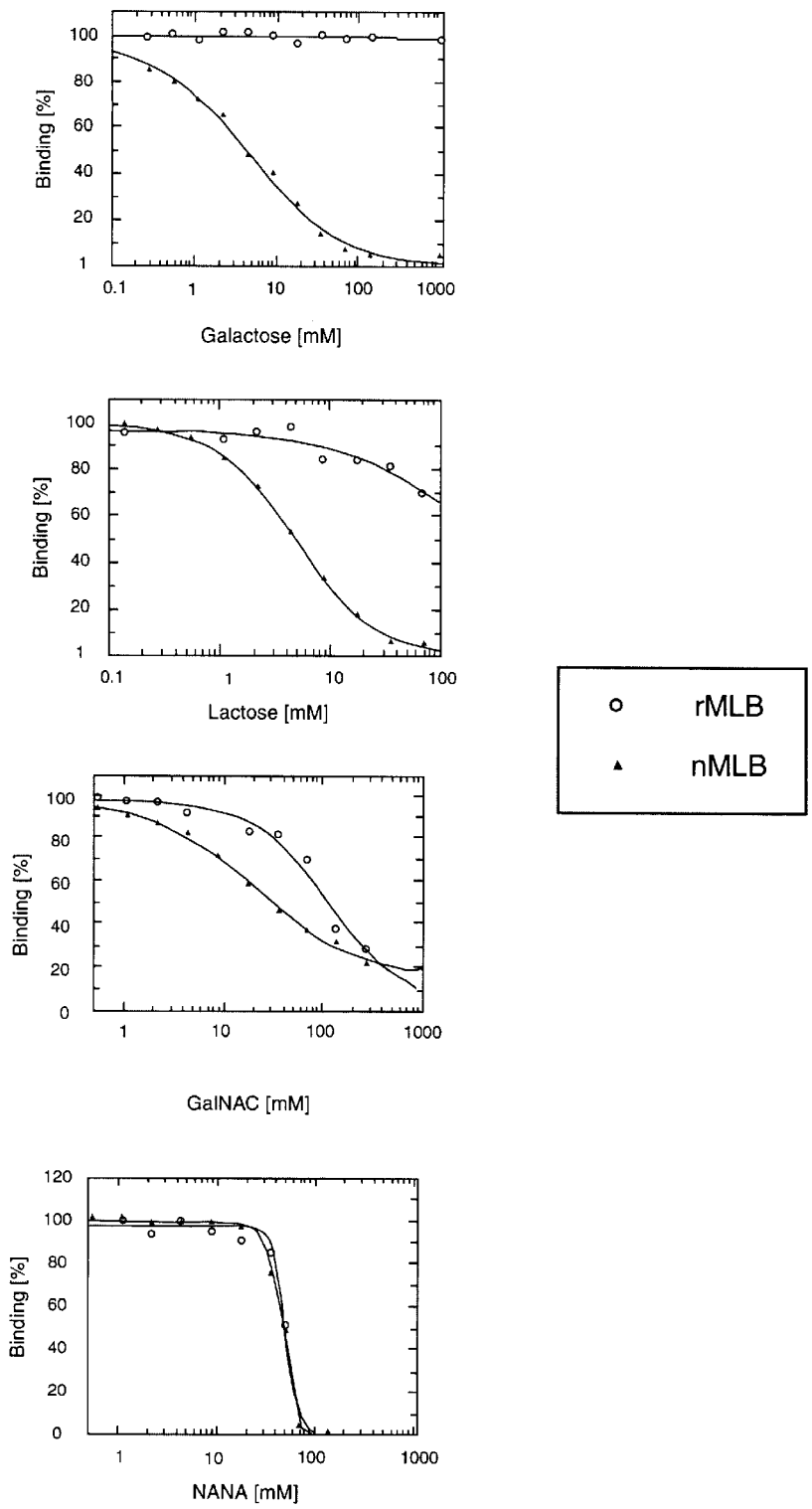
FIG. 10 shows carbohydrate-binding characteristics of rMLB and nML.
Figure 11:
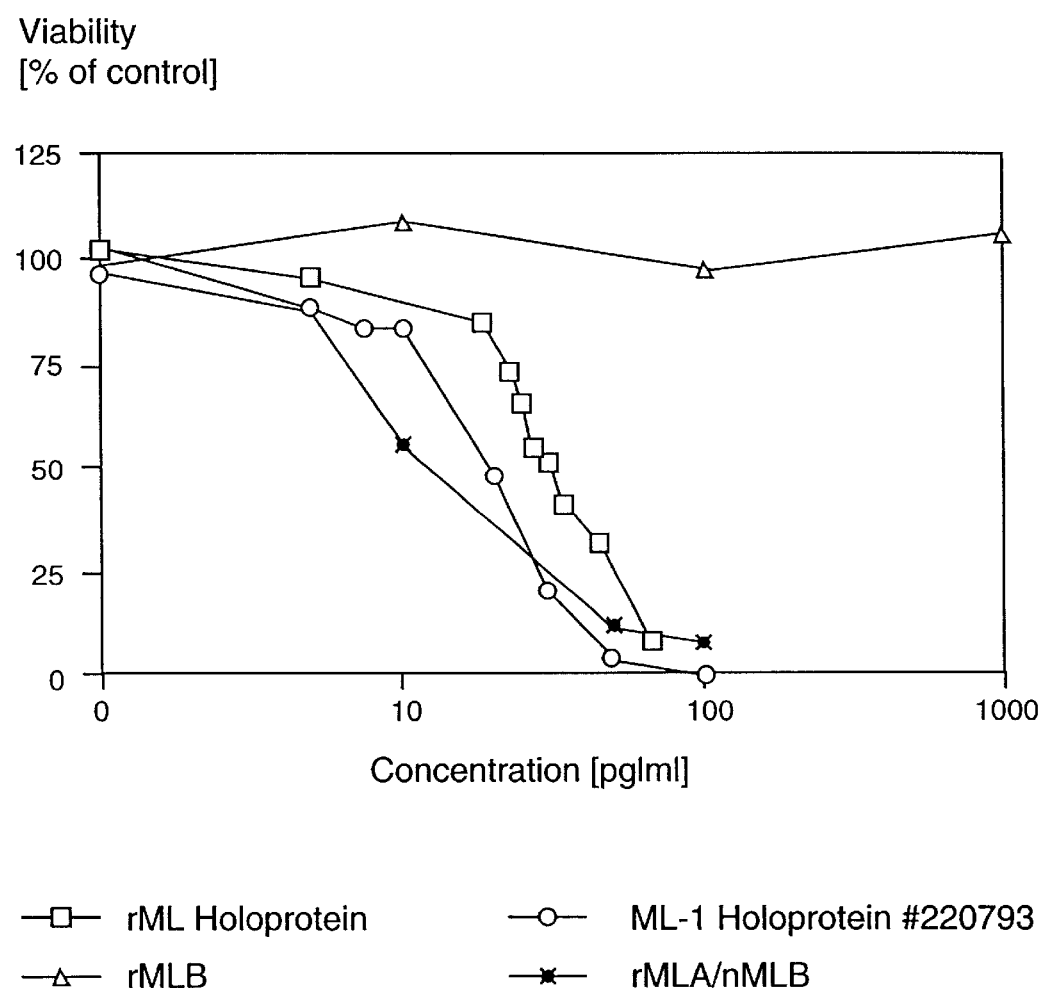
FIG. 11 shows MOLT4 cytotoxicity of rML.

FIG. 10 shows the values of the displacement of rMLB and nMLB from the immobilized asiolofetuin ligand by increasing amounts of D-galactose (FIG. 10a), β-lactose (FIG. 10b) or N-acetyl-galactosamine (FIG. 10c) as well as of the displacement of the immobilized fetuin ligands by increasing amounts of sialic acid (FIG. 10d) which were observed in the ELLA system. The binding characteristics of nMLB and rMLB are described by the IC50 value in relation to the semi-maximal displacement. While the carbohydrate binding of the plant nMLB chain can be mainly competed by galactose (IC50=4.5 mM) and β-lactose (IC50=4.9 mM) the recombinant rMLB chain surprisingly has a clearly altered carbohydrate specificity. In contrast to the nMLB the carbohydrate-binding activity of rMLB cannot be competed by galactose (IC50 not determinable) and only to a restricted extent by β-lactose (IC50>70 mM). Apart from the dramatically reduced affinity vis-à-vis galactose and β-lactose the recombinant rMLB chain has a marked specificity for N-acetyl-galactosamine (IC50=109 mM). Another activity of the binding to sialic acid ligands which was described for nMLB could also be detected for the recombinant MLB chain (FIG. 10d). For the plant nMLB chain (IC50=49.8 mM) and the recombinant rMLB chain (IC50=47.1 mM) identical binding affinities were detected. Vis-à-vis the plant, mainly galactose/β-lactose-specific nMLB chain the recombinantly prepared rMLB chain has a clearly distinct carbohydrate specificity which is shifted to direction of the N-acetyl-galactosamine/sialic acid binding.

Example 11
Detection of the Cytotoxicity of in vitro Reassociated rML Holoproteins on Human Lymphatic Leukemia Cells The integrity of the mistletoe lectin holoprotein was detected by quantitative analysis of the cytotoxicity vis-à-vis the human mononuclear (lymphatic) leukemia cell line MOLT-4 (European Collection of Animal Cell Cultures No. 85011413). MOLT-4 cells were cultivated in serum-free MDC-1 medium (PAN SYSTEMS, Aidenbach) and adjusted for the test to a cell density of $1.5 \times 10^5$ MOLT-4 cells/ml at a viability of >98%. In order to determine the cytotoxicity, per well of a 96-well microtiter plate 90 μl of a MOLT-4 cell suspension corresponding to 18000 cells/well were added and mixed with 10 μl of the sample solution. For the test, mistletoe lectin holoprotein preparations (batches #220793 (Madaus) and BRAIN 12/94 which were isolated from mistletoe leaves or mistletoe tea by standard techniques using lactosyl sepharose [Franz et al., 1977]) as well as in vitro reassociated rML holoprotein in a concentration range of 1–100 pg/ml were correspondingly used (1.6 fM-1.66 pM), with the dilution series being prepared in MDC-1 cell culture medium. Per sample concentration and control 6 replicas were prepared. The cells were incubated in an incubator at 37° C. and 5% $CO_2$ for 72 hrs. Quantification of the cytotoxic effect was carried out by determining the viability of the cells using a soluble formazan dye according to the WST-1 method [Scudiero et al., 1988] using the corresponding Cell Proliferation Reagent WST-1 (Boehringer Mannheim). The recombinant holoprotein as well as the chimeric holoprotein rMLB/nMLB show identical biological activity vis-à-vis the naturally occurring protein with IC50 values around 10–30 pg/ml as regards the MOLT4-cytotoxicity. In the tested concentration range (rMLB up to 1 ng/ml), however, rMLB does not show cytotoxic activity.

Example 12
Induction of Apoptosis Shown for the Example of Human Monocyte Cell Line U937 by Recombinant Mistletoe Lectin (rML)

Figure 12:
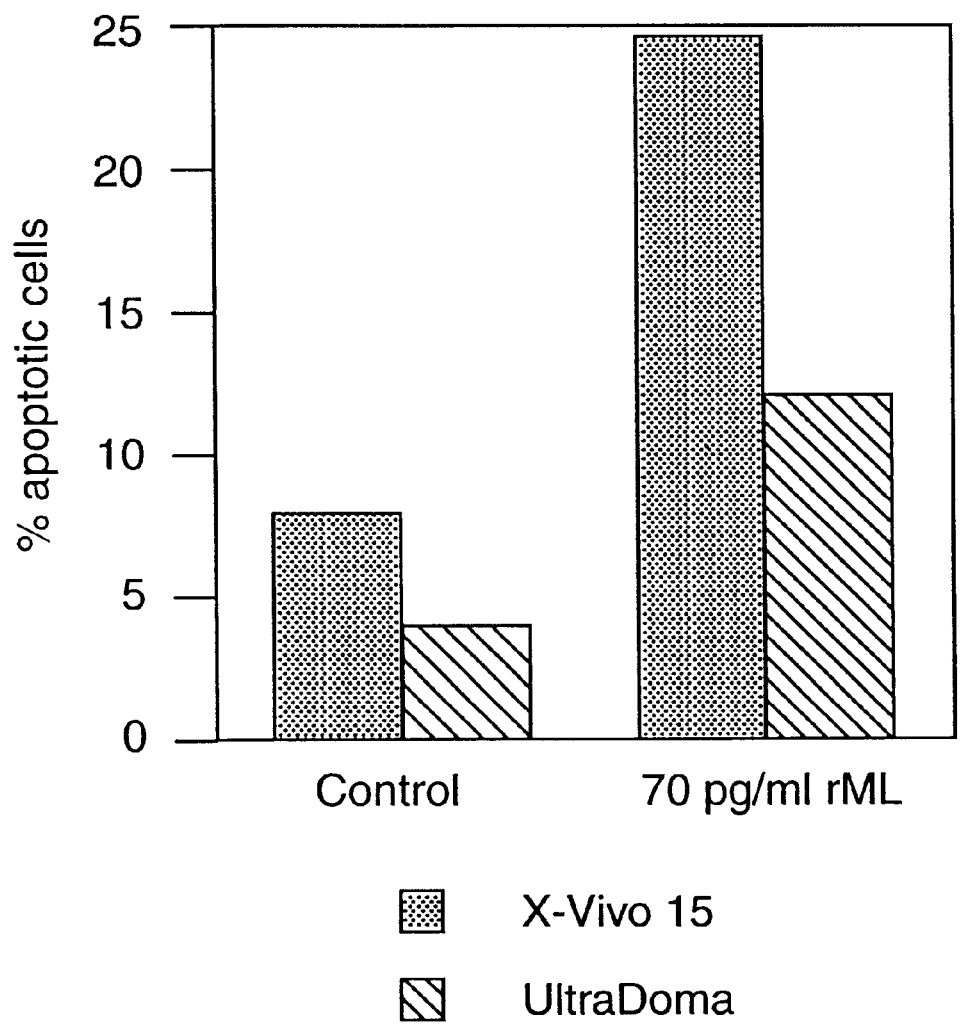
FIG. 12 shows induction of apoptosis with U937 cells by rML.
Figure 15:
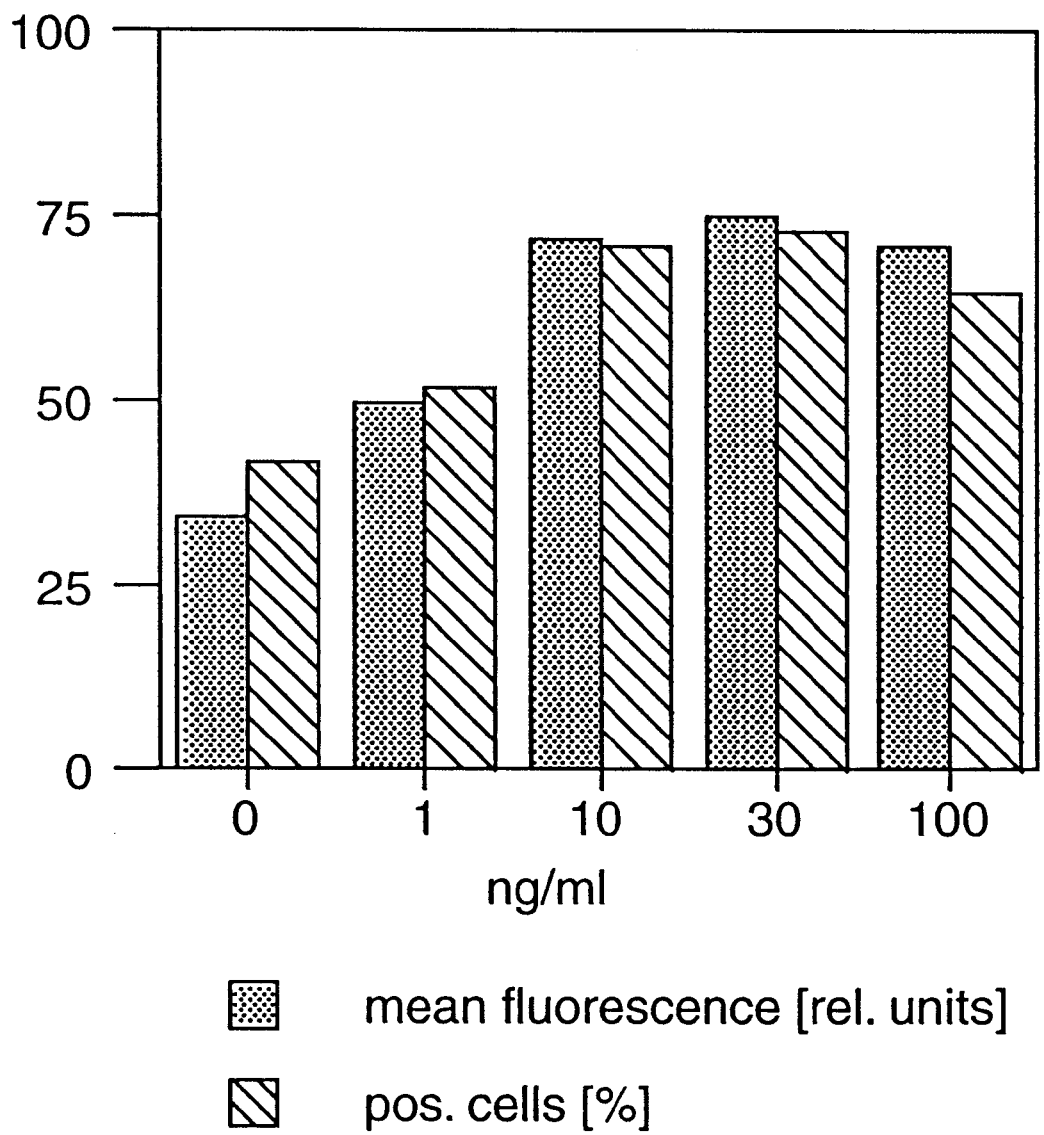
FIG. 15 shows induction of the cell surface marker cd69 in PBMC by rMLB.

The detection of the induction of apoptotic processes by recombinant mistletoe lectin (rMLA/rMLB) is carried out by staining the nucleus with the fluorescent dye DAPI [Hotz et al., 1992]. The typical apoptotic changes in the nucleus' morphology can be made visible under the microscope and can be quantified by counting 500–100 cells per sample. It is essential for the sensitivity of the assay to use serum-free medium since the presence of serum proteins dramatically reduces the available amount of lectin (by about the factor 40 at 10% FCS, Ribereau-Gayon et al., 1995). The induction time of 24 hrs allows only partially a direct correlation with the MOLT assay, since the cytotoxic effect is clearly visible in the viability assay only after 72 hrs, apoptosis, however, is an effect that can be detected earlier. If the incubation times are too long, apoptosis is blotted out by secondary necrosis. FIG. 12 shows a marked increase in the rate of apoptotic U937 cells after treatment with recombinant ML holoprotein. At 70 pg/ml the number of apoptotic cells after 24 hrs in two different cultures in serum-free media is increased by factor 3. Hence, the recombinant mistletoe lectin like the naturally occurring protein [Janssen et al., 1993] is capable of inducing apoptotic cell death.

Example 13
Immunostimulating Effect of Recombinant Mistletoe Lectin in the PBMC Model The cytokines TNF-α (monocytes, macrophages) and IFN-γ (T helper cells) are central mediators within the complex network of the human immunological system. Human, mononuclear cells (PBMC, contain monocytes and lymphocytes) from healthy blood donors were isolated by FICOLL-PAQUE® density gradient centrifugation in accordance with the instructions of the producer (Pharmacia, Sweden). For induction of the release of TNF-α, the cells ($4 \times 10^6$ mononuclear cells/ml) were incubated in RPMI 1640 medium containing 10% (v/v) fetal calf serum, 100 U/ml penicillin, 100 μg/ml streptomycin first for 18 hrs with the recombinant mistletoe lectin proteins alone and then for further 24 hrs with 1 μg/ml lipopolysaccharides from Salmonella abortus equi as costimulating factor at 37° C., 5% $CO_2$ and >95% relative humidity in U-shaped microtiter cell culture plates in an incubator provided with gas. Then the concentration of TNF-α was quantified in the cell-free supernatants by any ELISA (Genzyme Diagnostics, R üsselsheim). For induction of the release of IFN-γ, the cells were incubated in the above-mentioned medium for 1 hr with the recombinant mistletoe lectin proteins alone and then for further 65 hrs with 0.5 μg/ml phytohemagglutinin-L as costimulating factor as described above. Then the respective concentration of IFN-γ was quantified in the cell-free supernatants by an ELISA (ENDOGEN INC., Cambridge, USA).

Example 14
Immunostimulating Effect of Recombinant Mistletoe Lectin in the $Skin^2$ ZK1200 Model The $skin^2$ model established as bioassay consists of a three-dimensional fibroblast-containing skin and a structured epidermis from unkeratinized keratinocytes in their own, naturally secreted matrix [Joller et al., 1996]. The skin tissue pieces ($11 \times 11$ $mm^2$, prepared from human, primary cells; Advanced Tissue Sciences Inc. (ATS), La Jolla, USA) were provided on a nylon grid in agarose and transferred to special medium A (ATS, La Jolla, USA) immediately upon receipt. Both IL-1α and Il-6 are relevant, stimulating cytokines of the human immunological system. For induction of the release of IL-1α or IL-6 the skin² tissue pieces were incubated along with the test substance in 2 ml of special medium B (ATS; La Jolla, USA) for 24 hrs at 37° C., 5% $CO_2$ in air and >95% relative humidity in 12-cup cell culture plates (Corning Glass Works, Corning, USA). Then the concentrations of IL-1α (Quantikine human IL-1α Assay, R&D Systems Inc., Minneapolis, USA) and IL-6 (h-interleukin 6 ELISA, Boehringer Mannheim GmbH) were quantified in the cell-free supernatants by an ELISA.

The skin² model was characterized by a dosage-dependent release of IL-1α induced by 0.25–8 ng rML/ml and by a dosage-dependent release of IL-6 induced by 05–8 ng rML/ml (FIG. 14). Surprisingly, none of the above-mentioned cytokine releases could be achieved with the recombinant rMLB chain alone. This finding absolutely contradicts the prior art knowledge according to which the immunostimulating activity was mainly attributed to the lectin activity of the B chain [Hajto et al., 1990].

Example 15
Activation of Immunocompetent Cells by Recombinant Mistletoe Lectin B Chain (rMLB)

Activation of immunocompetent cells was examined using the induction of the cell surface protein CD69. CD69 appears as one of the first cell surface antigens after activation of T cells, B cells and particularly of natural killer cells (NK cells) which, due to their capability of recognizing and lysing neoplastic cells, play a central part in the natural defense against tumors. CD69 is an activation marker of the above-mentioned immunocompetent cell populations since the cell surface protein is not expressed on resting lymphocytes. Furthermore, for the inducible CD69 surface protein a conducive function for the cytolytic activity of the NK cells and TcRγ/δT cells could be detected [Moretta et al., 1991]. For detection of the surface marker on human mononuclear cells by Flow Cytometry (FACS) PBMC were isolated by density gradient on a Hypaque (Sigma) similar to Example 13. After dissolving the cells in RPMI 160 medium with 5% FCS and seeding of about 250000 cells/cup of a microtiter plate the solution was incubated for 4 hrs with 1, 10, 30 and 100 ng of the test substance rMLB. Incubation for 20 min with fluorescence-labelled anti-CD69 MAb in an ice bath was followed by washing with Hank's solution with 5% FCS. The sedimented labelled cells were added to 200 μl Sheath Fluid and measured in a FACScan (Becton Dickinson). The median fluorescence is applied corresponding to the number of the CD69 cell surface marker per cell as well as the share of the CD69-positive cells in the entire cell population. In the concentration range of 1–100 ng/ml an activation of the mononuclear cells both with respect to the occurrence of CD69 on the cell surface as well as with respect to the share of CD69-positive cells could be detected. A bell-shaped dosage dependence curve could be observed. A cytotoxic effect on the PBMC examined in the present example could not be detected, not even at the highest concentration of 100 ng/ml rMLB.

Literature

Babbitt, P. C., West, B. L., Buechter, D. D., Kuntz, I. D. and Kenyon, G. L. [1990]: Removal of a proteolytic activity associated with aggregates formed from expression of creatine kinase in *Escherichia coli* leads to improved recovery of active enzyme. Bio/Technology 8, 945–949.

Baur, A., Buschinger, A. and Zimmermann, F. K. (1993): Molecular cloning and sequencing of 18S rDNA fragments of six different ant species. Ins. Soc. 40, 325–335.

Beuth, J., Ko, H. L., Gabius, H.-J. and Pulverer, G. [1991]: Influence of treatment with the immunomodulatory effective dose of the β-galactoside-specific lectin from Mistletoe on tumor colonization in BALB/c-mice for two experimental model systems. in vivo 5, 29–32.

Beuth, J., Ko, H. L., Gabius, H.-J., Burrichter, H., Oette, K. and Pulverer, G. [1992]: Behavior of lymphocyte subsets and expression of activation markers in response to immunotherapy with galacto-side-specific lectin from mistletoe in breast cancer patients. Clin. Investig. 70, 658–661.

Beuth, J., Ko, H. L., Tunggal, L., Steuer, M. K., Geisel, J., Jeljaszewicz, J. and Pulverer, G. [1993]: Thymocyte proliferation and maturation in response to galactoside-specific Mistletoe Lectin-1. in vivo 7, 407–410.

Beuth, J., Ko, K. L., Tunggal, L., Geisel, J. and Pulverer, G. [1993]: Vergleichende Untersuchungen zur immunaktiven Wirkung von Galactosid-spezifischem Mistellektin. Arzneim. Forsch. 43, 166–169.

Bocci, V. [1993]: Mistletoe (*Viscum album*) lectins as cytokine inducers and immunoadjuvant in tumor therapy. J. of Biological Regulators and Homeostatic Agents 7, 1–6.

Beuth, J., Ko, H. L., Tungal, L., Buss, G., Jeljaszewicz,J., Steuer, M. K. and Pulverer, G. [1994]: Immunaktive Wirkung von Mistellektin-1 in Abhängigkeit von der Dosierung. Arzneim. Forschung 44, 1255–1258.

Bradford, M. M. [1976]: A rapid and sensitive method for the quantitation of microgram quantities of protein utilizing the principle of protein-dye binding. Analytical Biochemistry 72, 248–254.

Dietrich, J. B., Ribéreau-Gayon. G., Jung, M. L., Franz, H., Beck, J. P. and Anton, R. [1992]: Identity of the N-terminal sequences of the three A chains of mistletoe (*Viscum album* L.) lectins: homology with ricin-like plant toxins and single-chain ribosome-inhibiting proteins. Anti-Cancer Drugs 3, 507–511.

Eifler, R., Pfüller, K., Göckeritz, W. and Püwller, U. [1994]:Improved procedures for isolation and standardization of mistletoe lectins and their subunits: implications for the analysis of lectin pattern of the european mistletoe. In: Lectins Biology-Biochemistry Clinical Biochemistry (Bog-Hansen, Hrsg.) Vol. 9, M/S Wiley, New Delhi.

Endo, Y., Tsurugi, K. and Franz, H. [1988a]: The site of action of the A-chain of mistletoe lectin I on eukaryotic ribosomes. The RNA N-glycosidase activity of the protein. FEBS Lett. 231, 378–80.

Endo, Y., Tsurugi, K. and Lambert, J. M. [1988b]: The site of action of six differtent ribosom-inactivating proteins from plants on eukaryotic ribosomes: the RNA N-glycosidase activity of the proteins. Biochem. Biophys. Res. Commun. 150, 1032–1036.

Erlich, H. A., Gelfand, D. H. and Saiki, R. K. [1988]: Specific DNA amplification. Nature 331, 461.

Franz, H., Haustein, B., Luther, P., Kuropka, U. and Kindt, A. [1977]: Isolierung und Charakterisierung von Inhaltsstoffen der Mistel (*Viscum album* L.) I. Affinit ätschromatographie an fixierten Plasmaproteinen. Acta biol. med. germ. 36, 113–117.

Frohman, M. A., Dush, M. K. and Martin, G. R. [1988]: Rapid production of full-length cDNAs from rare transcripts: Amplification using a single gene-specific oligonucleotide primer. Proc. Natl. Acad. Sci. USA 85, 8998–9002.

Gabius, H.-J., Walzel, H., Joshi, S. S., Kruip, J., Kojima, S., Gerke, V., Kratzin, H. and Gabius, S. [1992]:The immunomodulatory β-galactoside-specific lectin from Mistletoe: Partial sequence analysis, cell and tissue binding, and impact on intracellular biosignalling of monocytic leukemia cells. Anticancer Res. 12, 669–676.

Gabius, H.-J., Gabius, S., Joshi, S. S., Koch, B., Schroeder, M., Manzke, W. M. and Westerhausen, M. [1993]: From III-defined extracts to the immunomodulatory lectin: Will there be a reason for oncological application of Mistletoe ? Planta Med. 60, 2–7.

Gabius, H.-J. and Gabius, S. [1994]: Die Misteltherapie auf dem naturwissenschaftlichen Prüfstand. PZ 139, 9–16.

Ganguly, C. and Das, S. [1994]: Plant Lectins as inhibitors of tumor growth and modulators of host immune response. Chemotherapy 40, 272–278.

Garcia-Olmedo, F., Carbonero, P., Hernandez-Lucas, C., Paz-Ares, J., Ponz, F., Vicente, O. and Sierra, J. M. [1983]: Inhibition of eukaryotic cell-free protein synthesis by thionins from Wheat endosperm. Biochim. Biophys. Acta 740, 52–56.

Gribskov, M., Devereux, J. and Burgess, R. [1984] Nucl. Acids Res. 12, 539–549.

Hajto, T. [1986]: Immunmodulatory effects of Iscador: A Viscum album preparation. Oncology 43 suppl. 1, 51–65.

Hajto, T., Hostanska, K. and Gabius, H.-J. [1989]: Modulatory potency of the β-galactoside-specific lectin from Mistletoe extract (Iscador) on the host defense system in vivo in Rabbits and Patients. Cancer Res. 49, 4803–4808.

Hajto, T., Hostanska, K., Frei, K., Rordorf, C. and Gabius, H.-J. [1990]: Increased secretion of Tumor necrosis factor a, Interleukin 1, and Interleukin 6 by Human Mononuclear Cells exposed to β-Galactoside-specific lectin from clinically applied Mistletoe extract. Cancer Res. 50, 3322–3326.

Harlowe, E. and Spur, D. [1988] In: Antibodies. A laboratory manual. Cold Spring Harbor Laboratory, Cold Spring Harbor, N.Y.

Heiny, B.-M. and Beuth, J. [1994]: Mistletoe extract standardized for the galactoside-specific lectin (ML-1) induces β-endorphin release and immunopotentiation in breast cancer patients. Anticancer Research 14, 1339–1342.

Hotz, M., Del Bino, G., Lassota, P., Traganos, F., Darzynkiewicz, Z. [1992] Cytostatic and cytotoxic effects of fostriecin on human promyelocytic HL-60 and lymphocytic MOLT-4 leukemic cells. Cancer Res. 52, 1530–1535.

Hülsen, H., Doser, C. and Mechelke, F. [1986]: Differences in the in vitro effectiveness of preparations produced from Mistletoes of various host trees. Drug. Res. 36, 433–436.

Jäggy, C., Musielski, H., Urech, K. and Schaller, G. [1995]: Quantitative Determination of lectins in Mistletoe preparations. Arzneim.-Forsch./Drug Res. 45, 905–909.

Janssen, O., Scheffler, A., and Kabelitz, D. [1993] In vitro Effects of Misteletoe Extracts and Mistletoe Lectins. Cytotoxicity towards tumor cells due to the induction of programmed cell death (apoptosis). Arzneim. forsch. 43, 1221–1227.

Joller, P. W., Menrad, J. M., Schwarz, T., Pfüller, U., Parnham, M. L., Weyhenmeyer, R. and Lentzen, H. [1996]: Stimulation of cytokine production via a special standardized Mistletoe preparation in an in vitro skin bioassay. Arzneim.-Forsch./Drug Res. 46, 649–653.

Katzin, B. J., Collins, E. J. and Robertus, J. D. [1991]: Structure of Ricin A-Chain at 2. 5 Å. Proteins 10, 251–259.

Kim, Y., Misna, D., Monzingo, A. F., Ready, M. P., Frankel, A., and Robertus, J. D. [1992]: Structure of a Ricin mutant showing rescue of activity by a noncatalytic residue. Biochemistry, 31, 3294–3296.

Lord, J. M., Roberts, L. M. and Robertus, J. D. [1994]: Ricin: structure, mode of action, and some current applications. FASEB J. 8, 201–208.

Männel, D. N., Becker, H., Gundt, A., Kist, A. and Franz, H. [1991]: Induction of tumor necrosis factor expression by a lectin from Viscum album. Cancer Immunol. Immunother. 33, 177–182.

Minowada, J., Ohnuma, T., Moore, G. E. [1972] Rosetteforming human lymphoid cell lines. J. Nat. Cancer Inst. 49, 891–895.

Mendez, E., Moreno, A., Colilla, F., Pelaez, F., Limas, G. G., Mendez, R., Soriano, F., Salinas, M. and de Haro, C. [1990]: Primary structure and inhibition of protein synthesis in eukaryotic cell-free system of a novel thionin, g-hordothionin, from barley endosperm. Eur. J. Biochem. 194, 533–539.

Moretta, A. et al. [1991] J. Exp. Med. 172, 701–707.

Ribereau-Gayon, G., Jung, M.-L., Beck, J.-P., Anton, R. [1995]: Effect of fetal calf serum on the cytotoxic activity of Mistletoe (Viscum album L.) lectins in cell culture. Phytotherapy Res. 9, 336–339.

Rutenber, E. and Robertus, J. D. [1991]: Structure of Ricin B-chain at 2. 5 Å resolution. Proteins 10, 260–269.

Scudiero, P. A. et al. [1988] Cancer Res. 48, 4827–4823.

Stein, G. and Berg, P. A. [1994]: Non-lectin component in a fermented extract from Viscum album L. grown on pines induces proliferation of lymphocytes from heallthy and allergic individuals in vitro. Eur. J. Clin. Pharmacol. 47, 33–38.

Stirpe, F., Barbieri, L., Battelli, M. G., Soria, M. and Lappi, D. A. [1992]: Ribosome-inactivating proteins from plants: Present status and future prospects. Bio/Technology 10, 405–412.

Studier, F. W. and Moffart, B. A. [1986]: Use of Bacteriophage T7 RNA Polymerase to direct selective high-level expression of cloned genes. J. Mol. Biol. 189, 113–130.

Tonevitsky, A. G., Rakhmanova, V. A., Agapov, I. I., Shamshiev, A. T., Usacheva, E. A., Prokoph'ev, S. A., Denisenko, O. N., Alekseev, Y. and Pfueller, U. (1995): The interactions of anti-MLI monoclonal antibodies with isoforms of the lectin from Viscum album. Immunol. Lett. 44, 31–4.

Vitetta, E. S., Thorpe, P. E., Uhr, J. W. (1993) Immunotoxins: magic bullets or misguided missiles? Immunol. Today, 14, 252–259.

Weston, S. A., Tucker, A. D., Thatcher, D. R., Derbyshire, D. J. and Pauptit, R. A. [1994]: X-ray structure of recombinant Ricin A-Chain at 1.8 Å resolution. J. Mol. Biol. 244, 410–422.

What is claimed is:

1. An isolated nucleic acid molecule
    (a) comprising a nucleic acid sequence as depicted in FIG. 4c or encoding a protein or preproprotein comprising the amino acid sequence as depicted in FIG. 4c (SEQ ID NOS: 34 and 35); or
    (b) comprising a nucleic acid sequence encoding a fragment of a protein or preproprotein according to (a) having more of the following biological activities: cytotoxicity, immunostimulation, endorphin stimulation, stimulation of release of inflamatory cytokines, apoptosis induction or antigenicity; or
    (c) comprising a nucleic acid sequence that differs from the nucleic acid molecule according to (a) or (b) due to the degeneracy of the genetic code, but which encodes a polypeptide having a biological activity indicated in (b); or
    (d) comprising a nucleic acid sequence that specifically hybridizes to primer RMLA2 (SEQ ID NO:2) in 10 mM Tris-HCl, 1.5 mM MgCl$_2$, 50 mM KCl, at 50° C. at pH 8.3; and encodes a polypeptide having a biological activity indicated in (b).

2. An isolated nucleic acid molecule comprising a nucleotide sequence coding for the A chain of the mistletoe lectin or a fragment thereof having the biological activity of enzymatic inactivation of ribosomes.

3. An isolated nucleic acid molecule comprising a nucleotide sequence coding for the B chain of the mistletoe lectin or a fragment thereof having the biological activity of carbohydrate binding.

4. The isolated nucleic acid molecule according to any one of claims 1, 2 or 3 which is a DNA molecule.

5. The isolated nucleic acid molecule according to any one of claims 1, 2 or 3 which is a RNA molecule.

6. An isolated nucleic acid molecule which is an antisense strand to the nucleic acid molecule according to any one of claims 1, 2 or 3.

7. A vector which comprises at least one isolated nucleic acid molecule according to any one of claims 1, 2, or 3.

8. The vector according to claim 7 which is an expression vector.

9. A host cell which is transformed with at least one vector according to claim 7.

10. The host cell according to claim 9 which is a mammalian cell, a bacterium, a fungal cell, a yeast cell, or an insect cell.

11. The host cell according to claim 10, wherein the bacterium is *E. coli*, the fungal cell is an Aspergillus cell and the insect cell is a Spodoptera cell.

12. A polypeptide encoded by the at least one isolated nucleic acid molecule and expressed by the host cell according to claim 10.

13. A polypeptide encoded by the at least one isolated nucleic acid molecule and expressed by the host cell according to claim 10, wherein the host cell is a bacterium.

14. An isolated, structurally homogeneous polypeptide expressed by the host cell according to claim 9, wherein said polypeptide is encoded by the vector comprised in the host cell.

15. The polypeptide of claim 14 which is a fusion protein.

16. The polypeptide of claim 14 which is glycosylated.

17. The polypeptide of claim 14 which is non-glycosylated.

18. An isolated, structurally homogeneous polypeptide coded for and expressed by the vector according to claim 7.

19. The polypeptide of claim 18 which is a fusion protein.

20. The polypeptide of claim 18 which is glycosylated.

21. The polypeptide of claim 18 which is non-glycosylated.

22. An isolated, structurally homogeneous polypeptide which is coded for by and expressed recombinantly from the nucleic acid molecule according to any of claims 1, 2, or 3.

23. The polypeptide according to claim 22 which exhibits at least one chemical or enzymatic modification.

24. The polypeptide according to claim 22 which is a fusion protein.

25. An antibody or fragment or derivative thereof which specifically binds the polypeptide according to claim 22.

26. An immunotoxin comprising at least one polypeptide according to claim 22.

27. A pharmaceutical composition comprising the immunotoxin according to claim 26 in admixture with a pharmaceutically acceptable carrier.

28. A pharmaceutical composition comprising a carrier and the polypeptide according to claim 22.

29. A composition containing at least the polypeptide according to claim 22.

30. The polypeptide of claim 22 which is glycosylated.

31. The polypeptide of claim 22 which is non-glycosylated.

32. A process for producing a polypeptide which is coded for by and expressed recombinantly from the nucleic acid molecule according to any of claims 1, 2, or 3, the process comprising transforming, a host cell with at least one vector comprising at least one of the nucleic acid molecule(s) culturing the host under appropriate conditions for expression, and isolating the polypeptide so obtained.

33. The process of claim 32 wherein the polypeptide is glycosylated.

34. The process of claim 32 wherein the polypeptide is non-glycosylated.

35. A primer or primer pair which specifically hybridizes to the nucleic acid molecule according to any of claims 1, 2, or 3, or to the complementary strand thereof.

36. A composition containing at least a primer and/or a primer pair according to claim 35.

37. A composition containing at least the nucleic acid molecule according to any of claims 1, 2, or 3.

38. A vector which comprises both an isolated nucleic acid molecule according to claim 2 and an isolated nucleic acid molecule according to claim 3.

39. A host cell which is transformed with at least one vector according to claim 38.

40. An isolated, structurally homogeneous polypeptide dimer comprising a first monomer and second monomer, wherein the first monomer is coded for by the isolated nucleic acid molecule according to claim 2, and the second monomer by the isolated nucleic acid molecule according to claim 3; and, wherein the isolated, structurally homogeneous polypeptide dimer is expressed recombinantly.

41. The polypeptide dimer according to claim 40, wherein at least one of the monomers exhibits at least one modification or is a fusion protein.

42. An antibody or fragment or derivative thereof which specifically binds the polypeptide dimer according to claim 40.

43. A process for the producing the polypeptide dimer according to claim 40, comprising transforming a host cell with at least one vector comprising the isolated nucleic acid molecules encoding the monomers, culturing the host cell under appropriate conditions and isolating the polypeptide dimer so obtained.

44. The process of claim 43 wherein the polypeptide is glycosylated.

45. The process of claim 43 wherein the polypeptide is non-glycosylated.

46. An immunotoxin comprising at least one polypeptide dimer according to claim 40.

47. A pharmaceutical composition comprising the polypeptide dimer according to claim 40 in admixture with a pharmaceutically acceptable carrier.

48. A composition containing at least polypeptide dimer according to claim 40.

49. The polypeptide of claim 46 which is glycosylated.

50. The polypeptide of claim 40 which is non-glycosylated.

51. An isolated nucleic acid molecule comprising the nucleotide sequence depicted in FIG. 4a (SEQ ID NO: 30) or comprising a nucleotide sequence encoding a polypeptide comprising the amino acid sequence as set forth in FIG. 4a (SEQ ID NO: 31).

52. An isolated nucleic acid molecule comprising the nucleotide sequence depicted in FIG. 4b (SEQ ID NO: 32) or comprising a nucleotide sequence encoding a polypeptide comprising the amino acid sequence as set forth in FIG. 4b (SEQ ID NO: 33).

53. An isolated nucleic acid molecule comprising a nucleotide sequence encoding mistletoe lectin having one or more of the following biological activities: cytotoxicity, immunostimulation, endorphin stimulation, stimulation of release of inflamatory cytokines, apoptosis induction or antigenicity.

54. An isolated nucleic acid molecule comprising the nucleotide sequence depicted in FIG. 4c (SEQ ID NO: 34).

55. An isolated nucleic acid molecule: comprising any one of RMLA1 (SEQ ID NO: 1), RMLA2 (SEQ ID NO: 2), RMLB1 (SEQ ID NO: 3), RMLB2 (SEQ ID NO: 4), RMLB3 (SEQ ID NO: 5) of FIGS. 1b or 1c; or comprising any one of fragments h (nucleotides 1–204, SEQ ID NO: 36), f (nucleotides 205–909, SEQ ID NO: 38), c (nucleotides 910–957SEQ ID NO: 40), g (nucleotides 958–1746, SEQ ID NO: 42), and i (nucleotides 1747–1923, SEQ ID NO: 44); or comprising a nucleotide sequence encoding a polypeptide encoded by any one of fragments h (SEQ ID NO: 37), f (SEQ ID NO: 39), e (SEQ ID NO: 41), g (SEQ ID NO: 43), of FIG. 4c.

56. The host cell according to claim 11 wherein the Spodoptera cell is a *Spodoptera frugiperda* cell.

* * * * *

UNITED STATES PATENT AND TRADEMARK OFFICE
CERTIFICATE OF CORRECTION

PATENT NO. : 6,271,368 B1
DATED : August 7, 2001
INVENTOR(S) : Lentzen et al.

It is certified that error appears in the above-identified patent and that said Letters Patent is hereby corrected as shown below:

Column 61, claim 1,
Line 43, before "more", insert -- one or --.

Signed and Sealed this

Twelfth Day of February, 2002

Attest:

JAMES E. ROGAN
Attesting Officer    Director of the United States Patent and Trademark Office

UNITED STATES PATENT AND TRADEMARK OFFICE
CERTIFICATE OF CORRECTION

PATENT NO. : 6,271,368 B1
DATED : August 7, 2001
INVENTOR(S) : Lentzen et al.

It is certified that error appears in the above-identified patent and that said Letters Patent is hereby corrected as shown below:

Title page,
Item [73], Assignee: delete "Madus AG Köln" and insert -- Madaus AG --.

Signed and Sealed this

Eleventh Day of February, 2003

JAMES E. ROGAN
*Director of the United States Patent and Trademark Office*